(12) United States Patent
Lieberburg et al.

(10) Patent No.: US 8,613,920 B2
(45) Date of Patent: Dec. 24, 2013

(54) TREATMENT OF AMYLOIDOGENIC DISEASES

(75) Inventors: Ivan Lieberburg, Berkeley, CA (US); James Callaway, San Diego, CA (US); Michael Grundman, San Diego, CA (US)

(73) Assignees: Janssen Alzheimer Immunotherapy (IE); Wyeth LLC, Madison, NJ (US)

( * ) Notice: Subject to any disclaimer, the term of this patent is extended or adjusted under 35 U.S.C. 154(b) by 276 days.

(21) Appl. No.: 12/297,636

(22) PCT Filed: Jul. 27, 2007

(86) PCT No.: PCT/US2007/009499
§ 371 (c)(1),
(2), (4) Date: May 10, 2010

(87) PCT Pub. No.: WO2009/017467
PCT Pub. Date: Feb. 5, 2009

(65) Prior Publication Data
US 2010/0221187 A1      Sep. 2, 2010

(51) Int. Cl.
*A61K 39/395* (2006.01)
*A61K 49/06* (2006.01)
*A61P 9/12* (2006.01)
*A61P 5/44* (2006.01)

(52) U.S. Cl.
USPC ..... 424/133.1; 424/139.1; 424/9.2; 514/12.2; 514/15.7

(58) Field of Classification Search
None
See application file for complete search history.

(56) References Cited

U.S. PATENT DOCUMENTS

| | | |
|---|---|---|
| 4,666,829 A | 5/1987 | Glenner et al. |
| 4,713,366 A | 12/1987 | Stevens |
| 4,816,397 A | 3/1989 | Boss et al. |
| 4,816,567 A | 3/1989 | Cabilly et al. |
| 4,879,213 A | 11/1989 | Fox et al. |
| 4,883,666 A | 11/1989 | Sabel et al. |
| 4,912,206 A | 3/1990 | Goldgaber et al. |
| 5,004,697 A | 4/1991 | Pardridge |
| 5,057,540 A | 10/1991 | Kensil et al. |
| 5,096,706 A | 3/1992 | Flint |
| 5,187,153 A | 2/1993 | Cordell et al. |
| 5,192,753 A | 3/1993 | McGeer et al. |
| 5,208,036 A | 5/1993 | Eppstein et al. |
| 5,220,013 A | 6/1993 | Ponte et al. |
| 5,225,539 A | 7/1993 | Winter |
| 5,227,159 A | 7/1993 | Miller |
| 5,231,000 A | 7/1993 | Majocha et al. |
| 5,231,170 A | 7/1993 | Averback |
| 5,245,015 A | 9/1993 | Fung et al. |
| 5,258,498 A | 11/1993 | Huston et al. |
| 5,262,332 A | 11/1993 | Selkoe |
| 5,270,165 A | 12/1993 | Van Nostrand et al. |
| 5,278,049 A | 1/1994 | Baker et al. |
| 5,358,708 A | 10/1994 | Patel |
| 5,385,887 A | 1/1995 | Yim et al. |
| 5,387,742 A | 2/1995 | Cordell |
| 5,417,986 A | 5/1995 | Reid et al. |
| 5,434,170 A | 7/1995 | Andrulis, Jr. |
| 5,441,870 A | 8/1995 | Seubert et al. |
| 5,464,823 A | 11/1995 | Lehrer et al. |
| 5,470,951 A | 11/1995 | Roberts |
| 5,472,693 A | 12/1995 | Gourlie et al. |
| 5,514,548 A | 5/1996 | Krebber et al. |
| 5,530,101 A | 6/1996 | Queen et al. |
| 5,571,499 A | 11/1996 | Hafler et al. |
| 5,571,500 A | 11/1996 | Hafler et al. |
| 5,576,184 A | 11/1996 | Better et al. |
| 5,583,112 A | 12/1996 | Kensil et al. |
| 5,585,089 A | 12/1996 | Queen et al. |
| 5,585,100 A | 12/1996 | Mond et al. |
| 5,589,154 A | 12/1996 | Anderson |
| 5,593,846 A | 1/1997 | Schenk et al. |
| 5,601,827 A | 2/1997 | Collier et al. |
| 5,605,811 A | 2/1997 | Seubert et al. |
| 5,612,486 A | 3/1997 | McConlogue et al. |
| 5,618,920 A | 4/1997 | Robinson et al. |
| 5,620,844 A | 4/1997 | Neurath et al. |
| 5,622,701 A | 4/1997 | Berg |
| 5,624,821 A | 4/1997 | Winter et al. |
| 5,624,937 A | 4/1997 | Reel et al. |
| 5,641,473 A | 6/1997 | Hafler et al. |
| 5,641,474 A | 6/1997 | Hafler et al. |
| 5,645,820 A | 7/1997 | Hafler et al. |
| 5,648,260 A | 7/1997 | Winter et al. |
| 5,652,334 A | 7/1997 | Roberts |

(Continued)

FOREIGN PATENT DOCUMENTS

| | | |
|---|---|---|
| AU | 707083 | 7/1999 |
| EP | 285 159 A1 | 10/1988 |

(Continued)

OTHER PUBLICATIONS

Greaves et al. (Aug. 2006) Posterior reversible encephalopathy syndrome following anti-lymphocyte globulin treatment for severe aplastic anaemia. Br. J. Haematol. 134(3):251.*

(Continued)

*Primary Examiner* — Kimberly A Ballard
(74) *Attorney, Agent, or Firm* — Alston & Bird LLP

(57) ABSTRACT

The invention provides preferred dosage ranges, maximum concentrations, average concentrations and monitoring regimes for use in treatment of Alzheimer's disease using antibodies to Aβ. The invention also provides monitoring regimes that can assess changes in symptoms or signs of the patient following treatment.

36 Claims, 11 Drawing Sheets

(56) References Cited

U.S. PATENT DOCUMENTS

| | | |
|---|---|---|
| 5,677,425 A | 10/1997 | Bodmer et al. |
| 5,679,348 A | 10/1997 | Nesburn et al. |
| 5,688,651 A | 11/1997 | Solomon |
| 5,693,761 A | 12/1997 | Queen et al. |
| 5,693,762 A | 12/1997 | Queen et al. |
| 5,702,906 A | 12/1997 | Rosenthal |
| 5,721,130 A | 2/1998 | Seubert et al. |
| 5,723,130 A | 3/1998 | Hancock et al. |
| 5,731,284 A | 3/1998 | Williams |
| 5,733,547 A | 3/1998 | Weiner et al. |
| 5,733,548 A | 3/1998 | Restifo et al. |
| 5,736,142 A | 4/1998 | Sette et al. |
| 5,744,132 A | 4/1998 | Warne et al. |
| 5,744,368 A | 4/1998 | Goldgaber et al. |
| 5,750,349 A | 5/1998 | Suzuki et al. |
| 5,750,361 A | 5/1998 | Prusiner et al. |
| 5,753,624 A | 5/1998 | McMichael et al. |
| 5,766,846 A | 6/1998 | Schlossmacher et al. |
| 5,770,700 A | 6/1998 | Webb et al. |
| 5,773,007 A | 6/1998 | Penney et al. |
| 5,776,468 A | 7/1998 | Hauser et al. |
| 5,780,587 A | 7/1998 | Potter |
| 5,786,180 A | 7/1998 | Konig et al. |
| 5,798,102 A | 8/1998 | McMichael et al. |
| 5,817,626 A | 10/1998 | Findeis et al. |
| 5,824,322 A | 10/1998 | Balasubramanian |
| 5,837,268 A | 11/1998 | Potter et al. |
| 5,837,473 A | 11/1998 | Maggio et al. |
| 5,837,672 A | 11/1998 | Schenk et al. |
| 5,846,533 A | 12/1998 | Prusiner |
| 5,849,298 A | 12/1998 | Weiner et al. |
| 5,851,996 A | 12/1998 | Kline |
| 5,854,204 A | 12/1998 | Findeis et al. |
| 5,854,215 A | 12/1998 | Findeis et al. |
| 5,858,981 A | 1/1999 | Schreiber et al. |
| 5,859,205 A | 1/1999 | Adair et al. |
| 5,866,129 A | 2/1999 | Chang et al. |
| 5,869,046 A | 2/1999 | Presta et al. |
| 5,869,054 A | 2/1999 | Weiner et al. |
| 5,869,093 A | 2/1999 | Weiner et al. |
| 5,877,399 A | 3/1999 | Hsiao et al. |
| 5,891,991 A | 4/1999 | Wasco et al. |
| 5,895,654 A | 4/1999 | Hartford et al. |
| 5,910,427 A | 6/1999 | Mikayama |
| 5,935,927 A | 8/1999 | Vitek et al. |
| 5,955,079 A | 9/1999 | Mond et al. |
| 5,955,317 A | 9/1999 | Suzuki et al. |
| 5,958,883 A | 9/1999 | Snow |
| 5,985,242 A | 11/1999 | Findeis et al. |
| 5,989,566 A | 11/1999 | Cobb et al. |
| 5,994,083 A | 11/1999 | Felici et al. |
| 6,015,662 A | 1/2000 | Hackett et al. |
| 6,022,859 A | 2/2000 | Kiessling et al. |
| 6,054,297 A | 4/2000 | Carter et al. |
| 6,057,098 A | 5/2000 | Buechler et al. |
| 6,057,367 A | 5/2000 | Stamler et al. |
| 6,096,318 A | 8/2000 | Stevens |
| 6,114,133 A | 9/2000 | Seubert et al. |
| 6,121,022 A | 9/2000 | Presta et al. |
| 6,150,091 A | 11/2000 | Pandolfo et al. |
| 6,165,745 A | 12/2000 | Ward et al. |
| 6,175,057 B1 | 1/2001 | Mucke et al. |
| 6,180,370 B1 | 1/2001 | Queen et al. |
| 6,194,551 B1 | 2/2001 | Idusogie et al. |
| 6,210,671 B1 | 4/2001 | Co |
| 6,218,506 B1 | 4/2001 | Krafft et al. |
| 6,261,569 B1 | 7/2001 | Comis et al. |
| 6,262,335 B1 | 7/2001 | Hsiao et al. |
| 6,267,958 B1 | 7/2001 | Andya et al. |
| 6,270,757 B1 | 8/2001 | Warne |
| 6,277,375 B1 | 8/2001 | Ward |
| 6,284,221 B1 | 9/2001 | Schenk et al. |
| 6,284,533 B1 | 9/2001 | Thomas |
| 6,294,171 B2 | 9/2001 | McMichael |
| 6,303,567 B1 | 10/2001 | Findeis et al. |
| 6,331,440 B1 | 12/2001 | Nordstedt et al. |
| 6,339,068 B1 | 1/2002 | Krieg et al. |
| 6,372,716 B1 | 4/2002 | Bush et al. |
| 6,399,314 B1 | 6/2002 | Krishnamurthy |
| 6,407,213 B1 | 6/2002 | Carter et al. |
| 6,417,178 B1 | 7/2002 | Klunk et al. |
| 6,432,710 B1 | 8/2002 | Boss, Jr. et al. |
| 6,528,624 B1 | 3/2003 | Idusogie et al. |
| 6,538,124 B1 | 3/2003 | Idusogie et al. |
| 6,548,640 B1 | 4/2003 | Winter |
| 6,562,341 B2 | 5/2003 | Prusiner et al. |
| 6,582,945 B1 | 6/2003 | Raso |
| 6,610,493 B1 | 8/2003 | Citron et al. |
| 6,632,927 B2 | 10/2003 | Adair et al. |
| 6,639,055 B1 | 10/2003 | Carter et al. |
| 6,710,226 B1 | 3/2004 | Schenk |
| 6,713,450 B2 | 3/2004 | Frangione et al. |
| 6,727,349 B1 | 4/2004 | LaRosa et al. |
| 6,743,427 B1 | 6/2004 | Schenk |
| 6,750,324 B1 | 6/2004 | Schenk et al. |
| 6,761,888 B1 | 7/2004 | Schenk |
| 6,787,138 B1 | 9/2004 | Schenk |
| 6,787,139 B1 | 9/2004 | Schenk |
| 6,787,140 B1 | 9/2004 | Schenk |
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,808,712 B2 | 10/2004 | Schenk |
| 6,818,218 B2 | 11/2004 | Schenk |
| 6,824,780 B1 | 11/2004 | Devaux et al. |
| 6,866,849 B2 | 3/2005 | Schenk |
| 6,866,850 B2 | 3/2005 | Schenk |
| 6,875,434 B1 | 4/2005 | Schenk |
| 6,890,535 B1 | 5/2005 | Schenk |
| 6,905,686 B1 | 6/2005 | Schenk |
| 6,913,745 B1 | 7/2005 | Schenk |
| 6,923,964 B1 | 8/2005 | Schenk |
| 6,933,368 B2 | 8/2005 | Co et al. |
| 6,936,698 B2 | 8/2005 | Taylor |
| 6,946,135 B2 | 9/2005 | Schenk |
| 6,962,707 B2 | 11/2005 | Schenk |
| 6,962,984 B2 | 11/2005 | Ishiwata et al. |
| 6,972,127 B2 | 12/2005 | Schenk |
| 6,982,084 B2 | 1/2006 | Schenk |
| 7,014,855 B2 | 3/2006 | Schenk |
| 7,112,661 B1 | 9/2006 | Miller |
| 7,147,851 B1 | 12/2006 | Ponath et al. |
| 7,179,892 B2 | 2/2007 | Basi et al. |
| 7,189,819 B2 | 3/2007 | Basi et al. |
| 7,195,761 B2 | 3/2007 | Holtzman et al. |
| 7,256,273 B2 | 8/2007 | Basi et al. |
| 7,582,733 B2 | 9/2009 | Basi et al. |
| 7,790,856 B2 | 9/2010 | Schenk |
| 7,871,615 B2 | 1/2011 | Basi et al. |
| 7,893,214 B2 | 2/2011 | Schenk |
| 7,906,626 B2 | 3/2011 | Raso |
| 7,928,203 B2 | 4/2011 | Schenk et al. |
| 2001/0018053 A1 | 8/2001 | McMichael |
| 2001/0021769 A1 | 9/2001 | Prusiner |
| 2002/0009445 A1 | 1/2002 | Du et al. |
| 2002/0058267 A1 | 5/2002 | Ozenberger et al. |
| 2002/0077288 A1 | 6/2002 | Frangione |
| 2002/0086847 A1 | 7/2002 | Chain |
| 2002/0094335 A1 | 7/2002 | Chalifour et al. |
| 2002/0102261 A1 | 8/2002 | Raso |
| 2002/0132268 A1 | 9/2002 | Chang et al. |
| 2002/0133001 A1 | 9/2002 | Gefter et al. |
| 2002/0136718 A1 | 9/2002 | Raso |
| 2002/0160394 A1 | 10/2002 | Wu |
| 2002/0162129 A1 | 10/2002 | Lannfelt |
| 2002/0168377 A1 | 11/2002 | Schaetzl |
| 2002/0187157 A1 | 12/2002 | Jensen et al. |
| 2002/0197258 A1 | 12/2002 | Ghanbari et al. |
| 2003/0009104 A1 | 1/2003 | Hyman et al. |
| 2003/0039645 A1 | 2/2003 | Adair et al. |
| 2003/0054484 A1 | 3/2003 | Fong et al. |
| 2003/0068316 A1 | 4/2003 | Klein et al. |
| 2003/0068325 A1 | 4/2003 | Wang |

(56) References Cited

U.S. PATENT DOCUMENTS

| | | |
|---|---|---|
| 2003/0073655 A1 | 4/2003 | Chain |
| 2003/0092145 A1 | 5/2003 | Jira et al. |
| 2003/0135035 A1 | 7/2003 | Shannon |
| 2003/0147882 A1 | 8/2003 | Solomon et al. |
| 2003/0165496 A1 | 9/2003 | Basi et al. |
| 2003/0166557 A1 | 9/2003 | Minna et al. |
| 2003/0166558 A1 | 9/2003 | Frangione et al. |
| 2003/0202972 A1 | 10/2003 | Andya et al. |
| 2003/0207828 A1 | 11/2003 | Ishiwata et al. |
| 2004/0043418 A1 | 3/2004 | Holtzman et al. |
| 2004/0081657 A1 | 4/2004 | Schenk |
| 2004/0082762 A1 | 4/2004 | Basi et al. |
| 2004/0087777 A1 | 5/2004 | Basi et al. |
| 2004/0171815 A1 | 9/2004 | Schenk et al. |
| 2004/0171816 A1 | 9/2004 | Schenk et al. |
| 2004/0197324 A1 | 10/2004 | Liu et al. |
| 2004/0213800 A1 | 10/2004 | Seubert et al. |
| 2004/0219146 A1 | 11/2004 | Schenk |
| 2004/0241164 A1 | 12/2004 | Bales et al. |
| 2004/0247590 A1 | 12/2004 | Schenk et al. |
| 2004/0247591 A1 | 12/2004 | Schenk et al. |
| 2004/0247612 A1 | 12/2004 | Wang |
| 2004/0265301 A1 | 12/2004 | Schenk et al. |
| 2004/0265308 A1 | 12/2004 | Schenk |
| 2004/0265919 A1 | 12/2004 | Vanderstichlele et al. |
| 2005/0009150 A1 | 1/2005 | Basi et al. |
| 2005/0013815 A1 | 1/2005 | Schenk |
| 2005/0019328 A1 | 1/2005 | Schenk |
| 2005/0019330 A1 | 1/2005 | Schenk |
| 2005/0048049 A1 | 3/2005 | Schenk |
| 2005/0059591 A1 | 3/2005 | Schenk et al. |
| 2005/0059802 A1 | 3/2005 | Schenk et al. |
| 2005/0090648 A1 | 4/2005 | Tsurushita et al. |
| 2005/0118651 A1 | 6/2005 | Basi et al. |
| 2005/0123534 A1 | 6/2005 | Adair et al. |
| 2005/0123544 A1 | 6/2005 | Schenk et al. |
| 2005/0136054 A1 | 6/2005 | Adair et al. |
| 2005/0142132 A1 | 6/2005 | Schenk et al. |
| 2005/0147613 A1 | 7/2005 | Raso |
| 2005/0152878 A1 | 7/2005 | Solomon et al. |
| 2005/0158304 A1 | 7/2005 | Schenk et al. |
| 2005/0163788 A1 | 7/2005 | Schenk |
| 2005/0169925 A1 | 8/2005 | Bardroff et al. |
| 2005/0191292 A1 | 9/2005 | Schenk |
| 2005/0191314 A1 | 9/2005 | Schenk |
| 2005/0196399 A1 | 9/2005 | Schenk et al. |
| 2005/0214222 A1 | 9/2005 | McKinnon et al. |
| 2005/0249725 A1 | 11/2005 | Schenk et al. |
| 2005/0249727 A1 | 11/2005 | Schenk |
| 2005/0255122 A1 | 11/2005 | Schenk |
| 2006/0029611 A1 | 2/2006 | Schenk |
| 2006/0034858 A1 | 2/2006 | Schenk |
| 2006/0057701 A1 | 3/2006 | Rosenthal et al. |
| 2006/0099206 A1 | 5/2006 | Sinacore |
| 2006/0121038 A9 | 6/2006 | Schenk et al. |
| 2006/0153772 A1 | 7/2006 | Jacobsen |
| 2006/0160161 A1 | 7/2006 | Pavlikova et al. |
| 2006/0165682 A1 | 7/2006 | Basi et al. |
| 2006/0182321 A1 | 8/2006 | Hu et al. |
| 2006/0188512 A1 | 8/2006 | Yednock et al. |
| 2006/0193850 A1 | 8/2006 | Warne et al. |
| 2006/0198851 A1 | 9/2006 | Basi et al. |
| 2006/0210557 A1 | 9/2006 | Luisi et al. |
| 2006/0210964 A1 | 9/2006 | Hyslop et al. |
| 2006/0234912 A1 | 10/2006 | Wang et al. |
| 2006/0240486 A1 | 10/2006 | Johnson-Wood et al. |
| 2006/0257396 A1 | 11/2006 | Jacobsen |
| 2006/0280743 A1 | 12/2006 | Basi et al. |
| 2007/0021454 A1 | 1/2007 | Coburn et al. |
| 2007/0072307 A1 | 3/2007 | Godavarti et al. |
| 2007/0082367 A1 | 4/2007 | Godavarti et al. |
| 2007/0134762 A1 | 6/2007 | Arumugham et al. |
| 2007/0154480 A1 | 7/2007 | Schenk |
| 2007/0161088 A1 | 7/2007 | Arumugham et al. |
| 2007/0196375 A1 | 8/2007 | Tobinick |
| 2007/0238154 A1 | 10/2007 | Basi et al. |
| 2008/0031954 A1 | 2/2008 | Paris et al. |
| 2008/0050367 A1 | 2/2008 | Basi et al. |
| 2008/0096818 A1 | 4/2008 | Schenk et al. |
| 2008/0145373 A1 | 6/2008 | Arumugham et al. |
| 2008/0219931 A1 | 9/2008 | Klunk et al. |
| 2009/0142270 A1 | 6/2009 | Schroeter et al. |
| 2009/0155256 A1 | 6/2009 | Black et al. |
| 2009/0297511 A1 | 12/2009 | Schenk |
| 2010/0221187 A1 | 9/2010 | Lieberburg et al. |
| 2010/0266505 A1 | 10/2010 | Black |
| 2011/0142824 A1 | 6/2011 | Burbidge et al. |
| 2011/0229413 A1 | 9/2011 | Lieberburg et al. |
| 2012/0070379 A1 | 3/2012 | Black et al. |

FOREIGN PATENT DOCUMENTS

| | | |
|---|---|---|
| EP | 0 391 714 A2 | 10/1990 |
| EP | 451 700 A1 | 10/1991 |
| EP | 276 723 B1 | 12/1993 |
| EP | 613 007 A2 | 2/1994 |
| EP | 616 814 A1 | 3/1994 |
| EP | 597 101 A1 | 5/1994 |
| EP | 0 613 007 A2 | 8/1994 |
| EP | 613 007 A2 | 8/1994 |
| EP | 620 276 A1 | 10/1994 |
| EP | 626 390 A1 | 11/1994 |
| EP | 666 080 A1 | 8/1995 |
| EP | 359 783 B1 | 11/1995 |
| EP | 683 234 A1 | 11/1995 |
| EP | 440 619 B1 | 1/1996 |
| EP | 758 248 B1 | 2/1997 |
| EP | 758 901 B1 | 2/1997 |
| EP | 526 511 B1 | 5/1997 |
| EP | 782 859 A1 | 7/1997 |
| EP | 783 104 A1 | 7/1997 |
| EP | 594 607 B1 | 8/1997 |
| EP | 752 886 B1 | 1/1998 |
| EP | 845 270 A1 | 6/1998 |
| EP | 1 690 547 A1 | 8/1998 |
| EP | 863 211 A1 | 9/1998 |
| EP | 868 918 A2 | 10/1998 |
| EP | 652 962 B1 | 12/1998 |
| EP | 911 036 A2 | 4/1999 |
| EP | 561 087 B1 | 8/1999 |
| EP | 639 081 B1 | 11/1999 |
| EP | 506 785 B1 | 3/2000 |
| EP | 1 172 378 A1 | 1/2002 |
| EP | 1 481 992 A2 | 12/2004 |
| EP | 1 481 992 A3 | 12/2004 |
| EP | 921 189 B1 | 1/2005 |
| EP | 1 033 998 B1 | 10/2005 |
| EP | 1 185 298 B1 | 6/2009 |
| EP | 1 321 166 B1 | 1/2011 |
| GB | 2 220 211 A | 1/1990 |
| GB | 2 335 192 A | 9/1999 |
| JP | 62-267297 A | 11/1987 |
| JP | 07-132033 A | 5/1995 |
| JP | 7-165799 A | 6/1995 |
| JP | 09/208485 | 8/1997 |
| JP | 9208485 A | 12/1997 |
| JP | 9119929 A | 6/1999 |
| WO | WO 87/02671 A | 5/1987 |
| WO | WO 87/06838 A1 | 11/1987 |
| WO | WO 88/10120 A1 | 12/1988 |
| WO | WO 89/01343 A1 | 2/1989 |
| WO | WO 89/03687 A1 | 5/1989 |
| WO | WO 89/06242 A1 | 7/1989 |
| WO | WO 89/06689 A1 | 7/1989 |
| WO | WO 90/05142 A1 | 5/1990 |
| WO | WO 90/07861 | 7/1990 |
| WO | WO 90/12870 A1 | 11/1990 |
| WO | WO 90/12871 A1 | 11/1990 |
| WO | WO 90/14837 A1 | 12/1990 |
| WO | WO 90/14840 A1 | 12/1990 |
| WO | WO 91/08760 A1 | 6/1991 |
| WO | WO 91/09967 A1 | 7/1991 |
| WO | WO 91/10741 A1 | 7/1991 |
| WO | WO 91/12816 A1 | 9/1991 |

(56) References Cited

FOREIGN PATENT DOCUMENTS

| | | |
|---|---|---|
| WO | WO 91/16819 A1 | 11/1991 |
| WO | WO 91/16928 A1 | 11/1991 |
| WO | WO 91/17271 A1 | 11/1991 |
| WO | WO 91/19795 A1 | 12/1991 |
| WO | WO 91/19810 A1 | 12/1991 |
| WO | WO 92/01047 A1 | 1/1992 |
| WO | WO 92/01059 A1 | 1/1992 |
| WO | WO 92/05793 A1 | 4/1992 |
| WO | WO 92/06187 A1 | 4/1992 |
| WO | WO 92/06708 A1 | 4/1992 |
| WO | WO 92/07944 A1 | 5/1992 |
| WO | WO 92/13069 A1 | 8/1992 |
| WO | WO 92/15330 A1 | 9/1992 |
| WO | WO 92/19267 A1 | 11/1992 |
| WO | WO 92/22653 A1 | 12/1992 |
| WO | WO 93/02189 A1 | 2/1993 |
| WO | WO 93/04194 A1 | 3/1993 |
| WO | WO 93/12227 A1 | 6/1993 |
| WO | WO 93/14200 A1 | 7/1993 |
| WO | WO 93/15760 A1 | 8/1993 |
| WO | WO 93/16724 A1 | 9/1993 |
| WO | WO 93/21950 A1 | 11/1993 |
| WO | WO 94/00153 A1 | 1/1994 |
| WO | WO 94/01772 A1 | 1/1994 |
| WO | WO 94/03208 A1 | 2/1994 |
| WO | WO 94/03615 A1 | 2/1994 |
| WO | WO 94/05311 A1 | 3/1994 |
| WO | WO 94/09364 A1 | 4/1994 |
| WO | WO 94/09823 A1 | 5/1994 |
| WO | WO 94/10569 A1 | 5/1994 |
| WO | WO 94/16731 A1 | 8/1994 |
| WO | WO 94/17197 A1 | 8/1994 |
| WO | WO 94/21288 A1 | 9/1994 |
| WO | WO 94/28412 A1 | 12/1994 |
| WO | WO 94/29459 A1 | 12/1994 |
| WO | WO 95/04151 A2 | 2/1995 |
| WO | WO 95/05393 A2 | 2/1995 |
| WO | WO 95/05849 A1 | 3/1995 |
| WO | WO 95/05853 A1 | 3/1995 |
| WO | WO 95/06407 A1 | 3/1995 |
| WO | WO 95/07301 A1 | 3/1995 |
| WO | WO 95/08999 A1 | 4/1995 |
| WO | WO 95/11008 A2 | 4/1995 |
| WO | WO 95/11311 A1 | 4/1995 |
| WO | WO 95/11994 A1 | 5/1995 |
| WO | WO 95/12815 A1 | 5/1995 |
| WO | WO 95/17085 A1 | 6/1995 |
| WO | WO 95/23166 A1 | 8/1995 |
| WO | WO 95/23860 A2 | 9/1995 |
| WO | WO 95/31996 A1 | 11/1995 |
| WO | WO 96/01126 A1 | 1/1996 |
| WO | WO 96/03144 A1 | 2/1996 |
| WO | WO 96/08565 A2 | 3/1996 |
| WO | WO 96/14061 A1 | 5/1996 |
| WO | WO 96/15799 A1 | 5/1996 |
| WO | WO 96/18900 A1 | 6/1996 |
| WO | WO 96/22373 A1 | 7/1996 |
| WO | WO 96/25435 A1 | 8/1996 |
| WO | WO 96/28471 A1 | 9/1996 |
| WO | WO 96/29421 A1 | 9/1996 |
| WO | WO 96/33739 A1 | 10/1996 |
| WO | WO 96/37621 A2 | 11/1996 |
| WO | WO 94/40895 A1 | 12/1996 |
| WO | WO 96/39176 A1 | 12/1996 |
| WO | WO 96/39834 A1 | 12/1996 |
| WO | WO 97/03192 A3 | 1/1997 |
| WO | WO 97/05164 A1 | 2/1997 |
| WO | WO 97/08320 A1 | 3/1997 |
| WO | WO 97/10505 A1 | 3/1997 |
| WO | 97/13855 | 4/1997 |
| WO | WO 97/17613 A1 | 5/1997 |
| WO | WO 97/18855 A1 | 5/1997 |
| WO | WO 97/21728 A1 | 6/1997 |
| WO | WO 97/36913 A1 | 7/1997 |
| WO | 9215492 | 8/1997 |
| WO | WO 97/28816 A1 | 8/1997 |
| WO | WO 97/32017 A1 | 9/1997 |
| WO | WO 97/36601 A1 | 10/1997 |
| WO | WO 97/37031 A1 | 10/1997 |
| WO | WO 97/40147 A1 | 10/1997 |
| WO | WO 98/02462 A1 | 1/1998 |
| WO | WO 98/04720 A1 | 2/1998 |
| WO | WO 98/05350 A1 | 2/1998 |
| WO | WO 98/07850 A2 | 2/1998 |
| WO | WO 98/08098 A1 | 2/1998 |
| WO | WO 98/08868 A1 | 3/1998 |
| WO | WO 98/22120 A1 | 5/1998 |
| WO | WO 98/33815 A1 | 8/1998 |
| WO | WO 98/39303 A1 | 9/1998 |
| WO | WO 98/44955 A1 | 10/1998 |
| WO | WO 98/56418 A1 | 12/1998 |
| WO | WO 99/00150 A2 | 1/1999 |
| WO | WO 99/06066 A2 | 2/1999 |
| WO | WO 99/06587 A2 | 2/1999 |
| WO | WO 99/10008 A1 | 3/1999 |
| WO | WO 99/27911 A1 | 6/1999 |
| WO | WO 99/27944 A1 | 6/1999 |
| WO | WO 99/27949 A1 | 6/1999 |
| WO | WO 99/06545 A2 | 11/1999 |
| WO | WO 99/58564 A1 | 11/1999 |
| WO | WO 99/60021 A2 | 11/1999 |
| WO | WO 99/60024 A1 | 11/1999 |
| WO | WO 00/20027 A2 | 4/2000 |
| WO | WO 00/23082 A1 | 4/2000 |
| WO | WO 00/26238 A2 | 5/2000 |
| WO | WO 00/43039 A1 | 7/2000 |
| WO | WO 00/43049 A1 | 7/2000 |
| WO | WO 00/68263 A2 | 11/2000 |
| WO | WO 00/72870 A1 | 12/2000 |
| WO | WO 00/72876 A2 | 12/2000 |
| WO | WO 00/72876 A3 | 12/2000 |
| WO | WO 00/72880 A2 | 12/2000 |
| WO | WO 00/72880 A3 | 12/2000 |
| WO | WO 00/77178 A1 | 12/2000 |
| WO | WO 01/05355 A2 | 1/2001 |
| WO | WO 01/10900 A2 | 2/2001 |
| WO | WO 01/18169 A3 | 3/2001 |
| WO | WO 01/39796 A2 | 6/2001 |
| WO | WO 01/42306 A2 | 6/2001 |
| WO | WO 01/62284 A2 | 8/2001 |
| WO | WO 01/62801 A2 | 8/2001 |
| WO | WO 01/77167 A2 | 10/2001 |
| WO | WO 01/78777 A2 | 10/2001 |
| WO | WO 01/90182 A2 | 11/2001 |
| WO | WO 02/03911 A2 | 1/2002 |
| WO | WO 02/21141 A2 | 3/2002 |
| WO | WO 02/34777 A1 | 5/2002 |
| WO | WO 02/34878 A2 | 5/2002 |
| WO | WO 02/046237 A2 | 6/2002 |
| WO | WO 02/060481 A1 | 8/2002 |
| WO | WO 02/088306 A2 | 11/2002 |
| WO | WO 02/088307 A2 | 11/2002 |
| WO | WO 02/096457 A2 | 12/2002 |
| WO | WO 02/096937 A2 | 12/2002 |
| WO | WO 03/009817 A2 | 2/2003 |
| WO | WO 03/015691 A2 | 2/2003 |
| WO | WO 03/016466 A2 | 2/2003 |
| WO | WO 03/016467 A2 | 2/2003 |
| WO | WO 03/016467 A3 | 2/2003 |
| WO | WO 03/020212 A2 | 3/2003 |
| WO | WO 03/039485 A2 | 5/2003 |
| WO | WO 03/051374 A2 | 6/2003 |
| WO | WO 03/072036 A2 | 9/2003 |
| WO | WO 03/072036 A3 | 9/2003 |
| WO | WO 03/074081 A1 | 9/2003 |
| WO | WO 03/077858 A2 | 9/2003 |
| WO | WO 03/077858 A3 | 9/2003 |
| WO | WO 03/104437 A2 | 12/2003 |
| WO | WO 03/105894 A1 | 12/2003 |
| WO | WO 2004/013172 A2 | 2/2004 |
| WO | WO 2004/013172 A3 | 2/2004 |
| WO | WO 2004/016282 A1 | 2/2004 |
| WO | WO 2004/031400 A2 | 4/2004 |
| WO | WO 2004/044204 A2 | 5/2004 |

(56) References Cited

FOREIGN PATENT DOCUMENTS

| | | | |
|---|---|---|---|
| WO | WO 2004/044204 A3 | 5/2004 |
| WO | WO 2004/055164 A2 | 7/2004 |
| WO | WO 2004/069182 A3 | 8/2004 |
| WO | WO 2004/071408 A2 | 8/2004 |
| WO | WO 2004/080419 A3 | 9/2004 |
| WO | WO 2004/108895 A2 | 12/2004 |
| WO | WO 2004/108895 A3 | 12/2004 |
| WO | WO 2005/014041 A2 | 2/2005 |
| WO | WO 2005/026211 A2 | 3/2005 |
| WO | WO 2005/026211 A3 | 3/2005 |
| WO | WO 2005/035753 A | 4/2005 |
| WO | WO 2005/058940 A2 | 6/2005 |
| WO | WO 2005/058941 A2 | 6/2005 |
| WO | WO 2005/090315 A1 | 9/2005 |
| WO | WO 2006/032653 A2 | 3/2006 |
| WO | WO 2006/042158 A | 4/2006 |
| WO | WO 2006/066049 A2 | 6/2006 |
| WO | WO 2006/066171 A1 | 6/2006 |
| WO | WO 2006/081587 A3 | 8/2006 |
| WO | WO 2006/083689 A2 | 8/2006 |
| WO | WO 2006/121656 A2 | 11/2006 |
| WO | WO 2008/011348 A2 | 1/2008 |
| WO | WO 2008/114801 A1 | 9/2008 |
| WO | WO 2008/131298 A2 | 10/2008 |
| WO | WO 2008/131298 A3 | 12/2008 |
| WO | WO 2009/017467 A1 | 2/2009 |
| WO | WO 2009/052439 A2 | 4/2009 |
| WO | WO 2010/033861 A1 | 3/2010 |
| WO | WO 2010/044803 A1 | 4/2010 |
| WO | WO 2011/106732 A1 | 9/2011 |
| WO | WO 2011/133919 A1 | 10/2011 |

OTHER PUBLICATIONS

Oh U et al. (2004) Reversible leukoencephalopathy associated with cerebral amyloid angiopathy. Neurology, 62:494-497.*
Sperling RA et al. (2011) Amyloid-related imaging abnormalities in amyloid-modifying therapeutic trials: Recommendations from the Alzheimer's Association Research Roundtable Workgroup. Alzheimer's & Dementia, 7:367-385.*
Servillo G et al. (2007) Posterior reversible encephalopathy syndrome in intensive care medicine. 33:230-236.*
Staykov D et al. (2012) Posterior reversible encephalopathy syndrome. J. Intensive Care Med. 27(1):11-24.*
U.S. Appl. No. 09/201,430, Office Action mailed May 10, 2000.
U.S. Appl. No. 09/201,430, Office Action mailed Dec. 21, 1999.
U.S. Appl. No. 09/204,838, Office Action mailed Mar. 17, 2000.
U.S. Appl. No. 09/322,289, Office Action mailed Sep. 29, 2000.
U.S. Appl. No. 09/497,553, Office Action mailed Oct. 3, 2003.
U.S. Appl. No. 09/580,015, Office Action mailed Feb. 11, 2002.
U.S. Appl. No. 09/580,018, Office Action mailed Mar. 12, 2002.
U.S. Appl. No. 09/580,019, Office Action mailed Mar. 12, 2002.
U.S. Appl. No. 09/723,544, Office Action mailed Sep. 23, 2002.
U.S. Appl. No. 09/723,760, Office Action mailed Mar. 12, 2002.
U.S. Appl. No. 09/723,765, Office Action mailed Mar. 12, 2002.
U.S. Appl. No. 09/723,766, Office Action mailed Mar. 5, 2002.
U.S. Appl. No. 09/723,766, Office Action mailed Jun. 11, 2002.
U.S. Appl. No. 09/724,273, Office Action mailed Jul. 2, 2002.
U.S. Appl. No. 09/724,273, Office Action mailed Nov. 8, 2005.
U.S. Appl. No. 09/724,288, Office Action mailed Mar. 12, 2002.
U.S. Appl. No. 09/724,288, Office Action mailed May 3, 2004.
U.S. Appl. No. 09/724,319, Office Action mailed Jul. 21, 2003.
U.S. Appl. No. 09/724,495, Office Action mailed Mar. 13, 2003.
U.S. Appl. No. 09/724,495, Office Action mailed Sep. 24, 2002.
U.S. Appl. No. 09/724,551, Office Action mailed Jul. 2, 2002.
U.S. Appl. No. 09/724,552, Office Action mailed May 6, 2002.
U.S. Appl. No. 09/724,567, Office Action mailed Mar. 27, 2002.
U.S. Appl. No. 09/724,575, Office Action mailed Mar. 27, 2002.
U.S. Appl. No. 09/724,921, Office Action mailed Apr. 30, 2002.
U.S. Appl. No. 09/724,929, Office Action mailed Mar. 22, 2002.
U.S. Appl. No. 09/724,940, Office Action mailed Mar. 13, 2003.
U.S. Appl. No. 09/724,953, Office Action mailed Mar. 26, 2002.
U.S. Appl. No. 09/724,961, Office Action mailed Mar. 12, 2002.
U.S. Appl. No. 09/979701, Office Action mailed Feb. 15, 2005.
U.S. Appl. No. 09/979,701, Office Action mailed Sep. 15, 2005.
U.S. Appl. No. 09/979,952, Office Action mailed Aug. 7, 2003.
U.S. Appl. No. 09/980,568, Office Action mailed May 29, 2003.
U.S. Appl. No. 10/010,942, Office Action mailed Sep. 24, 2003.
U.S. Appl. No. 10/232,030, Office Action mailed Dec. 2, 2004.
U.S. Appl. No. 10/388,214, Office Action mailed May 31, 2005.
U.S. Appl. No. 10/388,389, Office Action mailed Nov. 22, 2005.
U.S. Appl. No. 10/429,216, Office Action mailed Dec. 28, 2005.
U.S. Appl. No. 10/544,093, Office Action, mailed Jun. 16, 2008.
U.S. Appl. No. 10/625,854, Office Action mailed Nov. 10, 2005.
U.S. Appl. No. 10/703,713, Office Action mailed Nov. 5, 2004.
U.S. Appl. No. 10/704,070, Office Action mailed Nov. 5, 2004.
U.S. Appl. No. 10/771,174, Office Action mailed Sep. 14, 2006.
U.S. Appl. No. 10/777,792, Office Action mailed Mar. 2, 2006.
U.S. Appl. No. 10/788,666, Office Action mailed Jan. 12, 2005.
U.S. Appl. No. 10/789,273, Office Action mailed Sep. 22, 2006.
U.S. Appl. No. 10/822,968, Office Action mailed Mar. 22, 2006.
U.S. Appl. No. 10/823,463, Office Action mailed Feb. 4, 2005.
U.S. Appl. No. 10/828,548, Office Action mailed Feb. 4, 2005.
U.S. Appl. No. 10/828,548, Office Action mailed Sep. 29, 2005.
U.S. Appl. No. 10/858,855, Office Action mailed Jun. 22, 2006.
U.S. Appl. No. 10/923,267, Office Action mailed Jul. 21, 2006.
U.S. Appl. No. 10/923,469, Office Action mailed Mar. 29, 2007.
U.S. Appl. No. 10/923,474, Office Action mailed Feb. 15, 2005.
U.S. Appl. No. 10/928,926, Office Action mailed Jan. 12, 2007.
U.S. Appl. No. 10/934,819, Office Action mailed Oct. 14, 2005.
U.S. Appl. No. 11/058,757, Office Action mailed May 3, 2005.
U.S. Appl. No. 11/058,757, Office Action mailed Aug. 24, 2005.
U.S. Appl. No. 11/244,678, Office Action mailed Apr. 18, 2007.
U.S. Appl. No. 11/245,524, Office Action mailed May 15, 2007.
U.S. Appl. No. 11/245,916, Office Action mailed Jan. 13, 2006.
U.S. Appl. No. 11/260,047, Office Action mailed Oct. 26, 2006.
U.S. Appl. No. 11/303,478, Office Action mailed Apr. 1, 2008.
U.S. Appl. No. 11/303,478, Office Action mailed Oct. 16, 2008.
U.S. Appl. No. 11/304,072, Office Action mailed Dec. 26, 2006.
U.S. Appl. No. 11/304,986, Office Action mailed Jan. 2, 2008.
U.S. Appl. No. 11/305,889, Office Action mailed May 4, 2007.
U.S. Appl. No. 11/305,889, Office Action mailed Jul. 25, 2008.
U.S. Appl. No. 11/305,899, Office Action mailed Apr. 4, 2008.
U.S. Appl. No. 11/342,353, Office Action mailed Mar. 26, 2008.
U.S. Appl. No. 11/342,353, Office Action mailed Jul. 9, 2008.
U.S. Appl. No. 11/454,772, Office Action mailed Feb. 27, 2007.
U.S. Appl. No. 11/516,724, Office Action mailed Jan. 27, 2009.
U.S. Appl. No. 11/520,438, Office Action mailed Apr. 2, 2009.
U.S. Appl. No. 11/707,639 Office Action mailed Apr. 3, 2009.
U.S. Appl. No. 11/842,085, Office Action mailed Apr. 14, 2009.
U.S. Appl. No. 11/842,113, Office Action mailed Dec. 17, 2009.
U.S. Appl. No. 11/842,116, Office Action mailed Mar. 31, 2010.
U.S. Appl. No. 11/842,120, Office Action mailed Apr. 14, 2009.
U.S. Appl. No. 12/106,206, Office Action mailed Feb. 5, 2010.
U.S. Appl. No. 12/253,929, Office Action mailed Jan. 25, 2010.
U.S. Appl. No. 12/328,740, Office Action mailed Oct. 9, 2009.
U.S. Appl. No. 09/723,765, Office Action mailed Dec. 3, 2002.
U.S. Appl. No. 09/723,766, Office Action mailed Nov. 1, 2002.
U.S. Appl. No. 09/724,552, Office Action mailed Jun. 3, 2003.
U.S. Appl. No. 09/724,567, Office Action mailed Nov. 15, 2002.
U.S. Appl. No. 09/724,575, Examiner Interview Summary mailed May 6, 2005.
U.S. Appl. No. 09/724,575, Office Action mailed Nov. 21, 2002.
U.S. Appl. No. 09/979,952, Office Action mailed Dec. 30, 2003.
U.S. Appl. No. 09/980,568, Office Action mailed Feb. 23, 2004.
U.S. Appl. No. 11/108,102, Office Action mailed Jan. 11, 2006.
U.S. Appl. No. 09/201,430, Examiner Interview Summary mailed May 30, 2001.
U.S. Appl. No. 09/201,430, Office Action mailed Jan. 17, 2001.
U.S. Appl. No. 09/204,838, Office Action mailed Dec. 21, 2000.
U.S. Appl. No. 09/322,289, Examiner Interview Summary mailed Jun. 27, 2006.
U.S. Appl. No. 09/322,289, Examiner Interview Summary mailed Jan. 15, 2009.
U.S. Appl. No. 09/322,289, Office Action mailed Jun. 19, 2001.

(56) References Cited

OTHER PUBLICATIONS

U.S. Appl. No. 09/497,553, Office Action mailed Nov. 29, 2005.
U.S. Appl. No. 09/580,018, Office Action mailed May 20, 2003.
U.S. Appl. No. 09/723,384, Examiner Interview Summary mailed Mar. 28, 2003.
U.S. Appl. No. 09/723,384, Office Action mailed Oct. 9, 2002.
U.S. Appl. No. 09/723,544, Office Action mailed Aug. 11, 2003.
U.S. Appl. No. 09/723,713, Office Action mailed Mar. 26, 2002.
U.S. Appl. No. 09/723,760, Office Action mailed Dec. 19, 2002.
U.S. Appl. No. 09/723,762, Office Action mailed Oct. 2, 2001.
U.S. Appl. No. 09/723,765, Examiner Interview Summary mailed Mar. 18, 2003.
U.S. Appl. No. 09/723,765, Examiner Interview Summary mailed Jan. 25, 2006.
U.S. Appl. No. 09/723,765, Examiner Interview Summary mailed Oct. 8, 2008.
U.S. Appl. No. 09/723,765, Examiner Interview Summary mailed Jan. 16, 2009.
U.S. Appl. No. 09/724,102, Office Action mailed Oct. 3, 2001.
U.S. Appl. No. 09/724,273, Office Action mailed Apr. 21, 2003.
U.S. Appl. No. 09/724,288, Office Action mailed Dec. 11, 2002.
U.S. Appl. No. 09/724,319, Examiner Interview Summary mailed Jul. 19, 2004.
U.S. Appl. No. 09/724,319, Examiner Interview Summary mailed Apr. 9, 2008.
U.S. Appl. No. 09/724,319, Office Action mailed Apr. 26, 2004.
U.S. Appl. No. 09/724,477, Office Action mailed Oct. 2, 2001.
U.S. Appl. No. 09/724,489, Office Action mailed Oct. 2, 2002.
U.S. Appl. No. 09/724,495, Office Action mailed Jan. 16, 2004.
U.S. Appl. No. 09/724,551, Office Action mailed Jun. 3, 2003.
U.S. Appl. No. 09/724,552, Examiner Interview Summary mailed Dec. 3, 2003.
U.S. Appl. No. 09/724,921, Office Action mailed Jan. 28, 2003.
U.S. Appl. No. 09/724,929, Office Action mailed Jul. 22, 2003.
U.S. Appl. No. 09/724,940, Office Action mailed Dec. 24, 2003.
U.S. Appl. No. 09/724,953, Office Action mailed Nov. 27, 2002.
U.S. Appl. No. 09/724,961 Office Action mailed May 16, 2003.
U.S. Appl. No. 09/724,961, Examiner Interview Summary mailed Dec. 3, 2003.
U.S. Appl. No. 09/979,701, Office Action mailed Jan. 10, 2006.
U.S. Appl. No. 10/010,942 ,Examiner Interview Summary mailed May 10, 2006.
U.S. Appl. No. 10/010,942 ,Examiner Interview Summary mailed May 11, 2006.
U.S. Appl. No. 10/010,942, Examiner Interview Summary mailed Nov. 18, 2004.
U.S. Appl. No. 10/010,942, Examiner Interview Summary mailed Feb. 22, 2006.
U.S. Appl. No. 10/010,942, Examiner Interview Summary mailed May 11, 2006.
U.S. Appl. No. 10/010,942, Examiner Interview Summary mailed Jan. 19, 2005.
U.S. Appl. No. 10/010,942, Office Action mailed May 26, 2004.
U.S. Appl. No. 10/232,030, Examiner Interview Summary mailed Feb. 17, 2006.
U.S. Appl. No. 10/232,030, Office Action mailed Oct. 14, 2005.
U.S. Appl. No. 10/388,214, Examiner Interview Summary mailed Oct. 2, 2006.
U.S. Appl. No. 10/388,214, Examiner Interview Summary mailed Nov. 6, 2006.
U.S. Appl. No. 10/388,214, Office Action mailed Jan. 31, 2006.
U.S. Appl. No. 10/388,389, Examiner Interview Summary mailed May 31, 2006.
U.S. Appl. No. 10/388,389, Examiner Interveiw Summary mailed May 22, 2006.
U.S. Appl. No. 10/429,216, Examiner Interview Summary mailed Mar. 6, 2006.
U.S. Appl. No. 10/429,216, Office Action mailed Apr. 11, 2006.
U.S. Appl. No. 10/544,093, Office Action mailed Feb. 9, 2009.
U.S. Appl. No. 10/625,854, Examiner Interview Summary mailed Jun. 26, 2007.
U.S. Appl. No. 10/625,854, Office Action mailed Feb. 7, 2006.
U.S. Appl. No. 10/703,713, Examiner Interview Summary mailed Feb. 21, 2006.
U.S. Appl. No. 10/703,713, Examiner Interview Summary mailed Mar. 2, 2006.
U.S. Appl. No. 10/703,713, Office Action mailed Sep. 27, 2005.
U.S. Appl. No. 10/704,070, Office Action mailed Sep. 26, 2005.
U.S. Appl. No. 10/771,174, Office Action mailed Nov. 27, 2006.
U.S. Appl. No. 10/777,792, Office Action mailed Aug. 7, 2006.
U.S. Appl. No. 10/788,666, Office Action mailed Dec. 15, 2005.
U.S. Appl. No. 10/823,463, Office Action mailed Sep. 30, 2005.
U.S. Appl. No. 10/828,548, Office Action mailed Feb. 13, 2006.
U.S. Appl. No. 10/858,855, Office Action mailed Mar. 7, 2007.
U.S. Appl. No. 10/889,999, Office Action mailed Jan. 5, 2005.
U.S. Appl. No. 10/890,000, Office Action mailed Apr. 13, 2005.
U.S. Appl. No. 10/890,024, Office Action mailed Nov. 2, 2005.
U.S. Appl. No. 10/890,070, Office Action mailed Apr. 8, 2005.
U.S. Appl. No. 10/890,071, Office Action mailed Dec. 18, 2006.
U.S. Appl. No. 10/923,469, Examiner Interview Summary mailed Apr. 9, 2008.
U.S. Appl. No. 10/923,469, Office Action mailed Jul. 3, 2007.
U.S. Appl. No. 10/923,471, Examiner Interview Summary mailed Oct. 20, 2008.
U.S. Appl. No. 10/923,471, Office Action mailed Jan. 5, 2005.
U.S. Appl. No. 10/923,474 Office Action mailed Nov. 17, 2005.
U.S. Appl. No. 10/923,605, Office Action mailed Apr. 12, 2007.
U.S. Appl. No. 10/934,818, Office Action mailed Mar. 26, 2007.
U.S. Appl. No. 10/934,819, Office Action mailed Jan. 24, 2006.
U.S. Appl. No. 11/058,757, Office Action mailed Oct. 20, 2005.
U.S. Appl. No. 11/244,678, Office Action mailed Jul. 13, 2007.
U.S. Appl. No. 11/245,524, Office Action mailed Sep. 27, 2007.
U.S. Appl. No. 11/245,916, Office Action mailed May 19, 2006.
U.S. Appl. No. 11/260,047, Office Action mailed May 15, 2007.
U.S. Appl. No. 11/260,047, Examiner Interview Summary mailed May 15, 2007.
U.S. Appl. No. 11/274,493, Office Action mailed Apr. 23, 2007.
U.S. Appl. No. 11/303,478, Office Action mailed Mar. 18, 2009.
U.S. Appl. No. 11/304,986, Office Action mailed Dec. 31, 2008.
U.S. Appl. No. 11/305,889, Office Action mailed Aug. 14, 2007.
U.S. Appl. No. 11/305,899, Office Action mailed Dec. 10, 2008.
U.S. Appl. No. 11/342,353, Office Action mailed Nov. 14, 2008.
U.S. Appl. No. 11/454,772, Office Action mailed Jun. 27, 2007.
U.S. Appl. No. 11/45772, Examiner Interview Summary mailed Apr. 13, 2007.
U.S. Appl. No. 11/520,438, Office Action mailed Aug. 6, 2009.
U.S. Appl. No. 11/842,023, Office Action mailed Nov. 13, 2008.
U.S. Appl. No. 11/842,042, Office Action mailed Jun. 24, 2009.
U.S. Appl. No. 11/842,056, Office Action mailed May 6, 2009.
U.S. Appl. No. 11/842,085, Office Action mailed Sep. 30, 2009.
U.S. Appl. No. 11/842,116, Office Action mailed Nov. 26, 2010.
U.S. Appl. No. 12/037,045, Office Action mailed Apr. 28, 2010.
U.S. Appl. No. 12/181,238, Examiner Interview Summary mailed Mar. 5, 2010.
U.S. Appl. No. 12/181,238, Office Action mailed May 28, 2009.
U.S. Appl. No. 12/253,929, Office Action mailed Apr. 28, 2010.
U.S. Appl. No. 12/336,340, Office Action mailed Mar. 4, 2010.
U.S. Appl. No. 09/724,319, Office Action mailed May 16, 2007.
U.S. Appl. No. 09/201,430, Office Action mailed Oct. 1, 2002.
U.S. Appl. No. 09/204,838, Office Action mailed Apr. 18, 2003.
U.S. Appl. No. 09/322,289, Office Action mailed Feb. 7, 2008.
U.S. Appl. No. 09/322,289, Office Action mailed Feb. 24, 2005.
U.S. Appl. No. 09/322,289, Office Action mailed Nov. 4, 2008.
U.S. Appl. No. 09/322,289, Office Action mailed Nov. 17, 2006.
U.S. Appl. No. 09/723,713, Office Action mailed Apr. 19, 2005.
U.S. Appl. No. 09/723,713, Office Action mailed Oct. 24, 2003.
U.S. Appl. No. 09/723,725, Office Action mailed Dec. 9, 2002.
U.S. Appl. No. 09/723,765, Office Action mailed May 22, 2008.
U.S. Appl. No. 09/723,765, Office Action mailed Aug. 10, 2004.
U.S. Appl. No. 09/724,273, Office Action mailed Jun. 8, 2006.
U.S. Appl. No. 09/724,273, Office Action mailed Jun. 22, 2004.
U.S. Appl. No. 09/724,273, Office Action mailed Dec. 22, 2006.

(56) References Cited

OTHER PUBLICATIONS

U.S. Appl. No. 09/724,288, Office Action mailed Mar. 18, 2008.
U.S. Appl. No. 09/724,288, Office Action mailed Apr. 23, 2007.
U.S. Appl. No. 09/724,288, Office Action mailed Jun. 21, 2006.
U.S. Appl. No. 09/724,288, Office Action mailed Oct. 3, 2007.
U.S. Appl. No. 09/724,288, Office Action mailed Dec. 14, 2004.
U.S. Appl. No. 09/724,319, Office Action mailed Aug. 15, 2005.
U.S. Appl. No. 09/724,575, Office Action mailed Mar. 31, 2006.
U.S. Appl. No. 09/724,575, Office Action mailed May 6, 2005.
U.S. Appl. No. 09/724,575, Office Action mailed Oct. 17, 2005.
U.S. Appl. No. 09/980,568, Office Action mailed Nov. 2, 2004.
U.S. Appl. No. 10/232,030, Office Action mailed Jun. 15, 2007.
U.S. Appl. No. 10/429,216, Office Action mailed Jan. 28, 2008.
U.S. Appl. No. 10/429,216, Office Action mailed Mar. 12, 2010.
U.S. Appl. No. 10/429,216, Office Action mailed Sep. 15, 2010.
U.S. Appl. No. 10/544,093, Office Action mailed Jan. 22, 2010.
U.S. Appl. No. 10/625,854, Office Action mailed May 15, 2007.
U.S. Appl. No. 10/777,792, Office Action mailed Apr. 3, 2008.
U.S. Appl. No. 10/828,548, Office Action mailed Sep. 11, 2007.
U.S. Appl. No. 10/858,855 Office Action mailed Dec. 12, 2008.
U.S. Appl. No. 10/858,855 Office Action mailed Dec. 15, 2009.
U.S. Appl. No. 10/889,999, Office Action mailed Aug. 15, 2005.
U.S. Appl. No. 10/890,000, Office Action mailed Mar. 10, 2006.
U.S. Appl. No. 10/890,000, Office Action mailed Sep. 19, 2005.
U.S. Appl. No. 10/890,070, Office Action mailed Sep. 29, 2005.
U.S. Appl. No. 10/923,469, Office Action mailed Mar. 24, 2008.
U.S. Appl. No. 10/923,471, Office Action mailed Mar. 20, 2009.
U.S. Appl. No. 10/923,471, Office Action mailed May 15, 2006.
U.S. Appl. No. 10/923,471, Office Action mailed Jul. 31, 2007.
U.S. Appl. No. 10/923,471, Office Action mailed Aug. 24, 2005.
U.S. Appl. No. 10/923,474 Office Action mailed Jun. 26, 2007.
U.S. Appl. No. 11/244,678, Office Action mailed Sep. 23, 2008.
U.S. Appl. No. 11/245,524, Office Action mailed Apr. 17, 2009.
U.S. Appl. No. 11/245,524, Office Action mailed Jun. 4, 2008.
U.S. Appl. No. 11/245,524, Office Action mailed Dec. 10, 2010.
U.S. Appl. No. 11/245,916, Office Action mailed Jan. 28, 2008.
U.S. Appl. No. 11/245,916, Office Action mailed May 18, 2010.
U.S. Appl. No. 11/245,916, Office Action mailed Oct. 31, 2008.
U.S. Appl. No. 11/245,916, Office Action mailed Dec. 14, 2011.
U.S. Appl. No. 11/342,353, Office Action mailed Jul. 22, 2008.
U.S. Appl. No. 11/842,023, Office Action mailed Aug. 14, 2009.
U.S. Appl. No. 111/842113, Office Action mailed Aug. 24, 2010.
U.S. Appl. No. 09/723,760, Office Action mailed May 4, 2005.
U.S. Appl. No. 09/724,319, Office Action mailed Jan. 11, 2008.
U.S. Appl. No. 10/010,942, Office Action mailed Jan. 19, 2005.
U.S. Appl. No. 10/010,942, Office Action mailed Oct. 3, 2005.
U.S. Appl. No. 10/703,713, Office Action mailed Jun. 2, 2006.
U.S. Appl. No. 09/201,430, Advisory Action mailed Jun. 18, 2002.
U.S. Appl. No. 09/201,430, Office Action mailed Nov. 26, 2001.
U.S. Appl. No. 09/204,838, Office Action mailed Sep. 27, 2001.
U.S. Appl. No. 09/322,289, Office Action mailed Jun. 4, 2009.
U.S. Appl. No. 09/322,289, Office Action mailed Jul. 17, 2007.
U.S. Appl. No. 09/322,289, Office Action mailed Oct. 16, 2005.
U.S. Appl. No. 09/322,289, Office Action mailed Nov. 29, 2005.
U.S. Appl. No. 09/723,713, Advisory Action mailed Dec. 20, 2004.
U.S. Appl. No. 09/723,713, Office Action mailed Jan. 11, 2006.
U.S. Appl. No. 09/723,713, Office Action mailed Feb. 12, 2002.
U.S. Appl. No. 09/723,713, Office Action mailed Jun. 3, 2004.
U.S. Appl. No. 09/723,760, Advisory Action mailed Dec. 16, 2004.
U.S. Appl. No. 09/723,760, Office Action mailed Feb. 23, 2004.
U.S. Appl. No. 09/723,760, Office Action mailed Dec. 29, 2005.
U.S. Appl. No. 09/723,765, Advisory Action mailed Feb. 9, 2004.
U.S. Appl. No. 09/723,765, Office Action mailed May 4, 2005.
U.S. Appl. No. 09/723,765, Office Action mailed Oct. 7, 2003.
U.S. Appl. No. 09/723,765, Office Action mailed Dec. 5, 2008.
U.S. Appl. No. 09/724,273, Advisory Action mailed Mar. 18, 2004.
U.S. Appl. No. 09/724,273, Advisory Action mailed Jun. 16, 2005.
U.S. Appl. No. 09/724,273, Office Action mailed Aug. 22, 2007.
U.S. Appl. No. 09/724,273, Office Action mailed Oct. 16, 2003.
U.S. Appl.n No. 09/724,273, Office Action mailed Dec. 28, 2004.
U.S. Appl. No. 09/724,288, Advisory Action mailed Jan. 6, 2004.
U.S. Appl. No. 09/724,288, Advisory Action mailed Mar. 3, 2006.
U.S. Appl. No. 09/724,288, Office Action mailed Jul. 12, 2005.
U.S. Appl. No. 09/724,288, Office Action mailed Sep. 9, 2003.
U.S. Appli. No. 09/724,288, Office Action mailed Dec. 22, 2008.
U.S. Appl. No. 09/724,319 Advisory Action mailed Oct. 28, 2009.
U.S. Appl. No. 09/724,319 Office Action mailed Apr. 8, 2009.
U.S. Appl. No. 09/724,319 Office Action mailed May 2, 2006.
U.S. Appl. No. 09/724,319 Office Action mailed Dec. 21, 2010.
U.S. Appl. No. 09/724,495, Advisory Action mailed May 16, 2004.
U.S. Appl. No. 09/724,495, Office Action mailed Sep. 26, 2005.
U.S. Appl. No. 09/724,567, Office Action mailed Jul. 23, 2003.
U.S. Appl. No. 09/724,575, Advisory Action mailed Feb. 12, 2004.
U.S. Appl. No. 09/724,575, Office Action mailed Jul. 25, 2003.
U.S. Appl. No. 09/724,575, Office Action mailed Oct. 12, 2006.
U.S. Appl. No. 09/724,953, Office Action mailed Jul. 25, 2003.
U.S. Appl. No. 10/232,030, Advisory Action mailed Oct. 30, 2006.
U.S. Appl. No. 10/232,030, Office Action mailed Apr. 1, 2008.
U.S. Appl. No. 10/388,214, Office Action mailed Jul. 28, 2006.
U.S. Appl. No. 10/429,216, Office Action mailed Jan. 3, 2007.
U.S. Appl. No. 10/429,216, Office Action mailed Mar. 6, 2009.
U.S. Appl. No. 10/429,216, Office Action mailed Oct. 16, 2008.
U.S. Appl. No. 10/544,093, Office Action mailed Oct. 13, 2010.
U.S. Appl. No. 10/625,854, Advisory Action mailed Jan. 8, 2008.
U.S. Appl. No. 10/625,854, Office Action mailed Aug. 23, 2006.
U.S. Appl. No. 10/625,854, Office Action mailed Nov. 7, 2007.
U.S. Appl. No. 10/704,070, Office Action mailed Jun. 6, 2006.
U.S. Appl. No. 10/771,174, Office Action mailed Aug. 23, 2007.
U.S. Appl. No. 10/777,792, Advisory Action mailed Nov. 30, 2010.
U.S. Appl. No. 10/777,792, Office Action mailed May 8, 2007.
U.S. Appl. No. 10/777,792, Office Action mailed Nov. 18, 2008.
U.S. Appl. No. 10/828,548, Advisory Action mailed Jun. 8, 2007.
U.S. Appl. No. 10/828,548, Office Action mailed Jun. 4, 2008.
U.S. Appl. No. 10/828,548, Office Action mailed Oct. 24, 2006.
U.S. Appl. No. 10/858,855, Advisory Action mailed Apr. 7, 2008.
U.S. Appl. No. 10/858,855, Office Action mailed Nov. 23, 2007.
U.S. Appl. No. 10/889,999, Office Action mailed Mar. 14, 2006.
U.S. Appl. No. 10/890,000, Advisory Action mailed Jan. 14, 2008.
U.S. Appl. No. 10/890,000, Office Action mailed Nov. 24, 2006.
U.S. Appl. No. 10/890,024, Office Action mailed Jun. 1, 2006.
U.S. Appl. No. 10/890,070, Office Action mailed Jun. 1, 2006.
U.S. Appl. No. 10/923,469. Advisory Action mailed Apr. 16, 2009.
U.S. Appl. No. 10/923,469. Office Action mailed Dec. 29, 2008.
U.S. Appl. No. 10/923,471, Office Action mailed Apr. 24, 2008.
U.S. Appl. No. 10/923,471, Office Action mailed Dec. 24, 2009.
U.S. Appl. No. 10/923,471, Office Action mailed Dec. 29, 2006.
U.S. Appl. No. 10/923,474 Office Action mailed Aug. 4, 2006.
U.S. Appl. No. 10/923,474, Advisory Action mailed Feb. 22, 2007.
U.S. Appl. No. 11/058,757, Advisory Action mailed Mar. 5, 2007.
U.S. Appl. No. 11/058,757, Office Action mailed Aug. 11, 2006.
U.S. Appl. No. 11/108,102, Office Action mailed Sep. 6, 2006.
U.S. Appl. No. 11/244,678, Office Action mailed Mar. 24, 2008.
U.S. Appl. No. 11/245,524, Office Action mailed Nov. 20, 2009.
U.S. Appl. No. 11/245,916, Advisory Action mailed May 15, 2007.
U.S. Appl. No. 11/245,916, Advisory Action mailed Jun. 10, 2009.
U.S. Appl. No. 11/245,916, Advisory Action mailed Oct. 18, 2007.
U.S. Appl. No. 11/245,916, Office Action mailed Jan. 12, 2007.
U.S. Appl. No. 11/274,493, Office Action mailed Nov. 2, 2007.
U.S. Appl. No. 11/305,889, Office Action mailed May 23, 2008.
U.S. Appl. No. 11/454,772, Office Action mailed Dec. 21, 2007.
U.S. Appl. No. 11/842,042, Office Action mailed Mar. 30, 2010.
U.S. Appl. No. 09/201,430, Notice of Allowance mailed Mar. 26, 2003.
U.S. Appl. No. 09/201,430, Notice of Allowance mailed Sep. 23, 2003.
U.S. Appl. No. 09/322,289, Notice of Allowance mailed Nov. 15, 2010.
U.S. Appl. No. 09/580,018, Notice of Allowance mailed Dec. 3, 2003.
U.S. Appl. No. 09/723,384, Notice of Allowance mailed Mar. 31, 2003.
U.S. Appl. No. 09/723,762, Notice of Allowance mailed May 1, 2003.

(56) References Cited

OTHER PUBLICATIONS

U.S. Appl. No. 09/723,927, Notice of Allowance mailed Sep. 23, 2003.
U.S. Appl. No. 09/724,102, Notice of Allowance mailed Aug. 22, 2003.
U.S. Appl. No. 09/724,288, Notice of Allowance mailed Mar. 23, 2009.
U.S. Appl. No. 09/724,477, Notice of Allowance mailed Apr. 30, 2003.
U.S. Appl. No. 09/724,477, Notice of Allowance mailed Sep. 23, 2003.
U.S. Appl. No. 09/724,489, Notice of Allowance mailed Mar. 25, 2003.
U.S. Appl. No. 09/724,489, Notice of Allowance mailed Sep. 22, 2003.
U.S. Appl. No. 09/724,551, Notice of Allowance mailed Dec. 4, 2003.
U.S. Appl. No. 09/724,552, Notice of Allowance mailed Dec. 3, 2003.
U.S. Appl. No. 09/724,567, Notice of Allowance mailed Mar. 3, 2004.
U.S. Appl. No. 09/724,940, Notice of Allowance mailed Oct. 4, 2004.
U.S. Appl. No. 09/724,953, Notice of Allowance mailed Mar. 11, 2004.
U.S. Appl. No. 09/724,961, Notice of Allowance mailed Dec. 3, 2003.
U.S. Appl. No. 09/979,952, Notice of Allowance mailed Nov. 12, 2004.
U.S. Appl. No. 10/010,942, Notice of Allowance mailed May 11, 2006.
U.S. Appl. No. 10/232,030, Notice of Allowance mailed Sep. 4, 2008.
U.S. Appl. No. 10/388,214, Notice of Allowance mailed Mar. 1, 2007.
U.S. Appl. No. 10/388,389, Notice of Allowance mailed May 31, 2006.
U.S. Appl. No. 10/815,353, Notice of Allowance mailed Jul. 1, 2004.
U.S. Appl. No. 10/815,391, Notice of Allowance mailed Jul. 1, 2004.
U.S. Appl. No. 10/815,404, Notice of Allowance mailed Oct. 15, 2004.
U.S. Appl. No. 10/816,022, Notice of Allowance mailed Jul. 1, 2004.
U.S. Appl. No. 10/816,380, Notice of Allowance mailed Dec. 22, 2004.
U.S. Appl. No. 10/816,529, Notice of Allowance mailed Jul. 1, 2004.
U.S. Appl. No. 10/858,855, Notice of Allowance mailed Jul. 12, 2010.
U.S. Appl. No. 10/884,892, Notice of Allowance mailed Mar. 28, 2005.
U.S. Appl. No. 10/933,559, Notice of Allowance mailed Aug. 17, 2005.
U.S. Appl. No. 10/933,559, Notice of Allowance mailed Sep. 7, 2005.
U.S. Appl. No. 10/933,559, Notice of Allowance mailed Dec. 22, 2004.
U.S. Appl. No. 10/934,609, Notice of Allowance mailed Aug. 17, 2005.
U.S. Appl. No. 10/934,609, Notice of Allowance mailed Dec. 22, 2004.
U.S. Appl. No. 11/304,986, Notice of Allowance mailed Jul. 10, 2009.
U.S. Appl. No. 11/707,639, Notice of Allowance mailed Aug. 20, 2009.
U.S. Appl. No. 11/842,023, Notice of Allowance mailed Oct. 6, 2010.
U.S. Appl. No. 12/181,238, Notice of Allowance mailed Mar. 5, 2010.
U.S. Appl. No. 09/723,765, BPAI Decision on Request for Re-hearing mailed Oct. 16, 2007.
U.S. Appl. No. 09/723,765, BPAI Order Returning Appeal to Examiner mailed Jun. 27, 2006.
U.S. Appl. No. 09/723,765, Examiners Answer mailed Jan. 25, 2006.
U.S. Appl. No. 09/723,765, Reply Brief Noted mailed Jun. 16, 2006.
U.S. Appl. No. 10/777,792, BPAI Decision mailed Aug. 30, 2010.
U.S. Appl. No. 10/777,792, Decision on Request for Reconsideration mailed Nov. 30, 2010.
U.S. Appl. No. 10/777,792, Examiners Answer mailed Oct. 27, 2009.
U.S. Appl. No. 10/777,792, Reply Brief Noted mailed Jan. 11, 2010.
U.S. Appl. No. 10/923,469, BPAI Decision mailed Feb. 22, 2011.
U.S. Appl. No. 10/923,469, Reply Brief Noted mailed Mar. 9, 2010.
U.S. Appl. No. 60/530,480, filed Dec. 17, 2003, Arumugham.
Agadjanyan et al., "Prototype Alzheimer's Disease Vaccine Using the Immunodominant B Cell Epitope From {beta}-Amyloid and Promiscuous T Cell Epitope Pan HLA DR-Binding Peptide," *J. Immunol.*, 174:1580-1586 (2005).
Allen et al, "Reversible posterior leukoencephalopathy syndrome after bevacizumab/FOLFIRI Regimen for Metastatic Colon Caner," Arch. Neurol., 63(10): 1475-1478 (2006), abstract only.
Aquila Press Release, PR Newswire. May 6, 1997.
Armour et al., "Recombinant human IgG molecules lacking Fcγ receptor I binding and monocyte triggering activites," *J. Immunol*, 29:2613-2624 (1999).
Auclair et al., "Effect of Active Immunization Against Oestriadiol in Developing Ram Lambs on Plasma Gonadotrophin and Testosterone Concentrations, Time of Onset of Puberty and Testicular Blood Flow," *Journal of Reproduction and Fertility*, 104:7-16 (1995).
Aylward et al., "Cerebellar Volume in Adults With Down Syndrome," *Arch Neurol.*, 4(2):209-212 (1997). Abstract only.
Bach et al., "Vaccination with AB-Displaying Virus-Like Particles Reduces Soluble and Insoluble Cerebral AB and Lowers Plaque Burden in APP Transgenic Mice," J. Immunol., 2009, 182 7613-7624.
Bandlow et al., "Untersuchungen Zum Mechanismus Der Immunologischen Adjvanswirung des Vacciniavirus,"*Archiv für due qesamte Virusfoschung*, 38:192-204 (1972). German article.
Barelli et al., "Characterization of New Polyclonal Antibodies Specific for 40 and 42 Amino Acid-Long Amyloid β Peptides: Their Use to Examine the Cell Biology of Presenilins and the Immunohistochemistry of Sporadic Alzheimer's Disease and Cerebral Amyloid Angiopathy Cases," Molecular Medicine, 3(10):695-707 (1997).
Begley, "Delivery of Therapeutic Agents to the Central Nervouse System: The Problems and the Possibilities," *Pharmacol. Therapy*, 104(1): 29-45 (Oct. 2004).
Biewenga et al., "Cleavage of Protein A-binding IgA1 with IgA1 Protease From *Streptococcus* Sanguls," *Immunol Commun.*, 12(5):491-500 (1983), abstract only.
Black et al., "A Single Ascending Dose Study of Bainezumab, a Humanized Monoclonal Antibody to Aβ, In AD," *9th International Geneva/Springfield Symposium on Advances in Alzheimer Therapy*, 1 page (Apr. 20, 2006). Abstract only.
Boraschi et al., "Interleukin-1 and Interleukin-1 Fragments a Vaccine Adjuvants", Methods, 1999, 19, pp. 108-113.
Borras-Cuesta et al., "Engineering of Immunogenic Peptides by Co-Linear Synthesis of Determinants Recognized by B and T Cells," Eur. J. Immunol., 17:1213-1215 (1987).
Brinkman, "Splice Variants as Cancer Biomarkers," *Clinical Biochemisrty*, 37(7):584-594 (2004).
Burbach et al. "Vessel ultrastructure in APP23 transgenic mice after passive anti-Aβ immunotherapy and subsequent intracerebral hemorrhage" Neurobiology of Aging 28:202-212 (2007).
Buttini et al., "β-Amyloid Immunotherapy Prevents Synaptic Degeneration in a Mouse Model of Alzheimer's Disease," *The Journal of Neuroscience*, 25(40):9096-9101 (2005).
Chauhan et al. "Intracerebroventricular Passive Immunization With Anti-Aβ Antibody in Tg2576" J of Neuroscience 74:142-147 (2003).
Check, "Nerve Inflamtion Halts Trail for Alzheimer's Drugs," Nature, 415:462 (2002).
Choi et al., "A Generic Intron Increases Gene Expression in Transgenic Mice," Molecular and Cellular Biology, 11(6):3070-3074 (1991).
Constantino, Expert opinion Sep. 17, 2010.
Corcoran et al., "Overexpression of hAPPswe Impaires Rewarded Alternation and Contextual Fear Conditioning in a Transgenic Mouse Model of Alzheimer's Disease," Learn Mem. 9(5):243-252:2000.

(56) References Cited

OTHER PUBLICATIONS

Cribbs et al., "Adjuvant-dependant modulation of th1 and th2 responses to immunization with B-amyloid", International Immunology, 2003, vol. 15, No. 4, pp. 505-514.
Database Geneseq, "Nucleotide Sequence of a Variable Heavy Chain of IgG4," EBI Accession No. GSN:ADZ51216 (2005).
Do et al., "Reprogramming Somatic Gene Activity by Fusion With Pluripotent Cells" *Stem Cell Reviews.*, 2:257-264 (2006).
Donnelly, "New Developments in Adjuvants," *Mechanism of Ageing and Development*, 93:171-177 (1997).
Ecuadorian Search Report of Jul. 2, 2009 for Ecuador Patent Application No. SP 03-4685.
Elan Reports First Quarter 2006 Financial Results. Business Wire (May 4, 2006) XP002620724.
Elan Reports First Quarter 2006 Financial Results. Business Wire (May 4, 2006) XP002620725.
European Examination Report as part of Dec. 8, 2008 communication for European Application 04720353.4.
European Examination Report of Sep. 23, 2008 for European Application 04776252.1-2405.
European Examination Report of Nov. 20, 2008 for European Application 08011409.3.
European Search Report of Feb. 7, 2011 for European Application EP 08 74 6362.6.
Extended European Search Report of Dec. 18, 2008 for European Application 05812436.6-1212.
Family and legal status of EP0613007, Inpadoc Search (2009).
Gauthier et al., "Alzheimer's Disease: Current Knowledge, Management and Research," Can. Med. Assoc. J., 157:1047-1052 (Oct. 15, 1997).
Genbank Accession No. AAD00856.1, "Igm Heavy Chain Variable Region [*Homo Sapiens*]," Jul. 31, 2001.
Genbank Accession No. AAA69734, Schroeder et al., "Immunoglobulin heavy chain [*Homo sapiens*]", Anti-DNA immunoglobulin light chain IgG [*Mus musculus*], Jul. 11, 1995.
Genbank Accession No. AAB35009.1, Wang et al., "Antiidiotypic Ig 1F7 Light Chain Variable Region [Human, 1F7 Hybridoma Cells, Peptide Partial, 120aa]," Oct. 28, 1995.
Genbank Accession No. BAC01733, Akahori et al., "Immunoglobulin kappa light chain VLJ region [*Homo sapiens*]", Jul. 2, 2002.
Ghetie et al., "CD4 Peptide-Protein Conjugates, But Not Recombinant Human CD4, Bind to Recombinant gp120 From the Human Immunodeficiency Virus in the Presence of Serum From AIDS Patients.," Proc. Natl. Acad. Sci., 88:5690-5693 (1991).
Ghochikyan, "Rationale for Peptide and DNA Based Epitope Vaccine for Alzheimer's Disease Immunotherapy", CNS Neurol Disord Drug Targets, 2009: 8(2): 128 1-18.
Golding et al., "Vaccine Strategies: Targeting Helper T Cell Responses," *Annals New York Academy of Sciences*, 31:126-137 (1995).
Greenberg et al. "Amyloid Angiopathy-Related Vascular Congnitive Impairment" Stoke., 35:2616-2619 (2004).
Hamilton, "Molecular Engineering: Applications to the Clinical Laboratory," Clin. Chem. 39(9):1988-1997 (1993).
Harlow et al., eds., *Antibodies: A Laboratory Manual*, pp. 139-195 (1988).
Hartwig, "Immune ageing and Alzheimer's disease," *NeuroReport*, 6:1274-1276 (1995).
Hellman et al., "Allergy Vaccines—A Review of Developments," *Clin. Immunother.*, 6(2):.130-142 (Aug. 1996).
Hermanson et al., "Amino Acids as Spacers," *Immobilized Affinity Ligand Techniques*, section 3.1.1.5:150-152 (1992).
Hezareh et al., "Effector Function Activities of a Panel of Mutants of a Broadly Neutralizing Antibody against Human Immunodeficiency Virus Type 1," *Journal of Virology*, 24(75):12161-12168 (2001).
Hillen-Maske et al., "Konichalcit", *Rompp Chemie Lexilkon*, $9^{th}$ edition, p. 2322 (1990).
Hogarth, Fc Receptors Are Major Mediators of Antibody Based Inflammation in Autoimmunity, *Current Opinion in Immunology*, 14:798-802 (2002).
Holm et al., "Functional Mapping and Single Chain Construction of the Anti-Cytokeratin 8 Monoclonal Antibody TS1," *Mol. Immunol.*, 44(6):1075-1084 (Feb. 2007).
Huang et al., "Amyloid β-Peptide Possesses a Transforming Growth Factor-β-Activity," *The Journal of Biological Chemistry*, 273(42):27640-27644 (Oct. 16, 1998).
Hudson et al., "Antibody as a Probe," *Practical Immunology*, Chapter 2, pp. 34-85 (1989).
Janeway et al., *Immunobiology*, $3^{rd}$ edition, pp. 2:7, 2:9, 2:12, 8:16-8:17, 12:43 (1997).
Janeway et al., *Immunobiology*, $3^{rd}$ edition, pp. 8:18-8:19 (1997).
Jarrett et al., "The Carboxy Terminus of the β Amyloid Protein is Critical for the Seeding of Amyloid Formation: Implications for the Pathogenesis of Alzheimer's Disease," *Biochemistry*, 32:4693-4697 (Nov. 5, 1993).
Jennings, "Review of Selected Adjuvants Used in Antibody Production," *ILAR Journal*, 37(3) (1995).
Kallberg et al., "Prediction of Amyloid Fibril-Forming Proteins," *The Journal of Biological Chemistry*, 276(16):12945-12950 (Apr. 20, 2001).
Kardana et al., "Serum HCG β-Core Fragment is Masked by Associated Macromolecules," *Journal of Clinical Endocrinology and Metabolism*, 71(5):1393-1395, (1990).
Khan et al., "Immunopotentiation and Delivery Systems for Antigens for Single-Step Immunization: Recent Trends and Progress," *Pharmaceutical Research*, 11(1):2-11.
Kim et al., "In Vivo Engineering of a Cellular Immune Response by Coadministration of 1L-12 Expression Vector with a DNA Immunogen," *J. Immunol.*, 158:816-826 (1997).
Kinnecom et al., "Course of Cerebral Amyloid Angiopathy? Related Inflation," *Neurology*, 68(17):1411-1416 (2007).
Kofke et al., "Remifentanil-Induced Cerebral Blood Flow Effects in Normal Humans: Dose and ApoE genotype," *Neurosurg Anesthes Neurosci.*, 105(1):167-175 (2007).
Koller et al., "Active Immunization of Mice with a Aβ-Hsp70 Vaccine," *Neurodegenerative Disases*, 1:20-28 (2004).
Lemere, "Developing novel immunogens for a safe and effective Alzheimer's disease vaccine" Prog Brain Res. 2009; 175: 83 1-13.
Mann et al., "Atypical Amyloid (Abeta) Deposition in the cerebellum in Alzheimer's Disease: An Immunohistochemical Study Using End-Specific Abeta Monoclonal Antibodies," *ACTA Neuropathologica*, 91:647-653 (1996).
Mann et al., "Predominant deposition of myloid-beta 42(43) in plaques in cases of Alzheimer's disease and hereditary cerebral hemorrhage associated with mutatuibs in the myloid precursor protirn gene," *The American Journal of Pathology APR*, 4(148): 1257-1266 (1996).
Mavragani et al., "A Case of Reversible Posterior Leucoencephalopathy Syndrome After Rityximab Infusion," Rheumatology, 43(11) 1450-1451 (2006).
Misra et al., "Drug Delivery to the Central Nervous System: A review," *J. Pharm Pharm Sci.*, 6(2):252-273 (May 2003). Abstract.
Mitchell et al, "Prevention of Intracerebral Hemorrhage," *Current Drug Targets*, 8(7):832-838 (2007).
Mount et al. "Alzheimer disease: progress or profit?" Market Analysis Nature Medicine 12(7) 780-784 (Jul. 2006).
Movsesyan et al., "Reducing AD-Lide Pathology in 3xTg-AD Mouse Model by DNA epitope Vaccine—A Novel Immunotherapeutic Strategy", PloS ONE, 2008, vol. 3, issue 5, e2124 1-13.
Mutschler et al., "*Arzneimittel-Wirkungen, Lehrbuch der Pharmakologie und Taxiklogie*," Wissenschftliche Verlagsgesellschaft mbH Stuttgart, $6^{th}$ edition, pp. 651-656 (1991), (German Article).
Myers et. al., "Targeting Immune Effector Molecules to Human Tumor Cells Through Genetic Delivery of 5T4-Specific SCFV Fusion Protiens," Cancer Gene Therapy, 9(11):884-896 (2002).
Novartis, "Novartis MF59™—Adjuvanted Influenza Vaccine (Fluad®) Significantly Reduces Hospitalization in Elderly," Novartis Press Release, Oct. 19, 2007.

(56) References Cited

OTHER PUBLICATIONS

Padlan et al., Structure of an Antibody-Antigen Complex: Crystal Structure of the HyHEL-10 Fab-lysozyme Complex, Immunology, 86:5938-5942 (1989).
Pangalos et al., "Disease Modifiying Strategies for the Treatment of Alzheimer's Disease Targeted at Modulating Levels of β-amyloid Peptide," Biochemical Socity Transactions, 33(4):553-558 (2005).
PCT International Preliminary Report on Patentability (Chapter I) of Oct. 20, 2009 with Written Opinion of Oct. 3, 2008 for application PCT/US2008/060926.
PCT International Preliminary Report on Patentability (Chapter I) of Feb. 2, 2010 for application PCT/US07/09499.
PCT Search Report of Jan. 22, 2009 for application PCT/US2008/80370.
PCT Search Report of Mar. 25, 2009 for application PCT/US2008/80382.
PCT Search Report of Oct. 9, 2008 for application PCT/US2008/060926.
PCT Written Opinion of Mar. 8, 2009 for application PCT/US2008/80382.
PCT Written Opinion of Dec. 22, 2008 for application PCT/US2008/80370.
Prada et al., "Antibody-Mediated Clearance of Amyloid-β Peptide From Cerebral Amyloid Angiopathy Revealed by quantitative in Vivo Imaging," Journal of Neuroscience, 27(8):1973-1980 (2007).
Qu et al., "$Aβ_{42}$ gene Vaccine Prevents $Aβ_{42}$ deposition in brain of Double Trangenic Mice," *J. Neurological Sciences*, 260:204-213 (2007).
Ramshaw et al., "DNA vaccines for the treatment of autoimmune disease," *Immunology and Cell Biology*, 75:409-413 (1997).
Riechmann et al., "Reshaping Human Antibodies for Therapy," Nature, 332:323-327 (1988).
Robbins et al., "The Intronic Region of an Incompletely Spliced gp100 Gene Transcript Encodes an Epitope Recognized by Melanoma-Reactive Tumor-Infiltrarting Lymphocytes," Journal of Immunology, 159(1):303-308 (1997).
Saido et al., "Amino-and-Carboxyl-Terminal Heterogeneity of β-Amyloid Peptides Deposited in Human Brain," Neuroscience Letters, 215:173-176 (Aug. 8, 1996).
Saido et al., "Autolytic Transition of μ-Calpain Upon Activation as Resolved by Antibodies Distinguishing Between the Pre- and Post-Autolysis Forms," J. Biochem., 111:81-86 (1992).
Schmidt et al., "Monoclonal Antibodies to a 100-kd protein reveal abundant A beta-negative plaques throughout gray matter of Alzheimer's disease brains," *The American Journal of Pathology*, 1(151):69-80 (1997).
Schroeder et al., "Preferential Utilization of Conserved Immunoglobulin Heavy Chain Variable Gene Segments During Human Fetal Life," *Immunology*, 87:6146-6150 (1990).
Seabrook et al., "Species-specific Immune response to Immunization with Human Versus rodent Abeta Peptide," Neuobiology of Aging, 25(9) 1141-1151 (2004).
Sheehan et al., "The Utilization of Individual $V_{H\ Exons\ in\ the\ Primary\ Repertoire\ of\ Adult\ BALB/c\ Mice}^{1}$," The Journal of Immunology, 151(10):5364-5375 (Nov. 15, 1993).
Shepherd et al., "The design of the humanized antibody," Monocolonal Antibodies: A Pratical Approcach 58-66 (2000).
Sood et al., "Synthetic Peptides: A Modern Approach to Vaccination," *Indian Journal of Experimental Biology*, 34:849-861 (1998).
*Stedman's Medical Dictionary*, 27$^{th}$ Edition, "Vaccine," p. 1922, lines 1-3 (2000).
Studnicka et al., "Human-engineered monocilnal antibodies retain full specific binding activity by preserving non-CDR complementary-modullating resudes," Protien Eng., 7(6):805-814 (1994), Abstract only.
Tahtinen et al., "Minimal Size of HIV-1 NEF Antigenic Epitopes Reconzied by Human Sera," Int. Conf. AIDS Jun. 16-21, 1991, Published Jun. 1991, abstract No. W.A. 1334.

Tam, "Synthetic peptide vaccine design: synthesis and properties of a high-density multiple antigenic peptide system", Proc. Natl. Acad. Sci., 1988, vol. 85, pp. 5409-5413.
Tamaokaet al., "Antibodies to myloid beta protein (A beta) crossreact with glyceraldehyde-3-phosphate dehyrogenase (GAPDH)," *Neurobiology of Aging*, 3(17):405-414 (1996).
Trang et al., "Pharmacokinetics of a Mouse/Human Chimeric Monoclonal Antibody (C-17-1A) in Metastatic Adencarcinoma Patients," Pharmacutical Research 7(6):587-592 (1990).
Vastag, "Monoclonals expand into neural disorders" Nature 24:6 p. 595-596 (Jun. 2006).
Viswanathan et al., "Cerebral Microhemorrhage", *Stroke.*, 37:550-555 (2006).
Wang et al, "Site-specific UBITh amyloid-β vaccine for immunotherapy of Alzheimer's disease" *Vaccine* 25 (2007) 3041-3052.
Ward et al., "Spontaneous Deletions in IG Heavy Chain Genes Flaking Seuences Influence Splice Site Selection Nucleic Acids Research," 19(23): 6475-6480 (1991).
Wehner, Declaration May 21, 2007.
Welling et al., "Choice of Peptide and Peptide Length for the Generation of Antibodies Reactive With the Intact Protein," *FEBS Letters*, 182(1):81-84 (Mar. 1985).
Wikipedia entry for Antibody, retrieved Apr. 27, 2009 from en.wikipedia.org/wiki/Antibody.
Wilcock, et al. "Deglycosylated anti-Amyloid-β Antibodies Eliminate Cognitive Deficits and Reduce Parenchymal Amyloid with Minimal Vascular Consequences in Aged Amyloid Precursor Protein Transgenic Mice" Neurobiology of Disease 26(20:5340-5346 (May 17, 2006).
Yanagisawa K et al., "Amyloid BETA-protein (Alpha-Beta) associated with lipid molecules: immunoreactivity distinct from that of soluble Alpha-Beta," FEBS Letters, 1(420): 43-46 (1997).
Yang et al., "Monoclonal Antibody to the C-terminus of Beta-Amyloid," Neuroreport, 16(5):2117-2120 (1994).
"AAB-001 in Patients with Mild to Moderate Alzheimer's Disease" ClinicalTrials.gov last updated Sep. 22, 2009 3 pages.
Abcam, "Anti-beta Amyloid antibody 6F/3D", *Nucleic Acids Res.* 38:D142-D148 (2010).
Aihara, et al., "Immunocytochemical Localization of Immunoglobulins in the Rat Brain: Relationship to the Blood-Brain Barrier", *J of Comparative Neurology* 342:481-496 (1994).
Alzheimer Research Forum, "Drugs in Clinical Trials" Oct. 18, 2010.
Applicants' submission in EP 07012421.9 dated Jun. 16, 2009.
Assignment executed Dec. 8, 2000 in respect of U.S. Appl. No. 60/067,740.
Assignment executed Dec. 8, 2000 in respect of U.S. Appl. No. 60/080,970.
Birmingham et al., "Set back to Alzheimer vaccine studies" Nature Medicine 8(3):199-200 (2002).
Bruggermann, et al. "The Immunogenicity of Chimeric Antibodies" *J. Exp Med.*, 170(2):153-2157 (1989).
Chalmers et al., "APOE epsilon 4 influences the pathological phenotype of Alzhemier's disease by favouring cerebrovascular over parechyma accumulation of A beta protein", Neuropathology and Applied Neurobiology, vol. 29, No. 3 pp. 231-238 (2003).
Claudio, "Ultrastructural features of the blood-brain barrier in biopsy tissue for Alzheimer's disease patients." *Acta Neuropathol*. 91:6-14 (1996).
Communication in EP 07012421.9 pursuant to Art. 94(3) EPC dated Nov. 5, 2010.
Decision of Opposition Division in EP 1 160 256 dated Feb. 17, 2011.
Declaration by Dr. Dale Schenk dated Nov. 21, 2011.
Declaration of Dr. Mattias Staufenbiel Ph D. Jul. 15, 2011.
Declaration of Shyra J. Gardai dated Mar. 2, 2009.
Druckexemplar in EP 1 160 256 dated Jan. 25, 2010.
European Extended Search Report of Mar. 1, 2012 for European Application 08839961.
European Extended Search Report of Mar. 15, 2012 for European Application 09075267.6.
Extract from EPO patent register of EP 1 160 256 retrieved on Sep. 7, 2011.

(56) References Cited

OTHER PUBLICATIONS

Extract from EPO patent register of EP 1 842 859 retrieved on Sep. 7, 2011.
Gambetti, et al., "Human brain amyloidosis", *Nephrology Dialysis Transplantation*, 13(Suppl. 7):33-40, (1998).
GenBank, Accession No. AAA38630.1, "Immunoglobulin gamma-1 chain [*Mus musculus*]" May 5, 1994.
Ghersi-Egea et al., "Fate of Cerebrospinal Fluid-Borne Amyloid β-Peptide: Rapid Clearance into Blood and Appreciable Accunulation by Cerebral Arteries," *Journal of Neurochemistry*. vol. 67 No. 2:860-883 (1996).
Greisman et al., "A General Strategy for Selecting High-Affinity Zinc finger Proteins for Diverse DNA Target Sites" Science vol. 275:657-661 (1997).
Gustavsson et al., "Mechanisms of Transthyretin Amyloidogenesis Antigenic Mapping of Transthyretin Pruified from Plasma and Amyloid Fibrils and within in Situ Tissue Localizations" American Journal of Pathology 44(6):1301-1311 (1994).
Hampel et al., "Measurement of Phosphorylated Tau epitopes in the Differential Diagnosis of Alzheimer Disease", Arch Gen Psychiatry (2004) 61(1):95-102.
Hyman, et al. "Kunitz Protease Inhibitor-Containing Amyloid β Protein Precursor Immunoreactivity in Alzheimer's Disease", *J. of Neuropathology*, 51(1):76-83 (1992).
Invitrogen Data Sheet, "Mouse anti-β-Amyloid Peptide", Catalog No. 13-0100Z (Rev 10/08) DCC-08-1089.
Jagust et al., "Brain Imaging Evidence of preclinical Alzheimer's disease in normal aging" Ann Neurol, (2006) 59:67-681, abstract p. 676, table 1.
Janeway, et al., *Immunobiology: The Immune System In Health and Disease* 3rd Edition; cover pages and pp. 3.22-3.27 (1997).
Jefferis, "Antibody therapeutic: isotype and glycoform selection", *Expert Opin. Biol. Ther*; 7(9):1401-1413 (2007).
Klafki et al., "Therapeutic approaches to Alzheimer's disease" *Brain* 129:2840-2825 (2006).
Kuby, *Immunology*, 2nd Ed., Freeman pp. 126 and 168-171 (1994).
Marx et al., "Immune recognition of the Alzheimer amyloid β protein" Poster presentation; Autoreactive T. cells p. 5.18.03 Jun. 25, 1997.
Moretto, et al., "Conformation-sensitive Antibodies against Alzheimer Amyloid-β by Immunization with a Thioredoxin-constrained B-cell Epitope Peptide", *J of Biological Chemistry*, 282(14):11436-11445 (2007).
Patentee's Grounds of Appeal in EP Patent No. 1 033 996 dated Jul. 18, 2011.
PCT International Preliminary Report on Patentability (Chapter I) and Written Opinion Completed Dec. 22, 2008 for PCT/US2008/080370.
PCT/US2011/026365 International Preliminary Report on Patentability mailed Mar. 5, 2012.
PCT/US2011/026365 International Written Opinion and Search Report mailed Jul. 13, 2011.
PCT/US2011/033649 International Written Opinion and Search Report mailed Aug. 26, 2011.
Poduslo et al., "Macromolecular permeability across the blood-nerve and blood-brain barriers," *Proc. Natl. Acad. Sci USA*. vol. 91 pp. 5705-5709 (1994).
Ray. "Wyeth Study Finds Alzheimer's Drug Works in ApoE4 Non-Carriers". Poster 2008, [retrieved from the Internet Jun. 16, 2011: <URL: elan2006.blogspot.com/2008/07/elan-wyeth-studfindalzheimerdrug.html>].
Robert et al., Engineered antibody intervention strategies for Alzheimer's disease and related dementias by targeting amyloid and toxic oligomers:, Protein Eng Des Sel. (2009) 22:(2)199-208.
Stern, et al. "Monoclonal Antibodies to a Synthetic Peptide Homologous with the First 28 Amino Acids of Alzheimer's Disease β-Protein Recognize Amyloid and Diverse Glial and Neuronal Cell Types in the Central Nervous System" *Am J of Pathology*,134(5):973-978 (1989).
Takahashi, et al "Monoclonal antibody to β peptide, recognizing amyloid deposits, neuronal cells and lipofuscin pigments in systemic organs", *Acta Neuropathol*, 85:159-166 (1993).
Van Dam et al., "Symptomatic effect of donepezil, rivastigmine, galantamine and memantine on cognitive deficits in the APP23 model" *Psychopharmacology* 180:177-190 (2005).
Van Noort, Multiple sclerosis: an altered immune response or an altered stress response?, *J Mol Med* 74:285-296 (1996).
Vanengelen, et al "Immunoglobulin treatment in human and experimental epilepsy" *J of Neuro* (1994); 57 (supplement):72-75.
Wiessler, et al "The Second-Generation Active Aβ Immunotherapy CAD106 Reduces Amyloid Accumulation in APP Transgenic Mice While Minimizing Potential Side Effects", *J. Neurosci*. 31(25):9323-9331 (2011).
Wikipedia entry for "Monoclonal antibody therapy" accessed on Sep. 22, 2011.
Wu et al., "Saponin Adjuvant Enhancement of Antigen-Specific Immune Responses to an Experimental HIV-1 Vaccine" J of Immunology 149:1519-1525 (1992).
Zhao et al., "Macrophage-Mediated Degradation of β-Amyloid via an Apolipoprotein E Isoform-Dependent Mechanism", Neurobiology of disease (Mar. 18, 2009) 29(11):3603-3612.
Zlokovic et al., "Blood-Brain Barrier Transport of Circulating Alzheimer's Amyloid β." *Biochemical and Biophysical Research Communications*. vol. 197, No. 3, pp. 1034-1040 (1993).
Zotova et al., "Inflammation in Alzheimer's disease: relevance to pathogenesis and therapy" Alzheimer's Research & Therapy 2:1 p. 2-9 (2010).
U.S. Appl. No. 12/297,636, Office Action mailed Jul. 20, 2011.
U.S. Appl. No. 12/297,636, Office Action mailed Oct. 28, 2011.
U.S. Appl. No. 12/608,869, Office Action mailed Jul. 5, 2011.
U.S. Appl. No. 13/123,898, Office Action mailed Nov. 15, 2011.
U.S. Appl. No. 12/608,869, Office Action mailed Oct. 25, 2011.
U.S. Appl. No. 12/738,396, Office Action mailed Feb. 13, 2012.
U.S. Appl. No. 12/977,013, Office Action mailed Jan. 6, 2012.
U.S. Appl. No. 10/429,216, Office Action mailed May 24, 2011.
U.S. Appl. No. 11/809,552, Office Action mailed Feb. 17, 2011.
U.S. Appl. No. 11/841,919, Office Action mailed Mar. 28, 2011.
U.S. Appl. No. 11/893,123, Office Action mailed May 11, 2011.
U.S. Appl. No. 12/106,206, Office Action mailed Jul. 9, 2010.
U.S. Appl. No. 09/724,495, Advisory Action mailed May 16, 2006.
U.S. Appl. No. 10/777,792, Advisory Action mailed Mar. 6, 2009.
U.S. Appl. No. 11/664,865, Office Action mailed Feb. 11, 2011.
U.S. Appl. No. 12/037,045, Office Action mailed Nov. 4, 2011.
U.S. Appl. No. 10/923,469, Notice of Allowance mailed Jun. 1, 2011.
U.S. Appl. No. 11/893,123, Notice of Allowance mailed Nov. 2, 2011.
U.S. Appl. No. 12/181,238, Notice of Allowance mailed Mar. 11, 2011.
U.S. Appl. No. 12/106,206, filed Apr. 18, 2008, Schroeter.
U.S. Appl. No. 12/037,045, filed Feb. 25, 2008, Seubert.
U.S. Appl. No. 60/999,423, filed Oct. 17, 2007, Black.
U.S. Appl. No. 11/894,789, filed Aug. 20, 2007, Basi.
U.S. Appl. No. 11/894,754, filed Aug. 20, 2007.
U.S. Appl. No. 11/894,714, filed Aug. 20, 2007, Basi.
U.S. Appl. No. 11/894,665, filed Aug. 20, 2007, Schenk.
U.S. Appl. No. 11/893,123, filed Aug. 20, 2007.
U.S. Appl. No. 11/893,110, filed Aug. 20, 2007.
U.S. Appl. No. 11/893,103, filed Aug. 20, 2007.
U.S. Appl. No. 11/893,094, filed Aug. 20, 2007.
U.S. Appl. No. 11/842,120, filed Aug. 20, 2007, Schenk.
U.S. Appl. No. 11/842,116, filed Aug. 20, 2007, Schenk.
U.S. Appl. No. 11/842,113, filed Aug. 20, 2007, Schenk.
U.S. Appl. No. 11/842,101, filed Aug. 20, 2007, Schenk.
U.S. Appl. No. 11/842,056, filed Aug. 20, 2007, Basi.
U.S. Appl. No. 11/842,042, filed Aug. 20, 2007, Basi.
U.S. Appl. No. 11/842,023, filed Aug. 20, 2007, Basi.
U.S. Appl. No. 11/841,993, filed Aug. 20, 2007, Arumugham.
U.S. Appl. No. 11/841,950, filed Aug. 20, 2007, Arumugham.
U.S. Appl. No. 11/841,919, filed Aug. 20, 2007, Arumugham.
U.S. Appl. No. 11/841,897, filed Aug. 20, 2007, Arumugham.
U.S. Appl. No. 11/841,882, filed Aug. 20, 2007, Arumugham.
U.S. Appl. No. 11/841,857, filed Aug. 20, 2007, Warne et al.

(56) References Cited

OTHER PUBLICATIONS

U.S. Appl. No. 11/841,849, filed Aug. 20, 2007, Arumugham.
U.S. Appl. No. 11/841,794, filed Aug. 20, 2007, Warne et al.
U.S. Appl. No. 11/841,832, filed Aug. 20, 2007, Warne et al.
U.S. Appl. No. 60/793,014, filed Apr. 18, 2006.
U.S. Appl. No. 11/396,417, filed Mar. 30, 2006, Schenk.
U.S. Appl. No. 11/396,391, filed Mar. 30, 2006, Schenk.
U.S. Appl. No. 11/358,951, filed Feb. 22, 2006, Solomon et al.
U.S. Appl. No. 60/736,119, filed Nov. 10, 2005, Jacobson.
U.S. Appl. No. 60/736,045, filed Nov. 10, 2005, Johnson-Wood.
U.S. Appl. No. 60/735,687, filed Nov. 10, 2005, Jacobson.
U.S. Appl. No. 11/245,524, filed Oct. 7, 2005, Schenk.
U.S. Appl. No. 11/245,916, filed Oct. 7, 2005, Schenk.
U.S. Appl. No. 60/691,821, filed Jun. 17, 2005, Godavarti.
U.S. Appl. No. 09/980,568, filed Mar. 12, 2005, Hirtzer.
U.S. Appl. No. 60/648,639, filed Jan. 28, 2005, Luisi et al.
U.S. Appl. No. 60/648,631, filed Jan. 28, 2005, Luisi et al.
U.S. Appl. No. 60/637,253, filed Dec. 16, 2004, Jacobson.
U.S. Appl. No. 60/637,138, filed Dec. 16, 2004, Jacobson.
U.S. Appl. No. 60/636,842, filed Dec. 15, 2004, Jacobson.
U.S. Appl. No. 60/636,810, filed Dec. 15, 2004, Jacobson.
U.S. Appl. No. 60/636,776, filed Dec. 15, 2004, Basi.
U.S. Appl. No. 60/636,687, filed Dec. 15, 2004, Johnson-Wood.
U.S. Appl. No. 60/636,684, filed Dec. 15, 2004, Basi.
U.S. Appl. No. 60/622,525, filed Oct. 26, 2004, Pavliakova.
U.S. Appl. No. 60/616,474, filed Oct. 5, 2004, Sinacore.
U.S. Appl. No. 60/530,481, filed Dec. 17, 2003, Arumugham.
U.S. Appl. No. 60/474,654, field May 30, 2003, Basi.
U.S. Appl. No. 60/444,150, filed Feb. 1, 2003 Yednock.
U.S. Appl. No. 09/979,701, filed Mar. 13, 2002, Schenk.
U.S. Appl. No. 60/363,751, filed Mar. 12, 2002, Basi.
U.S. Appl. No. 60/254,465, filed Dec. 8, 2000, Holtzman et al.
U.S. Appl. No. 60/254,498, filed Dec. 8, 2000, Holtzman et al.
U.S. Appl. No. 60/251,892, filed Dec. 6, 2000, Basi et al.
U.S. Appl. No. 09/724,842, filed Nov. 28, 2000, Chalifour et al.
U.S. Appl. No. 09/724,929, filed Nov. 28, 2000, Weiner.
U.S. Appl. No. 09/724,921, filed Nov. 28, 2000, Weiner.
U.S. Appl. No. 09/724,575, filed Nov. 28, 2000, Schenk.
U.S. Appl. No. 09/724,291, filed Nov. 28, 2000, Schenk.
U.S. Appl. No. 09/724,288, filed Nov. 28, 2000, Schenk.
U.S. Appl. No. 09/724,273, filed Nov. 28, 2000, Schenk.
U.S. Appl. No. 09/723,765, filed Nov. 28, 2000, Schenk.
U.S. Appl. No. 09/723,544, filed Nov. 28, 2000, Schenk.
U.S. Appl. No. 09/724,495, filed Nov. 27, 2000, Schenk.
U.S. Appl. No. 09/724,319, filed Nov. 27, 2000, Schenk.
U.S. Appl. No. 09/723,766, filed Nov. 27, 2000, Hirtzer.
U.S. Appl. No. 09/723,760, filed Nov. 27, 2000, Schenk.
U.S. Appl. No. 09/723,725, filed Nov. 27, 2000, Hirtzer.
U.S. Appl. No. 09/723,713, filed Nov. 27, 2000, Schenk.
U.S. Appl. No. 09/585,656.
U.S. Appl. No. 09/580,019, filed May 26, 2000, Schenk.
U.S. Appl. No. 09/580,015, filed May 26, 2000, Schenk.
U.S. Appl. No. 09/579,690, filed May 26, 2000, Brayden.
U.S. Appl. No. 60/186,295, filed Mar. 1, 2000, Rasmussen et al.
U.S. Appl. No. 60/184,601, filed Feb. 24, 2000, Holtzman et al.
U.S. Appl. No. 09/497,553, filed Feb. 3, 2000, Schenk.
U.S. Appl. No. 60/169,687, filed Dec. 8, 1999, Chain.
U.S. Appl. No. 60/168,594, filed Nov. 29, 1999, Chalifour et al.
U.S. Appl. No. 09/441,140, filed Nov. 16, 1999, Solomon et al.
U.S. Appl. No. 60/139,408, filed Jun. 16, 1999, Raso.
U.S. Appl. No. 60/137,047, filed Jun. 1, 1999, Hirtzer.
U.S. Appl. No. 60/137,010, filed Jun. 1, 1999, Schenk.
U.S. Appl. No. 60/136,655, filed May 28, 1999, Brayden.
U.S. Appl. No. 09/322,289, filed May 28, 1999, Schenk.
U.S. Appl. No. 60/080,970, filed Jan. 11, 1999, Schenk.
U.S. Appl. No. 09/204,838, filed Dec. 3, 1998, Weiner.
U.S. Appl. No. 60/079,697, filed Mar. 27, 1998, Weiner et al.
U.S. Appl. No. 60/067,740, filed Dec. 2, 1997, Schenk.
U.S. Appl. No. 60/067,219, filed Dec. 3, 1997, Weiner et al.
U.S. Appl. No. 60/925,228.

Aguzzi et al., "Prion research: the next frontiers," *Nature* 389:795-798 (1997).
Aisen, P., "Inflammation and Alzheimer's Disease: Mechanisms and Therapeutic Strategies," *Gerontology*, 43:143-149 (1997).
Akiyama et al., "Occurrence of the Diffuse Amyloid β-Protein (Aβ) Deposits With Numerous Aβ-Containing Glial Cells in the Cerebral Cortex of Patients With Alzheimer's Disease," *Glia*, 25:324-331 (1999).
Akiyama et al., "Inflammation and Alzheimer's disease," *Neurobiology of Aging*, 21:383-421 (2000).
Akiyama et al., "The amino-terminally truncated forms of amyloid β-protein in brain macrophages in the ischemic lesions of Alzheimer's disease patients," *Neuroscience Letters*, 219:115-118 (1996).
Alberts et al., eds. *Molecular Biology of The Cell, Third Edition*, chapter 23, pp. 1208-1209 (1994).
Alberts et al., eds. *Molecular Biology of The Cell, Third Edition*, chapter 23, pp. 1216-1218 (1994).
Alberts et al., *Molecular Biology of the Cell, 2nd Edition*, pp. 266-267, Garland Publishing Inc., New York (1989).
American Type Culture Collection (ATCC) Search Results for "1KTR, 1ETZ, 1JRH", http://www.atcc.org/, pp. 1-3, Feb. 22, 2007.
Amit et al., "Three-Dimensional Structure of an Antigen-Antibody Complex at 2.8 Å Resolution," Science, 233:747-753 (1986).
Andersen et al., "Do nonsteroidal anti-inflammatory drugs decrease the risk for Alzheimer's disease?", *Neurology*, 45:1441-1445 (1995).
Anderson, J. P., "Exact cleavage site of Alzheimer amyloid precursor in neuronal PC-12 cells," *Neuroscience Letters*, 128(1):126-128 (1991).
Anderson, M. W., "Amending the amyloid hypothesis," *The Scientist*, 18(20):28-29 (2004).
Andrew et al., *Current Protocols in Immunology*, 2.7.1-2.9.8, John Wiley & Sons, Inc. (1997).
Ankarcrona et al., "Biomarkers for apoptosis in Alzheimer's disease " *Int. J. Geriatric Psychiatry*, 20:101-105 (2005).
Ard et al., "Scavenging of Alzheimer's Amyloid β-Protein by Microglia in Culture," *J. Neuroscience Research*, 43:190-202 (1996).
Arendiash et al., "Behavioral assessment of Alzheimer's transgenic mice following long-term Aβ vaccination: Task specificity and correlations between Aβ deposition and spatial memory," *DNA and Cell Biology*, 20(11):737-744 (2001).
Askelof et al., "Protective immunogenicity of two synthetic peptides selected from the amino acid sequence of *Bordetella pertussis* toxin subunit S1," *PNAS*, 87:1347-1351 (1990).
Associated Press, "Immune cells may promote Alzheimer's, a study finds " *The Boston Globe* (Apr. 13, 1995).
Auld et al., "Alzheimer's disease and the basal forebrain cholinergic system: relations to β-amyloid peptides, cognition, and treatment strategies," *Progress in Neurobiol.*, 68:209-245 (2002).
Avis, "Perenteral Preparations," *Remington's Pharmaceutical Sciences*, 17:1518-1519 (1985).
Bacskai et al., "Imaging of amyloid-β deposits in brains of living mice permits direct observation of clearance of plaques with immunotherapy," *Nature Medicine*, 7(3):369-372.
Bacskai et al., "Non-Fc-mediated mechanisms are involved in clearance of amyloid-β in vivo by immunotherapy," *J. Neurosci.*, 22(18):7873-7878 (2002).
Balbach et al., "Amyloid fibril formation by $A\beta_{16-22}$, a seven-residue fragment of the Alzheimer's β-amyloid peptide, and structural characterization by solid state NMR," *Biochemistry*, 39:13748-13759 (2000).
Bales et al., "Administration of an Anti-Aβ Fab Fragment to $APP^{V717F}$ Transgenic Mice Reduces Neuritic Plaque," Abstract P4-396, presented at Poster Session P4: Therapeutics and Therapeutic Strategies-Therapeutic Strategies, Amyloid-Based, *Neurogiology of Aging*, 25:S587 (2004).
Bales et al., "Cholinergic dysfunction in a mouse model of Alzheimer disease is reversed by an anti-Aβ antibody," *J. Clin. Invest.*, 116(3):825-832 (2006).
Bard et al., "Peripherally administered antibodies against amyloid β-peptide enter the central nervous system and reduce pathology in a mouse model of Alzheimer disease " *Nature Medicine*, 6(8):916-919 (2000).

(56) References Cited

OTHER PUBLICATIONS

Bard et al., "Epitope and isotype specificities of antibodies to β-amyloid peptide for protection against Alzheimer's disease-like neuropathology," *PNAS*, 100(4):2023-2028 (2003).
Barrow et al., "Solution Conformations and aggregational Properties of Synthetic Amyloid Beta-Peptides of Alzheimer's Disease. Analysis of Circular Dichroism Spectra," *J. Mol. Biol.*, 225(4):1075-1093 (1992).
Bauer et al., "Interleukin-6 and α-2-macroglobulin indicate an acute-phase state in Alzheimer's disease cortices," *FEBS Letters*, 285(1):111-114 (1991).
Beasley, "Alzheimer's traced to proteins caused by aging," Reuters, Apr. 20, 2001 7:56 PM ET.
Bellotti et al., "Application of Monoclonal Anti-idiotypes in the Study of AL Amyloidosi: Therapeutic Implications," *Renal Failure*, 15(3):365-371 (1993).
Bending, "Humanization of Rodent Monoclonal Antibodies by CDR Grafting," *A Companion to Methods in Enzymology*, 8:83-93 (1995).
Benjamini et al., from *Immunology A Short Course*, Second Edition, Chapter 4, Antibody Structure, pp. 49-65, 1991, published by Wiley-Liss, Inc., New York, New York.
Benjamini et al., from *Immunology A Short Course*, Second Edition, pp. 136-138, 143, 73-74, 372-373, and 400-401, 1991, published by Wiley-Liss, Inc., New York, New York.
Benkirane, et al, "Antigenicity and Immunogenicity of Modified Synthetic Peptides Containing D-Amino Acid Residues," *J. Biol. Chem,.* 268(23):26279-26285 (1993).
Ben-Yedidia et al., "Design of peptide and polypeptide vaccines " *Current Opinion in Biotechnology*, 8:442-448 (1997).
Bercovici et al., "Chronic Intravenous Injections of Antigen Induce and Maintain Tolerance in T Cell Receptor-Transgenic Mice," *Eur. J. Immunol.*, 29:345-354 (1999).
Bickel et al., "Site Protected, Cationized Monoclonal Antibody Against Beta Amyloid as a Potential Diagnostic Imaging Technique for Alzheimer's Diseases " *Soc. for Neuroscience Abstracts*, 18:764 (1992).
Bickel et al., "Development and in Vitro Characterization of a Cationized Monoclonal Antibody against βA4 Protein: A Potential Probe for Alzheimer's Disease," *Bioconjugate Chem.*, 5:119-125 (1994).
Blasberg et al., "Regional Localization of Glioma-assoicated Antigen Defined by Monoclonal Antibody 81C6 in Vivo: Kinetics and Implications for Diagnosis and Therapy," *Cancer Research*, 47:4432-4443 (1987).
Blass, "Immunologic Treatment of Alzheimer's Disease," *New England J. Medicine*, 341(22):1694 (1999).
Bodmer et al., "Transforming Growth Factor-Beta Bound to Soluble Derivatives of the Beta Amyloid Precursor Protein of Alzheimer's Disease," *Biochem. Biophys. Res. Comm.*, 171(2):890-897 (1990).
Borchelt et al., "Accelerated Amyloid Deposition in the Brains of Transgenic Mice Coexpressing Mutant Presenilin 1 and Amyloid Precursor Proteins," *Neuron* 19:939-945 (1997).
Borenstein, S., "New Alzheimer's vaccine to be tested on people soon, Early experiments on mice halted condition; considered safe for humans," *Free Press*, Jul. 23, 2001.
Boris-Lawrie et al., "Recent advances in retrovirus vector technology," *Cur. Opin. Genetic Develop.*, 3:102-109 (1993).
Bork et al., "Go hunting in sequence databases but watch out for the traps," *Trends in Genetics*, 12(10):425-427 (1996).
Bork, P., "Powers and Pitfalls in Sequence Analysis: The 70% Hurdle," *Genome Research*, 10:398-400 (2000).
Brazil et al., "Effects of Incorporation of Immunoglobulin G and Complement Component C1q on Uptake and Degradation of Alzheimer's Disease Amyloid Fibrils by Microglia " *J. Biol. Chem.*, 275(22):16941-16947 (2000).
Brenner, S. E., "Errors in genome annotation," *Trends in Genetics*, 15(4):132-133 (1999).
Brice et al., "Absence of the amyloid precursor protein gene mutation (APP717 : Val->Ile) in 85 cases of early onset Alzheimer's disease," *J. Neurology, Neurosurg. Psychiatry*, 56:112-115 (1993).

Britt et al., "Formulation of an immunogenic human cytomegalovirus vaccine: responses in mice," *J. Infect. Dis.*, 171:18-25 Abstract (1995).
Broadwell et al., "Serum proteins bypass the blood-brain fluid barriers for extracellular entry to the central nervous system," *Exp. Neurol.*, 120(2):245-263 (1993).
Brookmeyer et al., "Projections of Alzheimer's Disease in the United States and the Public Health Impact of Delaying Disease Onset," *Am. J. Public Health*, 88:1337-1342 (1998).
Burdick et al., "Assembly and aggregartion properties of synthetic Alzheimer's A4/β amyloid peptide antigens," *J. Biol. Chem.*, 267:546-555 (1992).
Bussiere et al., "Morphological Characterization of Thioflavin-S-Positive Amyloid Plaques in Transgenic Alzheimer Mice and Effect of Passive Aβ Immunotherapy on Their Clearance," *Am. J. Pathology*, 165(3):987-995 (2004).
Cameron, "Recent Advances in Transgenic Technology," *Molecular Biotechnology*, 7:253-265 (1997).
Caputo et al., "Therapeutic approaches targeted at the amyloid proteins in Alzheimer's disease," *Clin. Neuropharm.*, 15:414A-414B (1992).
Casadesus et al., "The Estrogen Myth: Potential Use of Gonadotropin-Releasing Hormone Agonists for the Treatment of Alzheimer's Disease," *Drugs R D*, 7(3):187-193 (2006).
Casey, S.O., "Posterior Reversible Encephalopathy Syndrome: Utility of Fluid-attenuated Inversion Recovery MR Imaging in the Detection of Cortical and Subcortical Lesions " *Amer J Neuroradiol*, 21:1199-1206 (2000).
Castillo et al., "Amylin / Islet Amyloid Polypeptide: Biochemistry, Physiology, Patho-Physiology," *Diabete & Metabolisme* (Paris), 21:3-25 (1995).
Cassell et al., "Demography and Epidemiology of Age-Associated Neuronal Impairment," chapter 4, pp. 31-50 from *Funcitional Neurobiology of Aging*, Hof et al., eds., Academic Press (2001).
Casset et al., "A Peptide Mimetic of an Anti-CD4 Monoclonal Antibody by Rational Design," *Biochemical and Biophysical Research Commiunications*, 307:198-205 (2003).
Center for Biologics Evaluation and Research, U.S. Food and Drug Administration, Thimerosal in Vaccines (Mercury in Plasma-Derived Products), web site contents found at : http://www.fda.gov/cber/vaccine/thimerosal.htm, last updated May 16, 2002.
Chakrabarti et al., "Vaccinia Virus Expression Vector: Coexpression of B-Galactosidas Provides Visual Screening of Recombinant Virus Plaques," *Molecular and Cellular Biology*, 5(12):3403-3409 (1985).
Chang et al., "Adjuvant activity of incomplete Freund's adjuvant," *Advanced Drug Delivery Reviews*, 32:173-186 (1998).
Chao et al., "Transforming Growth Factor-β Protects human Neurons Against β-Amyloid Induced Injury," *Soc. Neurosci. Abstracts*, 19:513-7 (1993).
Chapman, "Model behavior," *Nature*, 408:915-916 (2000).
Check, "Battle of the Mind," *Nature*, 422:370-372 (2003).
Chimicon International, "Mouse Anti-Amyloid Beta Protein Monoclonal Antibody," Catalog # MAB1561 (2003-2005).
Chen et al., "Neurodegenerative Alzheimer-like pathology in PDAPP 717V→F transgenic mice," *Progress in Brain Research*, 117:327-337 (1998).
Chen et al., "A learning deficit related to age and beta-amyloid plaques in a mouse model of Alzheimer's disease " *Nature*, 408(6815):975-979 (2000).
Chen et al., "An Antibody to β Amyloid Precursor Protein Inhibits Cell-substratum Adhesion in Many Mammalian Cell Types," *Neuroscience Letters*, 125:223-226 (1991).
Chen et al., "Selection and Analysis of an Optimized Anti-VEGF Antibody: Crystal Structure of an Affinity-matured Fab in Complex with Antigen," *J. Mol. Biol.*, 293:865-881 (1999).
Chishti et al., "Early-onset Amyloid Deposition and Cognitive Deficits in Transgenic Mice Expressing a Double Mutant Form of Amyloid Precursor Protein 695," *J. Biol.Chem.*, 276(24):21562-70 (2001).
Chothia et al., "Domain Association in Immunoglobulin Molecules," *J. Mol. Biol.*, 186:651-663 (1985).
Chromy et al., "Self-assembly of Aβ(1-42) into globular neurotoxins," *Biochemistry*, 42(44):12749-12760 (2003).

(56) References Cited

OTHER PUBLICATIONS

Chung et al., "Uptake, Degradation, and Release of Fibrillar and Soluble Forms of Alzheimer's Amyloid β-Peptide by Microglial Cells," *J. Biol. Chem.*, 274(45):32301-32308 (1999).
Cirrito et al., "Amyloid β and Alzheimer disease therapeutics: the devil may be in the details," *J. Clin. Invest.*, 112:321-323 (2000).
Citron et al., "Evidence that the 42- and 40-amino acid forms of amyloid-β protein are generated from the β-amyloid precursor protein by different protease activities," *PNAS*, 93(23):13170-13175 (1996).
Citron, M., "Alzheimer's disease: treatments in discovery and development," *Nat. Neurosci.*, 5:1055-1057 (2002).
Clark et al., *Chemical Immunology Antibody Engineering IgG Effector Mechanisms*, 65:88-110 (1997).
Clayton et al., "Synucleins in Synaptic Plasticity and Neurodegenerative Disorders," *J. Neurosci. Res.*, 58:120-129 (1999).
Co et al., "Chimeric and humanized antibodies with specificity for the CD33 antigen," *J. Immunol.*, 148:1149-1154 (1992).
Coico et al., *Immunology A Short Course*, Fifth Edition, pp. 18-24 (2003).
Colman, "Effects of Amino Acid Sequence Changes on Antibody-Antigen Interactions," *Research In Immunology*, 145:33-36 (1994).
Coloma et al., "Transport Across the Primate Blood-Brain Barrier of a Genetically Engineered Chimeric Monoclonal Antibody to the Human Insulin Receptor," *Pharm. Res.*, 17:266-274 (2000).
Colombian Patent Application No. 98071271, Technical Opinion of Jean Paul Vernot submitted on Jun. 22, 2005 as evidence with the brief amending the nullity action (with English translation) (drafted Nov. 2004).
Comery et al., "Passive Immunization Against β-Amyloid Leads to Acute Cognition Improvement," *Society for Neuroscience*, abstract, Washington DC, 11-/12-16/05.
Conway et al., "Acceleration of oligomerization, not fibrillization, is a shared property of both α-synuclein mutations linked to early-onset Parkinson's disease: Implications for pathogenesis and therapy," *PNAS*, 97(2):571-576 (2000).
Cordell, B., "β-Amyloid formation as a potential therapeutic target for Alzheimer's disease," *Ann. Rev. Pharmacol. Toxicol.*, 34:69-89 (1994).
Corey-Bloom et al., "Clinical features distinguishing large cohorts with possible AD, probable AD, and mixed dementia," *J. Am. Geriatr. Soc.*, 41(1):31-37 Abstract (1993).
Costa et al., "Immunoassay for transthyretin variants associated with amyloid neuropathy," *Scand. J. Immunol.*, 38:177-182 (1993).
Cox et al., "Adjuvants—a classification and review of their modes of action," *Vaccine*, 15(3):248-256 (1997).
Cribbs et al, "All-D-Erantiomers of Beta-Amyloid Exhibit Similar Biological Properties to All-L-Beta-Amyloids," *J. Biol. Chem.*, 272:7431-7436 (1997).
Daly, et al., "Detection of the membrane-retained carboxy-terminal tail containing polypeptides of the amyloid precursor protein in tissue from Alzheimer's Disease brain," *Life Sci.*, 63:2121-2131 (1998).
Das et al., "Amyloid-β Immunization Effectively Reduces Amyloid Deposition in FcRγ Knock-Out-Mice," *J. Neuroscience*, 23(24):8532-8538 (2003).
Das et al., "Reduced effectiveness of Aβ-42 immunization in APP transgenic mice with significant amyloid deposition," *Neurobiology of Aging*, 22:721-727 (2001).
Davis, S. S., "Nasal Vaccines," *Advanced Drug Delivery Reviews*, 51:21-42 (2001).
De Felice et al., "β-Amyloid production, aggregation, and clearance as targets for therapy in Alzheimer's disease," *Cell Mol. Neurobiol.*, 22(5/6):545-563 (2002).
De La Cruz et al, "Immumogenicity [sic] and Epitope Mapping of Foreign Sequences via Genetically Engineered Filamentous Phage," *J Biol Chem*, 263(9):4318-4322 (1988).
De Lustig et al., "Peripheral Markers and Diagnostic Criteria in Alzheimer's Disease: Critical Evaluations," *Rev. In Neurosciences*, 5:213-225 (1994).

DeMattos et al., "Peripheral anti-Aβ antibody alters CNS and plasma clearance and decreases Aβ burden in a mouse model of Alzheimer's disease," *PNAS*, 98(15):8850-8855 (2001).
DeMattos et al., "Peripheral Anti Aβ Antibody Alters CNS and Plasma Aβ Clearance and Decreases Brain Aβ Burden in a Mouse Model of Alzheimer's Disease," published online before print Jul. 3, 2001 at 10.1073/pnas.151261398; *PNAS*, 98(15):8850-8855 (2001).
DeMattos et al., "Plaque-associated disruption of CSF and plasma amyloid-β (Aβ) equilibrium in a mouse model of Alzheimer's disease," *J. Neurochem.*, 81:229-236 (2002).
DeMattos et al., "Brain to plasma amyloid-β efflux: a measure of brain amyoid burden in a mouse model of Alzheimer's disease," *Science*, 295(5563):2264-2267 (2002).
Dewitt et al., "Astrocytes regulate microglial phagocytosis of senile plaque cores of Alzheimer's disease," *Experimental Neurology*, 149:329-340 (1998).
Dialog/Derwent, Abstract of WPI Acc No. 1997-054436/199706: Stable vaccine compsns.—comprise a macrocyclic lactone, a milbemycin, an avermectin, an antigen, a dispersing agent, an adjuvant, a water sol. organic solvent and saline or water, Derwent File 351: Derwent WPI database (1997).
Dialog/Derwent, Abstract of WPI Acc No. 1995-261292/199534: Novel monoclonal antibody against human high-affinity IgE receptor—and DNA fragment encoding the MAb, for the specific identification of human Fc-epsilon RI, Derwent WPI database (1995).
Dickey et al., "Duration and specificity of humoral immune responses in mice vaccinated with the Alzheimer's disease-associated β-amyloid 1-42 peptide," *DNA and Cell Biology*, 20(11):723-729 (2001).
Dickson et al., "Neuroimmunology of Alzheimer's disease: a conference report," *Neurobiology of Aging*, 13(6):793-798 (1992), abstract only.
Dictionary.com definition of "prophylactic", pp. 1-3 downloaded from internet Oct. 12, 2005.
Di Martino et al., "Production and Characterization of Antibodies to Mouse Scrapie-Amyloid Protein Elicited by Non-carrier Linked Synthetic Peptide Immunogens," *J. Molecular Recognition*, 4(2-3):85-91 (1991).
Diomede et al., "Activation effects of a prion protein fragment [PrP-(106-126)] on human leucocytes," *Biochem. J.*, 320:563-570 (1996).
Disis et al., "Granulocyte-macrophage colony-stimulating factor: An effective adjuvant for protein and peptide-based vaccines," *Blood*, 88(1):202-210 (1996).
Dodart, "Immunotherapy for Alzheimer's disease: will vaccination work? " *Trends in Molecular Medicine*, 9(3):85-87 (2003).
Dodart et al., "Immunization reverses memory deficits without reducing brain Aβburden in Alzheimer's disease model," *Nat. Neurosci.*, 5(5):452-457 (2002).
Dodel et al., "Immunotherapy for Alzheimer's disease," *Lancet Neurol.*, 2(4):215-220 (2003).
Doerks et al., "Protein annotation: detective work for function prediction," *Trends in Genetics*, 14(6):248-250 (1998).
Dovey et al., "Functional gamma-secretase inhibitors reduce beta-amyloid peptide levels in brain," *J. Neurochem.*, 76(1):173-181 (2001).
Drew et al., "Vaccination by cholera toxin conjugated to a herpes simplex virus type 2 glycoprotein D peptide," *Journal of General Virology*, 73:2357-2366 (1992).
Du et al., "Reduced levels of amyloid beta-peptide antibody in Alzheimer disease," *Neurology*, 57(5):801-5 (2001).
Du et al., "α$_2$-Macroglobulin as a β-Amyloid Peptide-Binding Plasma Protein," *J. Neurochemistry*, 69(1):299-305 (1997).
Duff et al., "Mouse model made," *Nature*, 373:476-477 (1995).
Duff et al., "Increased amyloid-β42(43) in brains of mice expressing mutant presenilin 1," *Nature*,383(6602):710-713 (1996).
Dumery et al., "β-Amyloid protein aggregation: its implication in the physiopathology of Alzheimer's disease," *Pathol. Biol.*, 49:72-85 (2001).
Eck et al., *Goodman and Gilman's The pharmacological basis of therapeutics*, Chapter 5, pp. 77-101 (1996).
Ecuador Patent Application No. SP 98/2764, English translation of Expert Report submitted Apr. 19, 2007 in support of the Appeal filed on Jul. 29, 2005.

(56) References Cited

OTHER PUBLICATIONS

El-Agnaf et al., "The influence of the central region containing residues 19-25 on the aggregation properties and secondary structure of Alzheimer's beta-amyloid peptide " *Eur. J. Biochem.*, 256(3):560-569 (1998).
Elan, "Elan and AHP Provide an Update on the Phase 2A Clinical Trial of AN-1792," Press Release. (Jan. 18, 2002).
Elan, "Elan and Wyeth Provide Update on Status of Alzheimer's Collaboration," Press Release (Mar. 1, 2002).
Elizan et al., "Antineurofilament antibodies in a postencephalitic and idiopathic Parkinson's disease," *J. Neurol. Sciences*, 59:341-347 (1983).
Eriksen et al., "NSAIDs and enantiomers of flurbiprofen target γ-secretase and lower Aβ42 in vivo," *J. Clin. Invest.*, 112(3):440-449 (2003).
Esiri, "Is an effective immune intervention for Alzheimer's disease in prospect?" *Trends in Pharm, Sci.*, 22:2-3 (2001).
Esler et al., "Point substitution in the central hydrophobic cluster of a human β-amyloid congener disrupts peptide folding and abolishes plaque competence," *Biochemistry*, 35:13914-13921 (1996).
European Search Report of May 22, 2006 for European Application 06075704.4-2107.
European Search Report of May 22, 2006 for European Application 06075479.3-2107.
European Search Report of Jan. 16, 2007 for European Application 04776252.1-2405.
European Examination Report of Mar. 9, 2007 for European Application 01995364.5-1222.
European Examination Report of Sep. 26, 2007 for European Application 04720353.4-1222.
European Examination Report of Oct. 8, 2007 for European Application 01995364.5-1222.
Felsenstein et al., "Processing of the β-amyloid precursor protein carrying the familial, Dutch-type, and a novel recombinant C-terminal mutation," *Neuroscience Letters*, 152:185-189 (1993).
Felsenstein et al., "Transgenic Rat and In-Vitro Studies of B-Amyloid Precursor Protein Processing:" *Alzheimer's and Parkinson's Diseases*, Hanin et al. Ed., pp. 401-409, Plenum Press, New York, (1995).
Finch et al., "Evolutionary Perspectives on Amyloid and Inflammatory Features of Alzheimer Disease," *Neurobiology of Aging*, 17(5):809-815 (1996).
Findeis et al, "Modified peptide inhibitors of amyloid B-peptide polymerization," *Biochemistry*, 38:6791-6800 (1999).
Findeis, M. A., "Approaches to discovery and characterization of inhibitors of amyloid β-peptide polymerization," *Biochem. Biophys. Acta*, 1502(1):76-84 (2000).
Fisher et al., "Expression of the amyloid precursor protein gene in mouse oocytes and embryos," *PNAS*, 88:1779-1782 (1991).
Flanders et al., "Altered expression of transforming growth factor-β in Alzheimer's disease," *Neurology*, 45:1561-1569 (1995).
Flood et al., "An amyloid β-Protein fragment, A β [12-28J, equipotently impairs post-training memory processing when injected into different limbic system structures," *Brain Res*, 663(2):271-276 (1994).
Flood, et al, "Topography of a binding site for small amnestic peptides deduced from structure-activity studies: Relation to amnestic effect of amyloid B protein," *PNAS*, 91:380-384 (1994).
Fonseca et al., "The Presence of Isoaspartic Acid in β-Amyloid Plaques Indicates Plaque Age," *Experimental Neurology*, 157(2):277-288 (1999).
Foote et al., "Antibody Framework Residues Affecting the Conformation of the Hypervariable Loops," *J. Mol. Biol.*, 224:487-499 (1992).
Fox et al., "Presymptomatic cognitive deficits in individuals at risk of familial Alzheimer's disease," *Brain*, 121:1631-1639 (1998).
Fragione et al., Familial cerebral amyloid angiopathy related to stroke and dementia. *Amyloid*, 8(Suppl 1):36-42 (2001), abstract only.

Frautschy et al., "Effects of injected Alzheimer β-amyloid cores in rat brain," *PNAS*, 88:8362-8366 (1991).
Frazer et al., "Immunoglobulins: Structure and Function," chapter 3, pp. 37-74 from *Fundamental Immunology, fourth edition*, W.E. Paul, eds., Lippincott-Raven publishers, Philadelphia (1999).
Frenkel et al., "Generation of auto-antibodies towards Alzheimer's disease vaccination," *Vaccine*, 19:2615-2619 (2001).
Frenkel et al., "High affinity binding of monoclonal antibodies to the sequential epitope EFRH of β-amyloid peptide is essential for modulation of fibrillar aggregation," *J. of Neuroimmunology*, 95:136-142 (1999).
Frenkel et al., "Immunization against Alzheimer's β-amyloid plaques via EFRH phage administration," *PNAS*, 97:11455-11459 (2000).
Frenkel et al., "N-terminal EFRH sequence of Alzheimer's β-amyloid peptide represents the epitope of its anti-aggregating antibodies," *J. of Neuroimmunology*, 88:85-90 (1998).
Frenkel, et al., "Modulation of Alzheimer's β-amyloid neurotoxicity by site-directed single chain antibody," *J. of Neuroimmunology*, 106:23-31 (2000).
Frenkel et al., "Reduction of β-amyloid plaques in brain of transgenic mouse model of Alzheimer's disease by EFRH-phage immunization," *Vaccine*, 21(11-12):1060-1065 (2003).
Frenkel et al., "Towards Alzheimer's 6-amyloid vaccination," *Biologicals*, 29(3-4):243-247 (2001).
Friedland et al., "Development of an anti-Aβ monoclonal antibody for in vivo imaging of amyloid angiopathy in Alzheimer's disease," *Mol. Neurology*, 9:107-113 (1994).
Friedland, et al., "Neuroimaging of Vessel Amyloid in Alzheimer's Disease," in *Cerebrovascular Pathology in Alzheimer's Disease*, eds. de la Torre and Hachinski, New York Academy of Sciences, New York, New York (1997).
Fukutani et al., "Cerebeller pathology in sporadic and familial Alzheimer's disease including APP 717 (Val->Ile) mutation cases: A morphometric investigation," *J. Neurologic Sci.*, 149:177-184 (1997).
Furlan et al., "Vaccination with amyloid-β peptide induces autoimmune encephalomyelitis in C57/BL6 mice," *Brain*, 126:285-291 (2003).
Games et al., "Alzheimer-type neuropathology in transgenic mice overexpressing V717F β-amyloid precursor protein," *Nature*, 373(6514):523-527 (1995).
Games et al., "Prevention and Reduction of AD-type Pathology in PDAPP Mice Immunized with $A\beta_{1-42}$," *Annals of the New York Academy of Science*, 920:274-284 (2000).
Gandy et al., "Amyloidogenesis in Alzheimer's disease: some possible therapeutic opportunities," *TiPS*, 13:108-113 (1992).
Gardella et al., "Intact Alzheimer amyloid precursor protein (APP) is present in platelet membranes and is encoded by platelet mRNA," *Biochem. Biophys. Res. Comm.*, 173:1292-1298 (1990).
Gaskin et al., "Human antibodies reactive with beta-amyloid protein in Alzheimer's disease," *J. Exp. Med.*, 177:1181-1186 (1993).
Geddes, "N-terminus truncated β-amyloid peptides and C-terminus truncated secreted forms of amyloid precursor protein: distinct roles in the pathogenesis of Alzheimer's disease," *Neurobiology of Aging*, 20:75-79 (1999).
Gelinas et al., "Immunotherapy for Alzheimer's disease," *PNAS*, 101(suppl. 2):14657-14662 (2004).
Genbank Accession No. AAB48800, "Anti-DNA immunoglobulin light chain IgG [Mus musculus]," Sep. 14, 2001.
Genbank Accession No. CAA46659, "IgE antibody light chain(VJ)," Jun. 15, 1993.
Genbank Accession No. X65775.1, "*M.musculus* DNA for IgE antibody light chain (VJ)," Jun. 15, 1993.
Genbank Accession No. AAD26773, "Immunoglobulin heavy chain VH3609-JH3 region [*Mus musculus*]," Apr. 22, 1999.
Geylis et al., "Immunotherapy of Alzheimer's disease 9AD): From murine models to anti-amyloid beta 9Ab) human monoclonal antibodies," *Autoimmunity Rev.*, 5:33-39 (2000).
Ghiso et al., "Epitope map of two polyclonal antibodies that recognize amyloid lesions in patients with Alzheimer's disease," *Biochem. J.*, 282 (Pt 2):517-522 (1992).

(56) References Cited

OTHER PUBLICATIONS

Gibson et al., "Abnormalities in Alzheimer's Disease Fibroblasts Bearing the APP670/671 Mutation," *Neurobiology of Aging*, 18(6):573-580 (1997).
Gilman, S. et al., "Clinical Effects of Aβ Immunization (AN1792) in Patients with AD in an Interrupted Trial," *Neurology*, 64:1553-1562 (2005).
Giulian et al., "Specific domains of β-amyloid from Alzheimer plaque elicit neuron killing in human microglia," *J Neurosci.*, 16(19):6021-6037 (1996).
Giulian, et al., "The HHQK Domain of b-Amyloid Provides a Structural Basis for the Immunopathology of Alzheimer's Disease," *J. Biol. Chem.*, 273:29719-29726 (1998).
Glenn et al., "Skin immunization made possible by cholera toxin," *Nature*, 391:851 (1998).
Glenner et al., "Alzheimer's Disease and Downs Syndrome: Sharing of a Unique Cerebrovascular Amyloid Fibril Protein," *Biochem. Biophys. Res. Comm.*, 122(3): 1131-1135 (1984).
Glenner et al., "Alzheimer's Disease: Initial Report of the Purification and Characterization of a Novel Cerebrovascular Amyloid Protein," *Biochem. Biophys. Res. Comm.*, 120(3): 885-890 (1994).
Goate et al., "Segregation of a missense mutation in the amyloid precursor protein gene with familial Alzheimer's disease," *Nature*, 349:704-706 (1991).
Goldfarb et al., "The Transmissible Spongiform Encephalopathies," *Ann. Rev. Med.*, 46:57-65 (1995).
Goldsby et al., "Vaccines," Chapter 18 from *Immunology, 4th Edition*, W.H. Freeman and Company, New York, pp. 449-465 (2000).
Goldsteins et al., "Exposure of cryptic epitopes on transthyretin only in amypoid and in amyloidogenic mutants," *PNAS*, 96:3108-3113 (1999).
Gong et al., "Alzheimer's disease-affected brain: presence of oligomeric Aβ ligands (ADDLs) suggests a molecular basis for reversible memory loss," *PNAS*, 100(18):10417-10422 (2003).
Gonzales-Fernandez et al., "Low antigen dose favors selection of somatic mutants with hallmarks of antibody affinity maturation," *Immunology*, 93:149-153 (1998).
Gorevic et al., "Ten to fourteen residue peptides of Alzheimer's disease protein are sufficient for amyloid fibril formation and its characteristic X ray diffraction pattern" *Biochem. and Biophy. Res. Commun.*, 147(2):854-862 (1987).
Gortner, *Outlines of Biochemistry*, pp. 322-323, John Wiley & Sons, Inc., New York (1949).
Gozes et al., "Neuroprotective strategy for Alzheimer disease: Intranasal administration of a fatty neuropeptide," *PNAS*, 93:427-432 (1996).
Gravina et al., "Amyloid β Protein (Aβ) in Alzheimer's Disease," *J. Biol. Chem.*, 270(13):7013-7016 (1995).
Greenberg et al., "Alzheimer disease's double-edged vaccine," *Nat. Med.*, 9(4):389-390 (2003).
Gross et al., "Microvascular specializations promoting rapid interstitial solute dispersion in nucleus tractus solitarius," *Am J Physiol Regul Integr Comp Physiol*, 259:R1131-R1138 (1990).
Grubeck-Loebenstein, et al., "Immunization with β-amyloid: could T-cell activation have a harmful effect?", *TINS*, 23:114 (2000).
Gupta et al., "Adjuvants for human vaccines—current status, problems, and future prospects," *Vaccine*, 13(14):1263-1275 (1995).
Gupta et al., "Differences in the immunogenicity of native and formalized cross reacting material (CRM197) of diptheria toxin in mice and guinea pigs and their implications on the development and control of diphtheria vaccine based on CRMs," *Vaccine*, 15(12/13): 1341-1343 (1997).
Haass et al. "Amyloid beta-peptide is produced by cultured cells during normal metabolism," *Nature*, 359(6393):322-325 (1992).
Haass et al., "Protofibrils, the unifying toxic molecule of neurodegenerative disorders?," *Nature Neuroscience*, 4(9):859-860 (2001).
Haass, C., "New hope for Alzheimer disease vaccine," *Nat Med.*, 8(11):1195-1196 (2002).

Haga et al., "Synthetic Alzheimer amyloid β/A4 peptides enhance production of complement C3 component by cultured microglial cells," *Brain Research*, 601:88-94 (1993).
Hanan and Solomon, "Inhibitory effect of monoclonal antibodies on Alzheimer's β-amyloid peptide aggregation," *Int. J. Exp. Clin. Invest.*, 3:130-133 (1996).
Hanes et al., "New advances in microsphere-based single-dose vaccines," *Advanced Drug Delivery Reviews*, 28: 97-119 (1997).
Hara et al., "Development of a safe oral Aβ vaccine using recombinant adeno-associated virus vector for Alzheimer's disease," *J. Alzheimer's Disease*, 6:483-488 (2004).
Hardy, "Amyloid, the presenilins and Alzheimer's disease," *TINS*, 20(4): 154-159 (1997).
Hardy, John, "New Insights into the Genetics of Alzheimer's Disease," *Annals of Med.*, 28:255-258 (1996).
Harigaya, et al., "Modified amyloid β protein ending at 42 or 40 with different solubility accumulates in the brain of Alzheimer's disease," *Biochem. Biophys. Res. Comm.*, 211:1015-1022 (1995).
Harlow et al., eds., *Antibodies: A Laboratory Manual*, pp. 71-82 (1988).
Harlow et al., eds., *Antibodies: A Laboratory Manual*, p. 98 (1988).
Harrington et al., "Characterization of an epitope specific to the neuron-specific isoform of human enolase recognized by a monoclonal antibody raised against a synthetic peptide corresponding to the C-terminus of β/A4-protein," *Biochimica Biophysica Acta*, 1158:120-128 (1993).
Hazama, et al., "Intranasal Immunization Against Herpes Simplex Virus Infection by Using a Recombinant Glycoprotein D Fused With Immunomodulating Proteins, the B Subunit of *Escherichia coli* Heat-Labile Enterotoxin and Interleukin-2," *Immunology*, 78:643-649 (1993).
He et al., "Humanization and pharmacokinetics of a monoclonal antibody with specificity for both E- and P-selectin" *J. Immunol*, 160:1029-1035 (1998).
Helmuth, "Further Progress on a β-Amyloid Vaccine," *Science*, 289:375 (2000).
Herlyn et al., "Monoclonal antibodies in cell-mediated cytotoxicity against human melanoma and colorectal carcinoma*," *Eur. J. Immunol.*, 9:657-659 (1979).
Hilbich et al., "Aggregation and secondary structure of synthetic amylold βA4 peptides of Alzheimer's disease," *J. Mol. Biol.*, 218:149-163 (1991).
Hilbich et al., "Substitutions of hydrophobic amino acid reduce the amyloidogenicity of Alzheimer's disease βA4 peptides" *J. Mol. Biol.*, 228:460-473 (1992).
Hilbich et al., "Human and rodent sequence analogs of Alzheimer's amyloid βA4 share similar properties and can be solubilized in buffers of pH 7.4," *Eur. J. Biochem.*, 201:61-69 (1991).
Hirschfield et al., "Amylodiosis: new strategies for treatment," *Int. J. Biochem. & Cell Biol.*, 35:1608-1613 (2003).
Hock et al., "Antibodies against β-Amyloid Slow Cognitive Decline in Alzheimer's Disease," *Neuron*, 38:542-554 (2003).
Hock et al., "Generation of antibodies specific for β-amyloid by vaccination of patients with Alzheimer disease," *Nat. Med.*, 8(11):1270-1275 (2002).
Holmes et al., "Long-term Effects of $A\beta_{42}$ Immunisation in Alzheimer's Disease: Follow-up of a Randomised, Placebo-controlled Phase I Trial," *Lancet*, 372: 216-223 (2008).
Holtzman et al., "Aβ immunization and anti-Aβ antibodies: potential therapies for the prevention and treatment of Alzheimer's disease," *Advanced Drug Delivery Reviews*, 54:1603-1613 (2002).
Hopp et al., "Prediction of protein antigenic determiniants from amino acid sequences," *Proc. Natl. Acad. Sci. USA* 78:3824-3828 (1981).
Hsiao et al., "Correlative Memory Deficits, Aβ Elevation, and Amyloid Plaques in Transgenic Mice," *Science*, 274: 99-102 (1996).
Huberman et al., "Correlation of cytokine secretion by mononuclear cells of Alzheimer's patients and their disease stage," *J. Neuroimmunology*, 52:147-152 (1994).
Human Immunology & Cancer Program brochure, from The University of Tennessee Medical Center/ Graduate School of Medicine, Knoxville, Tennessee (publication date unknown).

(56) References Cited

OTHER PUBLICATIONS

Hussain et al., "Selective Increases in Antibody Isotopes and Immunoglobulin G Subclass Responses to Secreted Antigens in Tuberculosis Patients and Healthy Household Contacts of the Patients," *Clinical and Diagnostic Laboratory Immunology*, 2(6): 726-732 (1995).
Hyman et al., "Molecular Epidemiology of Alzheimer's Disease," *N. E. J. Medicine*, 333(19):1283-1284 (1995).
Hyslop et al., " Will Anti-amyloid Therapies Work for Alzheimer's Disease?," *Lancet*, 372:180-182 (2008).
Ida et al., "Analysis of Heterogeneous βA4 Peptides in Juman Cerebrospinal Fluid and Blood by a Newly Developed Sensitive Western Blot Assay," *J. Biol. Chem.*, 271(37):22908-22914 (1996).
Idusogie et al., "Mapping of the C1q Binding Site on Rituxan, a Chimeric Antibody with a Human IgG1 Fc," *J. Immunology*, 164:4178-4184 (2000).
Ikeda, et al., "Immunogold labeling of cerebrovascular and neuritic plaque amyloid fibrils in Alzheimer's disease with an anti-β protein monoclonal antibody," *Lab. Invest.*, 57:446-449 (1987).
Irizarry et al., "Aβ Deposition Is Associated with Neuropil Changes, but not with Overt Neuronal Loss in the Human Amyloid Precursor Protein V717F (PDAPP) Transgenic Mouse," *J. Neuroscience*, 17(18):7053-7059 (1997).
Irizarry et al., "Alzheimer disease therapeutics," *J. Neuropathol. Exp. Neurol.*, 60(10):923-928 (2001).
Itagaki et al., "Relationship of microglia and astrocytes to amyloid deposits of Alzheimer's disease," *J. Neuroimmunology*, 24:173-182 (1989).
Iwatsubo et al., "Visualization of Aβ42(43) and Aβ40 in Senile Plaques with End-Specific Aβ Monoclonals: Evidence That an Initially Deposited Species Is Aβ 42(43)," *Neuron*, 13:45-53 (1994).
Jahrling et al., "Opsonization of Alphaviruses in Hamsters," *J. Medical Virology*, 12:1-16 (1983).
Jakes et al., "Characterisation of an Antibody Relevant to the Neuropathology of Alzheimer Disease," *Alzheimer Disease and Associated Disorders*, 9(1):47-51 (1995).
Jansen et al., "Immunotoxins: Hybrid Molecules Combining High Specificity and Potent Cytotoxicity," *Immun. Rev.*, 62: 185-216 (1982).
Jansen et al., "Use of Highly Encapsulated *Streptococcus pneumoniae* Strains in a Flow-Cytometric Assay for Assessment of the Phagocytic Capacity of Serotype-Specifid Antibodies," *Clinical & Diagnostic Lab. Immunol.*, 5(5):703-710 (1998).
Janus et al., "A beta peptide immunization reduces behavioural impairment and plaques in a model of Alzheimer's disease," *Nature* 408(6815):979-982 (2000).
Janus et al., "Transgenic mouse models of Alzheimer's Disease," *Physiol. Behav.*, 73(5):873-886 (2001).
Jen, et al., "Preparation and purification of antisera against different regions or isoforms of b-amyloid precursor protein," *Brain Research Protocols*, 2:23-30 (1997).
Joachim et al., "Antibodies to Non-beta Regions of the Beta-amyloid Precursor Protein Detect a Subset of Senile Plaques," *Am. J. of Pathology*, 138:373-384 (1991).
Jobling et al., "Analysis of structure and function of the B subunit of cholera toxin by the use of site-directed mutagenesis," *Molecular Microbiology*, 5(7):1755-1767 (1991).
Johnson-Wood et al., "Amyloid precursor protein processing and $A\beta_{42}$ deposition in a transgenic mouse model of Alzheimer disease," *PNAS*, 94:1550-1555 (1997).
Johnstone et al., Nuclear and Cytoplasmic Localization of the β-Amyloid Peptide (1-43) in Transfected 293 Cells, *Biochem. Biophys. Res. Comm.*, 220:710-718 (1996).
Jorbeck et al., "Artificial *Salmonella* Vaccines: *Salmonella typhimurium* O-antigen-Specific Oligosaccharide-Protein Conjugates Elicit Opsonizing Antibodies that Enhance Phagocytosis," *Infection and Immunity*, 32(2):497-502 (1981).
Jung et al., "Alzheimer's Beta-amyloid Precursor Protein Is Expressed on the Surface of Immediately Ex Vivo Brain Cells: a Flow Cytometric Study," *J. Neurosci. Res.*, 46(3):336-348 (1996).

Kajkowski et al., "β-Amyloid Peptide-induced Apoptosis Regulated by a Novel Protein Containing a G Protein Activation Module," *J. Biol. Chem.*, 276(22):18748-18756 (2001).
Kalaria, R. N., "Serum amyloid P and related molecules associated with the acute-phase response in Alzheimer's disease," *Res. Immunology*, 143:637-641 (1992).
Kalback et al., "APP Transgenic Mice Tg2576 Accumulate Aβ Peptides That Are Distinct from the Chemically Modified and Insoluble Peptides Deposited in Alzheimer's Disease Senile Plaques," *Biochemistry*, 41:922-928 (2002).
Kascsak et al., "Mouse Polyclonal and Monoclonal Antibody to Scrapie-Associated Fibril Proteins," *J. Virology*, 61(12):3688-3693 (1987).
Katzav-Gozansky et al., "Effect of monoclonal antibodies in preventing carboxypeptidase A aggregation," *Biotechnol. Appl. Biochem.*, 23:227-230 (1996).
Kawabata et al., "Amyloid plaques, neurofibrillary tangles and neuronal loss in brains of transgenic mice overexpressing a C-terminal fragment of human amyloid precursor protein," *Nature*, 354:476-478 (1991).
Kayed et al., "Conformational Transitions of Islet Amyloid Polypeptide (IAPP) in Amyloid Formation In Vitro," *J. Mol. Biol.*, 287:781-796 (1999).
Kelly, J. W., "Alternative conformations of amyloidogenic proteins govern their behavior," *Current Opinion in Structural Biology*, 6:11-17 (1996).
Kettleborough et al., "Humanization of a mouse monoclonal antibody by CDR-grafting: the importance of framework residues on loop conformation," *Protein Engineering*, 4(7):773-783 (1991).
Khatoon et al., "Levels of normal and abnormally phosphorylated tau in different cellular and regional compartments of Alzheimer's disease and control brains," *FEBS Letters*, 351:80-84 (1994).
Kida, et al., "Early amyloid-β deposits show different immunoreactivity to the amino- and carboxy-terminal regions of b-peptide in Alzheimer's disease and Down's syndrome brain," *Neuroscience Letters*, 193:105-108 (1995).
Kimchi et al., "Analysis of cerebral amyloid angiopathy in a transgenic mouse model of Alzheimer disease using in vivo multiphoton microscopy," *J. Neuropath Exp. Neurol.*, 60(3):274-279 (2001).
Klein et al., "Targeting small Aβ oligomers: the solution to an Alzheimer's disease conundrum?," *Trends in Neurosciences*, 24(4):219-224 (2001).
Klyubin et al., "Anti-Aβ Antibodies Prevent Block of Long-Term Potentiation in the CA1 Area of Rat Hippocampus InVivo by naturally Produced Aβ Oligomers," *Neurobiology of Aging*, 25:S224-S225, abstract P2-004, pp. S224-S225 (2004).
Kofler et al., "Mechanism of Allergic Cross-Reactions—III. cDNA Cloning and Variable-Region Sequence Analysis of Two IgE Antibodies Specific for Trinitrophenyl," *Mol. Immunology*, 29(2):161-166 (1992).
Kofler et al., "Immunoglobulin $_k$ Light Chain Variable Region Gene Complex Organization and Immunoglobulin Genes Encoding Anti-DNA Autoantibodies in Lupus Mice," *J. Clin. Invest.*, 82:852-860 (1988).
Konig et al., "Development and Characterization of a Monoclonal Antibody 369.2B Specific for the Carboxyl-Terminus of the βA4 Peptide," *Annals of NY Acad. Sci.*, 777:344-355 (1996).
Kotilinek et al., "Reversible memory loss in a mouse transgenic model of Alzheimer's disease," *J. Neurosci.*, 22(15):6331-6335 (2002).
Koudinov et al., "The soluble form of Alzheimer's amyloid beta protein is complexed to high density lipoprotein 3 and very high density lipoprotein in normal human plasma," *Biochem. & Biophys. Res. Comm*, 205:1164-1171 (1994).
Kovács et al., "Mutations of the Prion Protein Gene Phenotypic Spectrum," *J. Neurol* 249:1567-1582 (2002).
Krishnan et al., "Correlation Between the Amino Acid Position of Arginine in VH-CDR3 and Specificity for Native DNA Among Autoimmune Antibodies[1,2]," *J. Immunol.*, 157(6):2430-2439 (1996).
Kuby, J., eds., p. 123 from *Immunology, Third Edition*, W.H. Freeman & co., (1997).

(56) References Cited

OTHER PUBLICATIONS

Kuby, J., eds., pp. 108-109, 131-132 from *Immunology, Third Edition*, W.H. Freeman & co., (1997).

Kuo et al., "High levels of circulating Abeta42 are sequestered by plasma proteins in Alzheimer's disease," *Biochem. Biophys. Res. Comm.*, 257(3):787-791 (1999).

Kuo et al., "Water-soluble Aβ (N-40, N-42) Oligomers in Normal and Alzheimer Disease Brains," *J. Biol. Chem.*, 271(8):4077-4081 (1996).

Kuo et al., "Comparative Analysis of Amyloid-β Chemical Structure and Amyloid Plaque Morphology of Transgenic Mouse and Alzheimer's Disease Brains," *J. Biol. Chem.*, 276(16):12991-12998 (2001).

Kurashima et al., "Production of Monoclonal Antibody against Amyloid Fibril Protein and Its Immunohistochemical Application," *Appl. Pathol.*, 3(1-2):39-54 (1985).

LaDu et al., "Isoform-specific Binding of Apolipoprotein E to β-Amyloid," *J. Biol. Chem.*, 269(38):23403-23406 (1994).

Lambert et al., "Diffusible, nonfibrillar ligands derived from Aβ1-42 are potent central nervous system neurotoxins," *PNAS*, 95:6448-6453 (1998).

Lambert et al., "Vaccination with soluble Aβ oligomers generates toxicity-neutralizing antibodies," *J. Neurochem.*, 79:595-605 (2001).

Lampert-Etchells et al., "Regional Localization of Cells Containing Complement C1q and C4 mRNAs in the Frontal Cortex During Alzheimer's Disease," *Neurodegeneration*, 2:111-121 (1993).

Landolfi et al., "The Integrity of the Ball-and Socket Joint Between V and C Domains Is Essential for Complete Activity of a Humanized Antibody," *J. Immunology*, 166(3):1748-1754 (2001).

Langer, "New Methods of Drug Delivery," *Science*, 249:1527-1532 (1990).

Lannfelt et al., "Alzheimer's disease: molecular genetics and transgenic animal models," *Behavioural Brain Res.*, 57:207-213 (1993).

Lansbury, Peter T., "Inhibition of amyloid formation: a strategy to delay the onset of Alzheimer's disease," *Curr. Ops. in Chemical Biology*, 1:260-267 (1997).

Lavie et al., "EFRH-Phage Immunization of Alzheimer's Disease Animal Model Improves Behavioral Performance in Morris Water Maze Trials," *J. Molecular Neuroscience*, 24:105-113 (2004).

Lee et al., "Aβ immunization: Moving Aβ peptide from brain to blood," *PNAS*, 98(16):8931-8932 (2001).

Lemere et al., "Mucosal Administration of Aβ Peptide Decreases Cerebral Amyloid Burden in Pd-App Transgenic Mice," *Society for Neuroscience Abstracts*, 25(part )I, Abstract 519.6, 29th Annual Meeting, (Oct. 23-28, 1999).

Lemere, et al., "Nasal Aβ treatment induces anti-Aβ antibody production and decreases cerebral amyloid burden in PD-APP mice," *Annals of the NY Acad. Sci.*, 920:328-331 (2000).

Lemere et al., "Intranasal immunotherapy for the treatment of Alzheimer's disease: *Escherichia coli* LT and LT(R192G) as mucosal adjuvants," *Neurobiology of Aging*, 23(6):991-1000 (2002).

Leverone et al., "Aβ1-15 is less immunogenic than Aβ1-40/42 for intranasal immunization of wild-type mice but may be effective for 'boosting'," *Vaccine*, 21:2197-2206 (2003).

Levitt, M., "Molecular dynamics of native protein," *J. Mol . Biol.*, 168:595-620 (1983).

Levey, A. I., "Immunization for Alzheimer's disease: A shot in the arm or a whiff?," *Ann. Neurology*, 48(4):553-555 (2000).

Li et al., "Thermal Stabilization of Carboxypeptidase A as a Function of PH and Ionic Milieu," *Biochem. Mol. Biol. Int.*, 43(3):601-611 (1997).

Licastro et al., "Is immunotherapy an effective treatment for Alzheimer's disease?," *Immunity & Aging*, 1:1-2 (2004).

Linke, "Monoclonal antibodies against amyloid fibril protein AA. Production, specificity, and use for immunohistochemical localization and classification of AA-type amyloidosis," *J. Histochemistry and Cytochemistry*, 32(3):322-328 (1982).

Liu et al., "Amyloid β peptide alters intracellular vesicle trafficking and cholesterol homeostasis," *Proc. Natl. Acad. Sci.*, 95:13266-13271 (1998).

Livingston et al., "The Hepatitis B Virus-Specific CTL Responses Induced in Humans by Lipopeptide Vaccination Are Comparable to Those Elicited by Acute Viral Infection," *J. Immunol.*, 159:1383-1392 (1997).

Lo et al., "High level expression and secretion of Fc-X fusion proteins in mammalian cells," *Protein Engineering*, 11(6):495-500 (1998).

Lopez et al., "Serum auto-antibodies in Alzheimer's disease," *Acta. Neurol. Scand.*, 84:441-444 (1991).

Lue et al., "Soluble β-amyloid Peptide Concentration as a Predictor of Synaptic Change in Alzheimer's Disease," *Am. J. Pathol.*, 155:853-562 (1999).

MacCallum et al., Antibody-antigen Interactions: *Contact Analysis and Binding Site Topography*, 262:732-745 (1996).

Maggio et al., "Brain Amyloid—A Physicochemical Perspective," *Brain Pathology*, 6:147-162 (1996).

Majocha et al., "Development of a Monoclonal Antibody Specific for β/A4 Amyloid in Alzheimer's Disease Brain for Application to in Vitro Imaging of Amyloid Angiopathy," *The J. of. Nuclear Med.*, 33:2184-2189 (1992).

Mak, et al., "Polyclonals to b-amyloid (1-42) identify most plaque and vascular deposits in Alzheimer cortex, but not striatum," *Brain Research*, 667:138-142 (1994).

Mamikonyan et al., "Anti-A$β_{1-11}$ Antibody Binds to Different β-Amyloid Species, Inhibits Fibril Formation, and Disaggregates Preformed Fibrils but Not the Most Toxic Oligomers" *Biol Chem*, 282(31) 22376-22386 (2007).

Mandel et al., "Clinical trials in neurological disorders using AAV vectors: promises and challenges," *Curr. Opin. Mol. Ther.* 6(5):482-490 (2004).

Mann, et al., "Amyloid β protein (Aβ) deposition in chromosome 14-linked Alzheimer's disease: Predominance of A$β_{42(43)}$," *Annals of Neurology*, 40:149-156 (1996).

Mann et al., "Predominant deposition of amyloid-beta 42(43) in plaques in cases of Alzheimer's disease and hereditary cerebral hemorrhage associated with mutatuibs in the amyloid precursor protirn gene," *The American Journal of Pathology APR*, 4(148): 1257-1266 (1996).

Mann, et al., "The extent of amyloid deposition in brain in patients with Down's syndrome does not depend upon the apolipoprotein E genotype," *Neuroscience Letters*, 196:105-108 (1995).

Manning et al., "Genetic Immunization with Adeno-Associated Virus Vectors Expressing Herpes Simplex Virus Type 2 Glycoproteins B and D," *Journal of Virology*, 71(10):7960-7962 (1997).

Manoj et al., "Approaches to Enhance the Efficacy of DNA Vaccines ," *Critical Rev. Clin. Lab. Sci.*, 41(1):1-39 (2004).

Marhaug et al., "Monoclonal hybridoma antibodies to human amyloid related protein SAA," *Clin. Exp. Immunol.*, 50(2):390-396 (1982).

Marotta et al., "Overexpression of amyloid precursor protein A4 (β-amyloid) immunoreactivity in genetically transformed cells: Implications for a cellular model of Alzheimer amyloidosis," *PNAS*, 86:337-341 (1989).

Marshall, E., "Gene Therapy's Growing Pains," *Science*, 269:1050-1055 (1995).

Masliah et al., "Amyloid Protien Precursor Stimulates Excitatory Amino Acid Transport " *The Journal of Biological Chemisrty*, 273(20):12548-12554 (1998).

Masliah et al., "β-Amyloid peptides enhance α-synuclein accumulation and neuronal deficits in a transgenic mouse model linking Alzheimer's disease and Parkinson's disease," *PNAS*, 98(21):12245-12250 (2001).

Masliah et al., "Comparison of Neurodegenerative Pathology in Transgenic Mice Overexpressing V717F β-Amyloid Precursor Protein and Alzheimer's Disease," *J. Neuroscience*, 16(18):5795-5811 (1996).

Masters et al., "Amyloid Plaque core protein in Alzheimer Disease and Down Syndrome," *PNAS*, 82:4245-4249 (1985).

Mattson, "Cellular actions of beta-amyloid precursor protein and its soluble and fibrillogenic derivatives," *Physiol Rev.*, 77(4):1081-132 (1997).

(56) References Cited

OTHER PUBLICATIONS

Mattson et al., "Good and bad amyloid antibodies," *Science*, 301(5641):1845-1849 (2003).
Maury et al., "Immunohistochemical Localization of Amyloid in Finnish Hereditary Amyloidosis with Antibodies to Gelsolin Peptides," *Laboratory Investigation*, 64(3):400-404 (1991).
McGee et al., "The encapsulation of a model protein in poly (D, L lactide-co-glycolide) microparticles of various sizes: an evaluation of process reproducibility," *J. Micro. Encap.*, 14(2):197-210 (1997).
McGeer, et al., "Immunohistochemical localization of beta-amyloid precursor protein sequences in Alzheimer and normal brain tissue by light and electron microscopy " *J. of Neuroscience Res.*, 31:428-442 (1992).
McLaurin et al., "Therapeutically effective antibodies against amyloid-β peptide target amyloid-β residues and 4-10 and inhibit cytotoxicity and fibrillogenesis," *Nat Med.*, 8(11):1263-1269 (2002).
McLean et al., "Soluble pool of Aβ amyloid as a determinant of severity of neurodegeneration in Alzheimer's disease," *Amer. Neurological Assoc*, 46:860-866 (1999).
McNeal et al., "Stimulation of local immunity and protection in mice by intramuscular immuniation with triple- or double-layered rotavirus particles and QS-21," *Virology*, 243:158-166 (1998).
Meda et al., "Activation of microglial cells by β-amyloid protein and interferon-γ," *Nature*, 374:647-650 (1995).
Mena, et al., "Monitoring pathological assembly of tau and β-amyloid proteins in Alzheimer's disease," *Acta Neuropathol.*, 89:50-56 (1995).
Merluzzi, et al., "Humanized antibodies as potential drugs for therapeutic use," *Adv Clin Path.*, 4(2):77-85 (2000).
Merriam-Webster online medical dictionary, entry for "cure", accessed Sep. 5, 2006.
Miller et al., "Antigen-driven Bystander Suppression after Oral Administration of Antigens," *J. Exp. Med.*, 174:791-798 (1991).
Monsonego et al., "Immune hyporesponsiveness to amyloid β-peptide in amyloid precursor protein transgenic mice: Implications for the pathogenesis and treatment of Alzheimer's disease," *PNAS*, 98(18):10273-10278 (2001).
Monsonego et al., "Increased T cell reactivity to amyloid β protein in older humans and patients with Alzheimer's disease," *J. Clin. Invest.*, 112(3):415-422 (2003).
Monsonego et al., "Immunotherapeutic approaches to Alzheimer's disease," *Science*, 302(5646):834-838 (2003).
Morgan, et al., "A beta peptide vaccination prevents memory loss in an animal model of Alzheimer's disease," *Nature*, 408(6815):982-985 (2000).
Morgan et al., "The N-terminal end of the $C_H2$ domain of chimeric human IgG1 anti-HLA-DR is necessary for C1q, FcγRII and FcγRII binding," *Immunology*, 86:319-324 (1995).
Mori et al., "Mass Spectrometry of Purified Amyloid β Protein in Alzheimer's Disease " *J. Biol. Chem.*, 267(24):17082-17088 (1992).
Morris, et al., "The Consortium to Establish a registry for Alzheimer's Disease (CERAD)," *Neurology*, 39:1159-1165 (1989).
Munch et al., "Potentional neurotoxic inflammatory response to Aβ vaccination in humans," *J. Neural Transm.*, 109:1081-1087 (2002).
Munson eds., *Principals of Pharmacology: Basic Concepts & Clinical Applications*, pp. 47-48, Chapman & Hall, New York, New York (1995).
Murphy et al., "Development of a Monoclonal Antibody Specific for the COOH-Terminal of β-Amyloid 1-42 and Its Immunohistochemical Reactivity in Alzheimer's Disease and Related Disorders," *Am. J. Pathology*, 144(5):1082-1088 (1994).
Mutschler et al., *Drug Actions: Basic Principles and Therapeutic Aspects* pp. 7, 11-12, Medpharm Scientific Publishers, Stuttgart, Germany (1995).
Nakamura et al., "Histopathological studies on senile plaques and cerebral amyloid angiopathy in aged cynomolgus monkeys," *Exp. Anim.*, 43:711-718 (1995).
Nakamura, et al., "Carboxyl end-specific monoclonal antibodies to amyloid β protein (Aβ) subtypes (Aβ40 and Aβ42(43) differentiate Ab in senile plaques and amyloid angiopathy in brains of aged cynomolgus monkeys," *Neuroscience Letters*, 201:151-154 (1995).
Nakayama et al., "Histopathological studies of senile plaques and cerebral amyloidosis in cynomolgus monkeys," *J. of Med. Primatology*, 27:244-252 (1998).
Nalbantoglu, J., "Beta-amyloid protein in Alzheimer's disease," *Can. J. Neurol. Sci.*, 18(3 suppl.):424-427 (1991), abstract only.
Nashar et al., "Current progress in the development of the B subunits of cholera toxin and *Escherichia coli* heat-labile enterotoxin as carries for the oral delivery of herterologous antigens and epitopes," *Vaccine*, 11(2):235-40 (1993), abstract only.
Naslund et al., "Correlation between elevated levels of amyloid β peptide in the brain and cognitive decline," *J. Am. Med. Assoc.*, 283:1571 (2000).
Nathanson et al., "Bovine Spongiform Encephalopathy (BSE): Causes and Consequences of a Common Source Epidemic," *Am. J. Epidemiol.*, 145(11):959-969 (1997).
New York Times National, "Anti-Inflammatory Drugs May Impede Alzheimer's," (Feb. 20, 1994).
Newcombe et al., "Solubility characteristics of isolated amyloid fibrils," *Biochim. Biophys. Acta*, 104:480-486 (1965).
Ngo et al., "Computational Complexity, Protein Structure Prediction, and the Levinthal Paradox," pp. 492-495 from Chapter 14 of *The Protein Folding Problem and Tertiary Structure Prediction*, Merz et al., eds., Birkhauser Boston (1994).
Nicoll et al., "Neuropathology of human Alzheimer's disease after immunization with amyloid-β peptide: a case report," *Nature Medicine*, 9(4):448-452 (2003).
Niemann, "Transgenic farm animals get off the ground:" *Transgenic Research*, 7:73-75 (1998).
Novotny et al., "Structural invariants of antigen binding: Comparison of immunoglobulin $V_L$-$V_H$ and $V_L$-$V_L$ domain dimmers," *PNAS*, 82:4592-4596 (1985).
Okie, S., "Promising Vaccine Targets Ravager of Minds," *Washington Post*, p. A01, May 8, 2001.
Okura et al., "Nonviral Aβ DNA vaccine therapy against Alzheimer's disease: Long-term effect and safety," *PNAS*, 103(25):9619-9624 (2006).
Orkin et al., *Report and Recommendations of the Panel to Assess the NIH Investment in Research on Gene Therapy*, Dec. 7, 1995.
Orlandi et al., "Cloning immunoglobulin variable domains for expression by the polymerase chain reaction," *PNAS*, 86:3833-3837 (1989).
Paganetti et al., "Amyloid precursor protein truncated at any of the γ-secretase sites is not cleaved to β-amyloid," *J. Neurosci. Res.*, 46(3):283-293 (1996).
Palha et al., "Antibody recognition of amyloidogenic transthyretin variants in serum of patients with familial amyloidiotic polyneuropathy, " *J. Mol. Med.*, 78:703-707 (2001).
Pallitto et al., "Recognition sequence design for peptidyl modulators of β-amyloid aggregation and toxicity," *Biochemistry*, 38(12):3570-3578 (1999).
Pan et al., "Antibodies to β-Amyloid Decrease the Blood-to-Brain Transfer of β-Amyloid Peptide," *Exp. Biol. Med.*, 227(8):609-615 (2002).
Panka et al., "Variable region framework differences result in decreased or increased affinity of variant anti-digoxin antibodies," *PNAS*, 85:3080-3084 (1998).
Pardridge et al., "Chimeric peptides as a vehicle for peptide pharmaceutical delivery through the blood-brain barrier," *Biochem. Biophys. Res. Comm.*, 146:307-313 (1987).
Pardridge et al., "The Blood-Brain Barrier: Bottleneck in Brain Drug Development" *J. Am. Soc. Exp. Neurotherapeutics*, 2:3-14 (2005).
Paresce et al., "Microglial cells influence aggregates of the Alzheimer's disease amyloid beta-protein via a scavenger receptor," *Neuron*, 17:553-565 (Sep. 1996).
Parnetti et al., "Cognitive Enhancement Therapy for Alzheimer's Disease, The Way Forward," *Drugs*, 53(5):752-768 (1997).
Pascalis et al., "Grafting of "Abbreviated" Complementarity-Determining Containing Specifictiy-Determining Residues Essential for Ligand Contact to Engineer a Less Immunogenic Humanized Monoclonal Antibody," *The Journanal Immunology*, 169:3076-3084 (2002).

(56) References Cited

OTHER PUBLICATIONS

Paul et al., "Transdermal immunization with large proteins by means of ultradeformable drug carriers," *Eur. J. Immunol.*, 25: 3521-3524 (1995).
Paul, W. E., eds., *Fundamental Immunology*, Third Edition, pp. 292-295, Raven Press, New York (1993).
PCT International Preliminary Examination Report of Feb. 9, 2004 for application PCT/US01/46587.
PCT Written Opinion of Dec. 14, 2004 for application PCT/US04/02856.
PCT International Preliminary Report on Patentability (Chapter I) of Sep. 16, 2005 with Written Opinion of May 9, 2005 for application PCT/US04/007503.
PCT International Preliminary Report on Patentability (Chapter II) of Dec. 21, 2006 for application PCT/US2006/002837.
PCT International Preliminary Report on Patentability (Chapter I) of Jul. 31, 2007 with Written Opinion for application PCT/US2006/004741.
PCT Written Opinion of Aug. 11, 2006 for application PCT/US2006/002837.
PCT Search Report of Aug. 11, 2006 for application PCT/US2006/002837.
PCT Search Report of Aug. 8, 2006 for appl;ication PCT/US2005/045515.
PCT International Preliminary Report on Patentability (Chapter II) of Apr. 27, 2006 for application PCT/US04/007503.
PCT Search Report of Apr. 6, 2006 and Written Opinion of Apr. 8, 2006 for application PCT/US04/44093.
PCT Search Report of Oct. 1, 2007 and Written Opinion of Oct. 1, 2007 for application PCT/US07/09499.
Peeters et al., "Comparison of four bifunctional reagents for coupling peptides to proteins and the effect of the three moieties on the immunogenicity of the conjugates," *J. Immunological Methods*, 120:133-143 (1989).
Perez et al., "The β-Amyloid Precursor Protein of Alzheimer's Disease Enhances Neuron Viability and Modulates Neuronal Polarity," *J. Neurosci.*, 17(24):9407-9414 (1997).
Persson et al., "IgG subclass-associated affinity differences of specific antibodies in humans," *J. Immunology*, 140(11):3875-3879 (1988), abstract only.
Perutz et al., "Amyloid fibers are water-filed nanotubes," *PNAS*, 99(8):5591-5595 (2002).
Peterson, et al., "Recombinant Antibodies: Alternative Strategies for Developing and Manipulating Murine-Derived Monoclonal Antibodies," *Laboratory Animal Science*, 46(1):8-14 (1996).
Pfeifer et al., "Cerebral hemorrhage after passive anti-Aβ immunotherapy," *Science*, 298(5597):1379 (2002).
Phelps et al., "Development and Characterization of Monoclonal Antibodies Specific for Amylin," *Hybridoma*, 15(5):379-386 (1996).
Philippe, et al. "Generation of a monoclonal antibody to the carboxy-terminal domain of tau by immunization with the amino-terminal domain of the amyloid precursor protein," *J. of Neuroscience Res.*, 46:709-719 (1996).
Piera et al., "Cytokines as adjuvants: effects on the immunogenicity of NeuAc alpha 2-GalNAc alpha-O-Ser/Thr (sialyl-Tn)," *Int. J. Cancer*, 55(1):148-152 (1993).
Pluckthun, A., "Mono- and Bivalent Antibody Fragments Produced in *Escherichia coli*: Engineering, Folding and Antigen Binding," *Immunological Reviews*, 130:151-188 (1992).
PNAS Information for Authors (revised Jan. 1997), Retrieved Apr. 21, 2008 from web.archive.org/web/19970610092808/www.pnas.org/ifore.shtml.
Poduslo et al., "Permeability of proteins at the blood-brain barrier in the normal adult mouse and double transgenic mouse model of Alzheimer's disease," *Neurobiol. Dis.*, 8(4):555-567 (2001).
Press Release, "Alzheimer's vaccine developer awarded Potamkin Prize," American Academy of Neurology, May 7, 2001.
Prieels et al., "Synergistic adjuvants for vaccines," *Chemical Abstracts*, 120(8):652, col. 1, abstract 86406t (1994).
Probert et al., "Spontaneous inflammatory demyelinating disease in transgenic mice showing central nervous system-specific expression of tunmor necrosis factor α," *PNAS*, 92:11294-11298 (1995).
Prusiner et al., "Ablation of the prion protein (PrP) gene in mice prevents scrapie and facilitates production of anti-PrP antibodies," *PNAS*, 90:10608-10612 (1993).
Putative CDR determination for SEQ Id Nos: 2 and 4 (pp. 1-2), Jun. 10, 2004.
Qu et al., "Aβ$_{42}$ gene vaccination reduces brain amyloid plaque burden in transgenic mice," *J. Neurological Sciences*, 244:151-158 (2006).
Queen et al., "A humanized antibody that binds to the interleukin 2 receptor," *PNAS*, 86:10029-10033 (1989).
Quon et al., "Formation of β-Amyloid protein deposits in brains of transgenic mice," *Nature*, 352:239-241 (1991).
Racke et al., "Exacerbation of Cerebral Amyloid Angiopathy-Asoiciated Microhemorrhage in Amyloid Precursor Protein Trasngenic Mice by Immunotherapy Is Dependent on Antibody Recognition of Deposited Forms of amyloid β," *J. Neurosci.*, 25(3):629-636 (2005).
Ragusi et al., "Redistribution of Imipramine from Regions of the Brain Under the Influence of Circulating Specific Antibodies," *J. Neurochem.*, 70(5):2099-2105 (1998).
Rammensee, H.G., "Chemistry of peptides associated with MHC class I and class II molecules," *Current Opinion in Immunology*, 7:85-96 (1995).
Raso, "Immunotherapy of Alzheimer's Disease," *Immunotherapy Weekly*, Abstract (Apr. 2, 1998).
Raso, V.A., Grant application # 1 R43 AGI 5746-01 (redacted version), "Immunotherapy of Alzheimer's Disease" (publication date unknown).
Research Corporation Technology News, "THP and SangStat Partner to Develop Humanized Polyclonal Antibody Drugs," Nov. 11, 2002.
"Researchers Develop Blood Test to Diagnose Alzheimer's-Type Changes in Mice," downloaded from www.businesswire.com on Dec. 15, 2004.
Rodriguez et al., "Enfermedad de Azlheimer. Situacion Actual y Estrategias Terapeuticas" (Alzheimer Disease: present situation and therapeutic strategies), *Rev Cubana Med* [online], 38(2):134-142 (1999).
Rogers et al., "Complement activation by β-amyloid in Alzheimer Disease," *PNAS*, 89:1-5 (1992).
Rolph et al., "Recombinant viruses as vaccines and immunological tools," *Immunity to Infection*, 9:517-521 (1997).
Roses, A.D., "Apoplipoprotein E alleles as risk factors in Alzheimer's disease " *Annu. Rev. Med.*, 47:387-400 (1996).
Rossor et al., "Alzheimer's Disease Families with Amyloid Precursor Protein Mutations," *Annals of New York Academy of Sciences*, 695:198-202 (1993).
Rudikoff et al., "Single amino acid substitution altering antigen-binding specificity," *PNAS*, 79:1979-1983 (1982).
Rudinger, "Characteristics of the Amino Acids as Components of a Peptide Hormone Sequence," in *Peptide Hormones*, J.A. Parson, ed. University Park Press, Baltimore, pp. 1-7 (1976).
Saido et al., "Spatial Resolution of Fodrin Proteolysis in Postischemic Brain," *J. Biol. Chem.*, 268(33):25239-25243 (1993).
Saido et al., "Spatial Resolution of the Primary β-Amyloidogenic Process Induced in Postischemic Hippocampus," *J. Biol. Chem.*, 269(21):15253-15257 (1994).
Saito et al., "Vector-mediated delivery of $^{125}$I-labeled β-amyloid peptide Aβ$^{1-40}$ through the blood-brain barrier and binding to Alzheimer disease amyloid of the Aβ$^{1-4}$ vector complex," *PNAS*, 92:10227-10231 (1995).
Saitoh, N. et al., "Immunological analysis of Alzheimer's disease using anti-β-protein monoclonal antibodies," *Sapporo Med. J.*, 60:309-320 (1991).
Saldanha et al., "A single backmutation in the human kIV framework of a previously unsuccessfully humanized antibody restores the binding activity and increases the secretion in cos cells," *Molecular Immunology*, 36:709-719 (1999).
Sasaki et al., "Human choroid plexus is an uniquely involved area of the brain in amyloidosis: a histochemical, immunohistochemical and ultrastructural study," *Brain Res.*, 755:193-201 (1997).

(56) References Cited

OTHER PUBLICATIONS

Schenk et al., "Immunization with amyloid-β attenuates Alzheimer-disease-like pathology in the Pdapp mouse," *Nature*, 400:173-177 (1999).
Schenk et al., "Therapeutic Approaches Related to Amyloid-β Peptide and Alzheimer's Disease," *J. Med. Chem.*, 38(21):4141-4154 (1995).
Schenk et al., "β-peptide immunization," *Arch. Neurol.*, 57:934-936 (2000).
Schenk et al., "Immunotherapy with beta-amyloid for Alzheimer's disease: a new frontier," *DNA Cell Biol.*, 20(11):679-81 (2001).
Schenk, D., "Amyloid-β immunotherapy for Alzheimer's disease: the end of the beginning," *Nature Reviews*, 3:824-828 (2002).
Schenk et al., "Current progress in beta-amyloid immunotherapy," *Curr. Opin. Immunology*, 16(5):599-606 (2004).
Schmid, R. E., "Study suggest Alzheimer vaccine fix," from www.msnbc.com/news, pp. 1-5 (2002).
Schmitt et al., "Interactions of the alzheimer β amyloid fragment$_{(25-35)}$ with peripheral blood dendritic cells," *Mechanisms of Ageing and Development*, 94:223-232 (1997).
Schwarzman et al., "Transthyretin sequesters amyloid β protein and prevents amyloid formation," *PNAS* 91:8368-8372 (1994).
Seidl et al., "Predominant $V_H$ genes expressed in innate antibodies are associated with distinctive antigen-binding sites," *PNAS* 96:2262-2267 (1999).
Sela et al, "Different roles of D-amino acids in immune phenomena," *FASEB J*, 11(6):449-456 (1999).
Selkoe, "Alzheimer's Disease: A Central Role for Amyloid," *J. Neuropathol. Exp. Neurol.*, 53(5): 438-447 (1994).
Selkoe, "Physiological production of the β-amyloid protein and the mechanism of Alzheimer's disease," *Trends in Neurosciences*, 16(10): 403-409 (1993).
Selkoe, "The cell biology of beta-amyloid precursor protein and presenilin in Alzheimer's disease " *Trends Cell Biol.*, 8(11):447-53 (1998).
Selkoe, D.J., "Imaging Alzheimer's Amyloid," *Nat. Biotech.*, 18:823-824 (2000).
Selkoe, Dennis J., "Alzheimer's Disease: Genotypes, Phenotype, and Treatments," *Science*, 275:630-631 (1997).
Selkoe, Dennis J., "Amyloid Protein and Alzheimer's Disease . . . ," *Scientific American*, pp. 68-78 (1991).
Selkoe, Dennis J., "In the Beginning . . . ," *Nature*, 354:432-433 (1991).
Selkoe, Dennis J., "The Molecular pathology of Alzheimer's Disease," *Neuron*, 6:487-498 (1991).
Selkoe, D. J., "Alzheimer's disease is a synaptic failure," *Science*, 298(5594):789-791 (2002).
Sergeant et al., "Truncated beta-amyloid peptide species in pre-clinical Alzheimer's disease as new targets for the vaccination approach," *J. Neurochem.*, 85(6):1581-1591 (2003).
Seubert et al., "Isolation and quantification of soluble Alzheimer's β-peptide from biological fluids," *Nature*, 359: 325-327 (1992).
Seubert et al., "Antibody Capture of Soluble Aβ does not Reduce Cortical Aβ Amyloidosis in the PDAPP Mouse," *Neurodegenerative Diseases*, 5:65-71 (2008).
Shinkai et al., "Amyloid β-Proteins 1-40 and 1-42(43) in the Soluble Fraction of Extra- and Intracranial Blood Vessels," *Ann. Neurol.*, 38:421-428 (1995).
Shiosaka, S., "Attempts to make models for Alzheimer's disease," *Neuroscience Res.*, 13:237-255 (1992).
Sidhu, "Page display in pharmaceutical biotechnology," *Current Opinoin in Biotechnology*, 11:610-616 (2000).
Sigmund, "Viewpoint: Are Studies in Genetically Altered Mice Out of Control," *Arterioscler Thromb Vasc Biol.*, 20:1425-1429 (2000).
Signet Laboratories, Inc., Product data sheet for mouse monoclonal clone 6E10, revised Jul. 13, 2005.
Sigurdsson et al., "A safer vaccine for Alzheimer's disease?," *Neurobiology of Aging*, 23:1001-1008 (2002).
Sigurdsson et al., "Anti-prion antibodies for prophylaxis following prion exposure in mice," *Neurosciences Letters*, 336:185-187 (2003).

Sigurdsson et al., "Immunization Delays the Onset of Prion Disease in Mice," *American Journal of Pathology*, 161:13-17 (2002).
Sigurdsson, et al., "In vivo reversal of amyloid-beta lesions in rat brain," *J Neuropathol Exp Neurol.*, 59(1):11-17 (2000).
Sigurdsson et al., "Immunization with a Nontoxic/Nonfibrillar Amyloid-β Homologous Peptide Reduces Alzheimer's Disease-Associated Pathology in Trasngenic Mice," *Am. J. Pathology*, 159(2):439-447 (2001).
Simmons, L., "Secondary structure of amyloid β peptide correlates with neurotoxic activity in vitro," *Molecular Pharmacology*, 45:373-379 (1994).
Singh, K. S., "Neuroautoimmunity: Pathogenic Implications for Alzheimer's Disease," *Gerontology*, 43:79-94 (1997).
Singh, V. K., "Studies of neuroimmune markers in Alzheimer's disease," *Mol. Neurobiology*, (1994), abstract only.
Sinha, et al., "Recent advances in the understanding of the processing of APP to beta amyloid peptide " *Ann N Y Acad Sci.*, 920:206-8 (2000).
SPIE, "Amyloidosis," *Annu. Rev. Biochem.*, 61:947-975 (1992).
Skolnick and Fetrow, "From genes to protein structure and function: novel applications of computational approaches in the genomic era," *Trends in Biotech*, 18(1):34-39 (2000).
Small et al., "Alzheimer's disease and Abeta toxicity: from top to bottom," *Nat Rev Neurosci.*, 2(8):595-598 (2001).
Small et al., "Cerebral metabolic and cognitive decline in persons at genetic risk for Alzheimer's disease," *PNAS*, 97(11):6037-6042 (2000).
Small, "The Role of the Amyloid Protien Precursors (APP) in Alzheimer's Disease: Does the Normal Function of APP Explain the Topography of Neurodegeneration?," *Neurochemical Research*, 23(5):795-806 (1997).
Smith et al., "Phage Display," *Chemical Reviews, American Chemical Society*, 97(2):391-410 (1997).
Smith et al., "The challenges of genome sequence annotation or 'The devil is in the details,'" *Nature Biotechnology*, 15:1222-1223 (1997).
Smits et al., "Prion Protein and Scrapie Susceptibility," *Vet. Quart.* 19(3):101-105 (1997).
Solomon and et al., "Modulation of The Catalytic Pathway of Carboxypeptidase A by Conjugation with Polyvinyl Alcohols," *Adv. Mol. Cell Biology*15A:33-45 (1996).
Solomon et al., "Activity of monoclonal antibodies in prevention of in vitro aggregation of their antigens," *Immunotechnology*, 2(4):305 (1996).
Solomon et al., "Disaggregation of Alzheimer β-amyloid by site-directed mAb," *PNAS*, 94:4109-4112 (1997).
Solomon et al., "Monoclonal antibodies inhibit in vitro fibrillar aggregation of the Alzheimer β-amyloid peptide," *PNAS*, 93:452-455 (1996).
Solomon et al., "The Amino Terminus of the β-Amyloid Peptide Contains an Essential Epitope for Maintaining Its Solubility," from *Progress in Alzheimer's and Parkinson's Diseases*, edited by Fisher et al., Plenum Press, New York, pp. 205-211 (1995).
Solomon, A., "Pro-Rx (Protein Therapeutics)," University of Tennessee Medical Center (publication date unknown).
Solomon, B., "New Approach Towards Fast Induction of Anti β-Amyloid Peptide Immune Response," Department of Molecular Microbiology & Biotechnology, Tel-Aviv University, Ramat Aviv, Tel-Aviv, Israel (publication date unknown).
Solomon, B., "Immunological approaches as therapy for Alzheimer's disease " *Expert Opin. Biol. Ther.*, 2(8):907-917 (2002).
Solomon, B., "Generation and brain delivery of anti-aggregating antibodies against β-amyloid plaques using phage display technology," *J. Neural Transm. Suppl.*, 62:321-325 (2002).
Solomon, B., "Immunotherapeutic strategies for prevention and treatment of Alzheimer's disease," *DNA and Cell Biology*, 20(11):697-703 (2001).
Solomon et al., "Fast induction of anti-β-amyloid peptide immune response," *Research and Practice in Alzheimer's Disease*, 6:260-264 (2002).
Soto et al., "Beta sheet breaker peptides inhibit fibrillogenesis in a rat brain model of amyloidosis: implications for Alzheimer's therapy," *Nature Medicine.*, 4(7):822-826 (1998).

(56) References Cited

OTHER PUBLICATIONS

Soto et al., "The α-helical to β-strand transition in the amino-terminal fragment of the amyloid β-peptide modulates amyloid formation," *J. Biol. Chem*, 270(7):3063-3067 (1995).
Soto et al., "The conformation of Alzheimer's beta peptide determines the rate of amyloid formation and its resistance to proteolysis," *Biochem. J.*, 314:701-707 (1996).
Souder et al., "Overview of Alzheimer's disease," *Nurs. Clin. N. Am.*, 39:545-559 (2004).
Southwick et al., "Assessment of Amyloid β protein in Cerebrospinal fluid as an Aid in the Diagnosis of Alzheimer's Disease," *J. Neurochemistry*, 66:259-265 (1996).
Spellerberg et al., "DNA Vaccines Against Lymphoma," Journal of Immunology, 159:1885-1892 (1997).
Spooner et al., "The generation and characterization of potentially therapeutic Aβ antibodies in mice: differences according to strain and immunization protocol," *Vaccine*, 21:290-297 (2002).
St. George-Hyslop et al., "Antibody clears senile plaques," *Nature*, 40:116-117 (1999).
Staunton et al., "Primary structures of ICAM-1 demonstrates interaction between members of the immunoglobulin and intergrin supergene families," *Cell* 52(6):925-33 (1988), abstract only.
Stein et al., "Lack of Neurodegeneration in Transgenic Mice Overexpressing Mutant Amyloid Precursor Protein is Associated with Increased Levels of Transthyretin and Activation of Cell Survival Pathways," *The Journal of Neuroscience*, 22(17):7380-7388 (2002).
Stern et al., "Antibodies to the β-amyloid peptide cross-react with conformational epitopes in human fibrinogen subunits from peripheral blood," *FEBS Letters*, 264(1):43-47 (1990).
Stoute et al., "A Preliminary Evaluation of a Recombinant Circumsporozoite Protein Vaccine Against *Plasmodium Falciparum Malaria*", *N. Engl. J. Med.*, 336(2):86-91 (1997).
Strbak et al., "Passive Immunization and Hypothalamic Peptide Secretion", *Neuroendocrinology*, 58:210-217 (1993).
Sturchler-Pierrat et al., "Two amyloid precursor protein transgenic mouse models with Alzheimer disease-like pathology," *PNAS*, 94:13287-13292 (1997).
Su et al., "Intravascular infusions of soluble β-amyloid compromise the blood-brain barrier, activate CNS Glial cells and induce peripheral hemorrhage," *Brain Research*, 818:105-107 (1999).
Suo et al., "Soluble Alzhelmers β-amyloid constricts the cerebral vasculature in vivo" *Neuroscience Letters*, 257:77-80 (1998).
Supplementary Partial European Search Report of Apr. 10, 2007 for European Application 04720353.4-1222.
Szendrei, et al., "The effects of aspartic acid-bond isomerization on in vitro properties of the amyloid β-peptide as modeled with N-terminal decapeptide fragments" *Int. J. Peptide Protein Res.*, 47:289-296 (1996).
Tabaton et al., "Soluble amyloid β-protein is a marker of Alzheimer amyloid in brain but not in cerebrospinal fluid," *Biochem. and Biophys. Res. Comm.*, 200(3):1598-1603 (1994).
Tal et al., "Complete Freund's Adjuvant Immunization Prolongs Survival in Experimental Prion Disease in Mice," *Journal of Neuroscience Research*, 71:286-290 (2003).
Tan et al., "Amyloidosis," *Histopathology*, 25:403-414 (1994).
Tanaka et al., "NC-1900, an active fragment analog of arginine vasopressin, improves learning and memory deficits induced by beta-amyloid protein in rats," *European J. Pharmacology*, 352:135-142 (1998).
Tang et al., "Genetic immunization is a siple method for eliciting an immune response," *Nature*, 356:152-154 (1992).
Teller et al., "Presence of soluble amyloid β-peptide precedes amyloid plaque formation in Down's syndrome" *Nature Medicine*, 2(1):93-95 (1996).
Tennent et al., "Serum amyloid P component prevents proteolysis of the amyloid fibrils of Alzheimer's disease and systemic amyloidosis," *PNAS*, 92:4299-4303 (1995).
Thorsett, E.D. et al., "Therapeutic approaches to Alzheimer's disease," *Curr. Op. in Chem. Biology*, 4:377-382 (2000).

Tjernberg et al., "A molecular model for Alzheimer amyloid β-peptide fibril formation," *J. Biol. Chem.*, 274(18):12619-12625 (1999).
Tjernberg et al., "Arrest of β-amyloid fibril formation by a pentapeptide ligand," *J. Biol. Chem.*, 271:8545-8548 (1996).
Tjernberg, et al, "Controlling amyloid beta-peptide fibril formation with protease-stable ligands," *J. Biol Chem.*, 272(19):12601-12605 (1997).
Town et al., "Characterization of murine immunoglobulin G antibodies against human amyloid-$β_{1-42}$" *Neurosci. Lett*, 307:101-104 (2001).
Travis, J., "A Vaccine for Alzheimer's Disease?®," *Science News Online*, 156(2) pp. 1-3 downloaded from internet (1999).
Travis, J., "Saving the Mind Faces High Hurdles," *Science*, 309:731-734 (2005).
Trieb et al., "Is Alzheimer beta amyloid precursor protein (APP) an autoantigen? Peptides corresponding to parts of the APP sequence stimulate T lymphocytes in normals, but not in patients with Alzheimer's disease," *Immunobiology*, 191(2-3):114-115 Abstract C.37, (1994).
Trieb et al., "APP Peptides Stimulate Lymphocyte Proliferation in Normals, But Not in Patients With Alzheimer's Disease," *Neurobiology of Aging*, 17(4):541-547 (1996).
Tsuzuki et al., "Amyloid β protein in rat soleus in choroquine-induced myopthy using end-specific antibodies for Aβ40 and Aβ42: immunohistochemical evidence for amyloid βprotein," *Neuroscience Letters*, 2002:77-80 (1995).
Ulvestad et al., "Fc Receptors for IgG on Cultured Human Microglia Mediate Cytotoxicity and Phagocytosis of Antibody-coated Targets," *Journal of Neuropathology and Experimental Neurology*, 53(1):27-36 (1994).
UniProtKB/Swiss-Prot entry P18525, pp. 1-3 downloaded from http://www.expasy.org/cgi-bin/niceprot.pl/printable?ac=P18525 on Feb. 8, 1997, "HV54_Mouse" (Nov. 1, 1990).
Urmoneit et al., "Cerebrovascular Smooth Muscle CElls Internalize Alzheimer Amyloid Beta Protein via a Lipoprotein Pathway: Implications for Cerebral Amyloid Angiopathy," *Laboratory Investigation*, 77(2):157-166 (1997).
U.S. Appl. No. 09/316,387, Office Action mailed Sep. 10, 2007.
U.S. Appl. No. 09/316,387, Response to Jun. 20, 2005 Office Action filed Dec. 20, 2005.
U.S. Appl. No. 09/316,387, Declaration of Solomon, Hrncic, and Wall under 37 C.F.R. § 1.131 filed Mar. 6, 2006.
U.S. Appl. No. 09/316,387, Office Action mailed Jun. 20, 2005.
Vajdos et al., "Comprehensive Functional Maps of the Antigen-binging site of an Anti_ErbB2 Antibody Obtained with Shotgun Scanning Mutagenesis," *J. Mol. Biol.* 320:415-428 (2002).
Valleix et al., "Hereditary renal amyloidosis caused by a new variant lysozyme W64R in a French family," *Kidney International*, 61:907-912 (2002).
Van Den Dobbelsteen et al., "Characteristics of Immune Responses to Native and Protein Conjugated Pneumococcal Polysaccharide Type 14," *Scand. J. Immunol.*, 41:273-280 (1995).
Van Gool et al., "Concentrations of amyloid-β protein in cerebrospinal fluid increase with age in patients free from neurodegenerative disease," *Neuroscience Letters*, 172:122-124 (1994).
Van Leuven, F., "Single and multiple transgenic mice as models for Alzheimer's disease," *Progress in Neurobiology*, 61:305-312 (2000).
Van Regenmortel et al, "D-peptides as immunogens and diagnostic reagents " *Curr. Opin. Biotechnol.*, 9(4):377-382 (1998).
Vanderstichele et al., "Standardization of Measurement of B-amyloid(1-42) in Cerebrospinal Fluid and Plasma:," *Int. J. Exp. Clin. Invest.*, 7(4):245-258 (2000).
Vehmas et al., "Beta-Amyloid peptide vaccination results in marked changes in serum and brain Abeta levels in APPswe/PS1 DeltaE9 mice, as detected by SELDI-TOF-based ProteinChip® technology," *DNA Cell Biol.*, (11):713-721 (2001).
Velazquez et al., "Aspartate residue 7 in amyloid β-protein is critical for classical complement pathway activation: Implications for Alzheimer's disease pathogenesis," *Nature Medicine*, 3(1):77-79 (1997).

(56) References Cited

OTHER PUBLICATIONS

Verbeek et al., "Accumulation of Intercellular Adhesion Molecule-1 in Senile Plaques in Brain Tissue of patients with Alzheimer's Disease," *Amer. Journ. Pathology*, 144(1):104-116 (1994).
Verma et al., "Gene therapy—promises, problems and prospects," *Nature*, 389:239-242 (1997).
Vershigora A. E. Obshchaya Immynologiya, pp. 35, 229-231 and 152-153 (1990).
Vickers, J. C., "A Vaccine Against Alzheimer's Disease," *Drugs Aging*, 19(7):487-494 (2002).
Vidanovic et al., "Effects of nonionic surfactants on the physical stability of immunoglobulin G in aqueous solution during mechanical agitation," *Die Pharmazie*, 58(6):399-404 (2003).
Walker et al., "Labeling of Cerebral Amyloid in Vivo with a Monoclonal Antibody," *J. Neuropath. Exp. Neurology*, 53(4):377-383 (1994).
Walsh et al., "Naturally secreted oligomers of amyloid β protein potently inhibit hippocampal long-term potentiation in vivo," *Nature*, 416(6880):535-539 (2002).
Wang et al., "The levels of soluble versus insoluble brain Aβ distinguish Alzheimer's disease from normal and pathologic aging," *Experimental Neurology*, 158:328-337 (1999).
Wang et al., "Soluble oligomers of β amyloid (1-42) inhibit long-term potentiation but not long-term depression in rate dentate gyrus," *Brain Research*, 924:133-140 (2002).
Wang, W., "Instability, stabilization, and formulation of liquid protein pharmaceuticals" *Int. J. Pharmaceutics*, 185(2):129-188 (1999).
Washington University in St. Louis School of Medicine, "Study gives Clues to Working of Anti-Alzheimer Antibody," downloaded from www.medicine.wustl.edu/~wumpa/news on Dec. 15, 2004.
*Webster's New World Dictionary*, p. 1387, therapeutic (1988).
*Webster's New World Dictionary of American English*, Third College Edition, p. 1078 (1988).
Weiner et al., "Nasal administration of amyloid-β peptide decreases cerebral amyloid burden in a mouse model of Alzheimer's disease," *Annals of Neurology*, 48:567-579 (2000).
Weiner et al., "Oral Tolerance: Immunologic Mechanisms and Treatment of Animal and Human Organ-Specific Autoimmune Diseases by Oral Administration of Autoantigens," *Annu. Rev. Immunol.*, 12:809-837 (1994).
Weiner, H. L., "Oral tolerance: immune mechanisms and treatment of autoimmune diseases," *Immunology Today*, 18:335-343 (1997).
Weinreb et al., "NACP, A Protein Implicated in Alzheimer's Disease and Learning, Is Natively Unfolded," *Biochemistry*, 35(43):13709-13715 (1996).
Weissmann et al., "Bovine spongiform encephalopathy and early onset variant Creutzfeldt-Jakob disease," *Curr. Opin. Neurobiol.*, 7:695-700 (1997).
Weldon et al., "Neurotoxicity of Aβ Peptide: Confocal Imaging of Cellular Changes Induced by -Amyloid in Rat CNS in Vivo," *Society for Neuroscicence Abstracts*, 22(Part 1) (1996).
Wells, J. A., "Additivity of Mutational Effects in Proteins," *Biochemistry*, 29(37):8509-8517 (1990).
Wen, G.Y., "Alzheimer's Disease and Risk Factors," *J. Food Drug Analysis*, 6(2):465-476 (1998).
Wengenack et al., "Targeting Alzheimer amyloid plaques in vivo," *Nature Biotech.*, 18:868-872 (2000).
White et al., "Immunotherapy as a therapeutic treatment for neurodegenerative disorders," *J. Neurochem.*, 87(4):801-808 (2003).
Wikipedia definition of "epitope" printed from internet on Apr. 26, 2006.
Wikipedia definition of "antigen" printed from internet on Apr. 26, 2006.
Wikipedia definition of "route of administration including parenteral" printed from internet on Apr. 26, 2006.
Wilson et al., "Phage display: applications, innovations, and issues in phage and host biology," *Can. J. Microbiol*, 44:313-329 (1998).
Winblad et al., "Hints of a therapeutic Vaccine for Alzheimer's?" *Neuron*, 38:517-519 (2003).
Winter et al., "Humanized antibodies" *Immunology Today*, 14(6):243-246 (1996).
Wisconsin Alumni Research Foundation, "Injection of Newborn Mice with Seven Chemical Adjuvants to Help Determine Their Safety in Use in Biologicals", U.S. Govt. Res. Develop. Rep., 70(24), 56 (1969).
Wisniewski et al., "Alzheimer's disease and soluble A beta," *Neurobiol. Aging*, 15(2):143-52.
Wisniewski et al., "Therapeutics in Alzheimer's and Prion Diseases," *Biochemical Society Transactions*, 30(4):574-587 (2002).
Whitcomb et al., "Characterization of saturable binding sites for circulating pancreatic polypeptide in rat brain," *Am J Pysiol Gastrointest Liver Physiol*, 259:G687-G691 (1990).
Wong et al., "Neuritic Plaques and Cerebrovascular Amyloid in Alzheimer Disease are Antigenically Related," *PNAS*, 82:8729-8732 (1985).
Wood et al., "Amyloid precursor protein processing and Aβ42 deposition in a transgenic mouse model of Alzheimer disease," *PNAS*, 94:1550-1555 (1997).
Wood et al., "Prolines and amyloidogenicily in fragments of the Alzheimer's peptide β/A4" *Biochemistry*, 34:724-730 (1995).
Wu et al., "Humanization of a Murine Monoclonal Antibody by Simultaneous Optimization of Framework and CDR Residues," *J. Mol. Biol.*, 294:151-162 (1999).
Wu et al., "Expression of immunogenic epitopes of hepatitis B surface antigen with hybrid flagellin proteins by a vaccine strain of *Salmonella*," *PNAS*, 86:4726-4730 (1989).
Wu, et al., "Drug targeting of a peptide radiopharmaceutical through the primate blood-brain barrier in vivo with a monoclonal antibody to the human insulin receptor," *J. Clin. Invest.*, 100:1804-1812 (1997).
Wu et al., "An Analysis of the Sequences of the Variable Regions of Bence Jones Proteins and Myeloma Light Chains and their Implications for Antibody Complementarity*," *J. Exp. Med.*, 132:211-250 (1970).
Wyeth, Annual Review 2005: Creating Value . . . Advancing Health (Feb. 27, 2006).
Xiang et al., "Manipulation of the immune response to a plasmid-encoded viral antigen by coinoculation with plasmids expressing cytokines," *Immunity*, 2(2):129-135 Abstract (1995).
Xu et al., "Increased incidence of anti-β-amyloid autoantibodies secreted by Epstein-Barr virus transformed B cell lines from patients with Alzheimer's disease," *Mechanisms of Ageing and Development*, 94:213-222 (1997).
Yamada et al., "Generation and Characterization of Rat Monoclonal Antibodies Against Human Serum Amyloid A," *Scand. J. Immunol.*, 46(2):175-179 (1997).
Yamaguchi et al., Diffuse plaques associated with astroglial amyloid β protein, possibly showing a disappearing stage of senile plaques, *Acta Neuropathol.*, 95:217-222 (1998).
Yang et al., "Effects of Racemization on the Aggregational Properties of the Amyloid β-Peptide in Alzheimer's Disease," abstract # 255 from American Chemical Society 214th National Meeting (1997).
Yankner et al., "Neurotrophic and Neurotoxic effects of Amyloid β Protein: Reversal by Tachykinin Neuropeptides," *Science*, 250:279-282 (1990).
Younkin, "Amyloid β vaccination: reduced plaques and improved cognition," *Nature Medicine*, 7:18-19 (2001).
Zameer et al., "Single Chain Fv Antibodies against 25-35 Peptide Fragment of Amyloid-β: Potential Therapeutic for Alzheimer's Disease," Abstract P4-420, p. S593, presented at Poster Session P4:Therapeutics and Therapeutic Strategies-Therapeutic Strateies, Amyloid-Based, also *Neurobiology of Aging*, 25(Suppl. 2): p. S593 (Jul. 2004).
Zhang et al., "Specialized Applications, Purification of Recombinant Proteins and Study of Protein Interaction by Epitope Tagging," *Current Protocols in Mol. Biol.*, Supp 41, pp. 10.15.1 through 10.15.9 (1998).
Zhang et al., "A novel recombinant adeno-associated virus vaccine reduces behavioral impairment and β-amyloid plaques in a mouse model of Alzheimer's disease," *Neurobiology of Disease*, 14:365-379 (2003).
Zlokovic et al., "Clearance of amyloid β-peptide from brain: transport or metabolism?," *Nature Medicine*, 6(7):718-719 (2000).

(56) References Cited

OTHER PUBLICATIONS

Zlokovic et al., "Glycoprotein 330/megalin: probable role in receptor-mediated transport of apolipoprotein J alone and in a complex with Alzheimer disease amyloid beta at the blood-brain and blood-cerebrospinal fluid barriers," *PNAS*, 93(9):4229-4334 (1996) abstract only.
U.S. Appl. No. 12/297,636, Office Action mailed Oct. 15, 2012.
U.S. Appl. No. 13/076,379, Office Action mailed Nov. 28, 2012.
U.S. Appl. No. 13/123,898, Office Action mailed Jul. 20, 2012.
U.S. Appl. No. 13/271,081, Office Action mailed Mar. 1, 2013.
Andrews, et al., "Amino acid sequence of the variable regions of heavy chains from two idiotypically cross-reactive human IgM anti-gamma-globulins of the Wa group", *Biochemistry*, Sep. 29, 1981;20(20):5822-5830.
Andrews, et al., "Complete amino acid sequence of variable domains from two monoclonal human anti-gamma globulins of the Wa cross-idiotypic group: Suggestion that the J segments are involved in the structural correlate of the idiotype", *Proc. Natl. Acad. Sci. USA*, vol. 78, No. 6, pp. 3799-3803, Jun. 1981.
Capra, et al., "Structure of Antibodies with Shared Idiotypy: The Complete Sequence of the Heavy Chain Variable Regions of Two Immunoglobulin M Anti-Gamma Globulins", *Proc. Nat. Acad. Sci. USA*, vol. 71, No. 10, pp. 4032-4036, Oct. 1974.
Castillo, "Poor results halt production, studies on promising Alzheimer's drug bapineuzumab" *CBS Interactive Inc.*, Nov. 7, 2012 pp. 1/1.
Centers for Disease Control and Prevention, "Vaccine Safety" Retrieved from www.cdc.gov/vaccinesafety/concerns/adjuants.html (Oct. 18, 2012) p. 1-2.
Dohi et al., "Reactivity of a Mouse/Human Chimeric Anti-GM2 Antibody KM966 with Brain Tumors" *Anticancer Research*, 14:2577-2582 (1994).
Eli Lilly, "Eli Lilly and Company Announces Top-Line Results on Solanezumab Phase 3 Clinical Trials in Patients with Alzheimer's Disease" Press Release, Aug. 24, 2012.
European Extended Search Report of Dec. 6, 2011 for European Application 10183051.1.
Geeraedts et al., "Superior Immunogenicity of Inactivated Whole Virus H5N1 Influenza Vaccine is Primarily Controlled by Toll-like Receptors Signalling", *PLoS Pathogens*, 2008, 4:1-8.
Gluck et al., "Immunopotentiating Reconstituted Influenza Virus Virosome Vaccine Delivery System for Immunization against Hepatitis A", *J. Clin. Invest*,,(1992) vol. 90:2491-2495.
Gluck, "Immunopotentiating reconstituted influenza virosomes (IRIVs) and other adjuvants for improved presentation of small antigens", *Vaccine*, vol. 10, Issue 13 (1992) 915-919.
Hagen, Declaration Oct. 31, 2011.
Johnson & Johnson, "Johnson & Johnson Announces Discontinuation of Phase 3 Development of Bapineuzumab Intravenous (IV) In Mild-to-Moderate Alzheimer's Disease", Press Release, Aug. 6, 2012.
Kerchner, et al., "Bapineuzumab", NIH Public Access, Expert Opin Biol Ther., 10(7) 1121-1130 Jul. 2010.
Laino, "Cerebral Edema Common, but Found to Be Manageable, With Bapineuzumab", *Neurology Today*, Aug. 19, 2011.
Lee et al., "Aspects of Immunobiology and Immunotherapy and Uses of Monoclonal Antibodies and Biologic Immune Modifiers in Human Gliomas" *Neurologic Clinics*, vol. 3, No. 4, Nov. 1985, 901-917.
Lemere et al., "Amyloid-Beta Immunotherapy for the Prevention and Treatment of Alzheimer Disease: Lessons from Mice, Monkeys, and Humans", Rejuvenation Research 9(1):77-84 (2006).
Marx et al., "The Possible Role of the Immune System in Alzheimer's Disease" *Exp Gerontology*, vol. 33, Nos. 7/8 pp. 871-881, 1998.
Miller et al., "Comparative efficacy of two immunocontraceptive vaccines" *Vaccine*, (1997) 15(17-18):1858-1862 (abstract only).
Pfizer Announces Co-Primary Clinical Endpoints Not Met in Second Phase 3 Bapineuzumab Study in Mild-to-Moderate Alzheimer's Disease Patients Who Do Not Carry the Apoe4 Genotype, Press Release, Aug. 6, 2012.
Pfizer, "Pfizer Announces Topline Results of First of Four Studies in Bapineuzumab Phase 3 Program", Press Release, Jul. 23, 2012.
Remes et al., "Hereditary dementia with intracerevbral hemorrhages and cerebral amyloid angiopathy". *Neurology* 63(2):234-240 (2004).
Rivero et al., "Suppression of experimental autoimmune encephalomyelitis (EAE) by intraperitoneal administration of soluble myelin antigens in Wistar rats" *J. Neuroimmunology*, (1997) 72, 3-10.
Solomon, "Alzheimer's Disease and Immunotherapy", *Current Alzheimer Research*, 2004, 1, 149-163.
Solomon, "Beta-Amyloid-Based Immunotherapy as a Treatment of Alzheimer's Disease", *Drugs of Today*, 2007, 43(5):333-342.
Spack, "Antigen-specific therapies for the treatment of multiple sclerosis: a clinical trial update", *Exp. Opin. Invest. Drugs*, (1997) 6(11):1715-1727.
Triozzi et al., "Effects of a beta-human chorionic gonadotropin subunit immunogen adminstered in aqueous solution with a novel nonionic block copolymer adjuvant in patients with advanced cancer", *Clin. Cancer Res.*, (1997) 3(12 pt 1):2355-2362 (abstract only).
Wick et al., "The Aging Immune System: Primary and Secondary Alterations of Immune Reactivity in the Elderly" *Exp. Geronology*, vol. 32, Nos. 4/5, pp. 401-413, 1997.
U.S. Appl. No. 12/608,869, Advisory Action mailed Mar. 13, 2013.
U.S. Appl. No. 12/608,869, Office Action mailed Aug. 23, 2012.
U.S. Appl. No. 12/977,013, Office Action mailed Sep. 14, 2012.
U.S. Appl. No. 12/738,396, Office Action mailed Sep. 21, 2012.

\* cited by examiner

Figure 1 — Predicted Amino Acid Sequences of AAB-001 Light and Heavy Chains

LIGHT CHAIN

```
1    DVVMTQSPLS LPVTPGEPAS ISCKSSQSLL DSDGKTYLNW LLQKPGQSPQ
51   RLIYLVSKLD SGVPDRFSGS GSGTDFTLKI SRVEAEDVGV YYCWQGTHFP
101  RTFGQGTKVE IKRTVAAPSV FIFPPSDEQL KSGTASVVCL LNNFYPREAK
151  VQWKVDNALQ SGNSQESVTE QDSKDSTYSL SSTLTLSKAD YEKHKVYACE
201  VTHQGLSSPV TKSFNRGEC
                    → Heavy Chain
```

HEAVY CHAIN

```
1    EVQLLESGGG LVQPGGSLRL SCAASGFTFS NYGMSWVRQA PGKGLEWVAS
51   IRSGGGRTYY SDNVKGRFTI SRDNSKNTLY LQMNSLRAED TAVYYCVRYD
101  HYSGSSDYWG QGTLVTVSSA STKGPSVFPL APSSKSTSGG TAALGCLVKD
151  YFPEPVTVSW NSGALTSGVH TFPAVLQSSG LYSLSSVVTV PSSSLGTQTY
201  ICNVNHKPSN TKVDKKVEPK SCDKTHTCPP CPAPELLGGP SVFLFPPKPK
        Light Chain ←           → Heavy Chain
251  DTLMISRTPE VTCVVVDVSH EDPEVKFNWY VDGVEVHNAK TKPREEQYNS
301  TYRVVSVLTV LHQDWLNGKE YKCKVSNKAL PAPIEKTISK AKGQPREPQV
351  YTLPPSREEM TKNQVSLTCL VKGFYPSDIA VEWESNGQPE NNYKTTPPVL
401  DSDGSFFLYS KLTVDKSRWQ QGNVFSCSVM HEALHNHYTQ KSLSLSPG(K)
```

Month 4 MMSE Change from Baseline

| Dose | n | Mean | Median | SD |
|---|---|---|---|---|
| Placebo | 8 | -0.63 | -1.0 | 2.446 |
| 0.5 mg/kg | 6 | 1.50 | 1.5 | 2.739 |
| 1.5 mg/kg | 6 | 2.00 | 1.5 | 1.789 |
| 5.0 mg/kg | 9 | -0.67 | 0.0 | 4.555 |

Fig. 4

Statistical Testing: Month 4 MMSE Change from Baseline

- Primary SAP Specified Analysis:
  - Test of linear trend: p=0.3840
- Additional Analyses:

| Method | Placebo (n=8) vs. 0.5 mg/kg (n=6) | Placebo (n=8) vs. 1.5 mg/kg (n=6) | Placebo (n=8) vs. 0.5 +1.5 mg/kg (n=12) |
|---|---|---|---|
| Unadjusted ANCOVA | 0.152 | 0.047 | 0.037 |
| ANCOVA adjusted for baseline MMSE | 0.199 | 0.018 | 0.0499 |
| Mann-Whitney Test (non-parametric) | 0.172 | 0.069 | 0.057 |

Fig. 5

Figure 6. Simulated steady state prediction across a range of doses (0.05–0.25 mg/kg) of SQ AAB-001 at projected bioavailability level of 70% (biweekly dosing)

Study 201: Mean Serum AAB-001 Concentration vs. Time Profiles after IV Administration

Figure 10

Study 201: IV AAB-001 PK Parameters

INFUSION #1

| AAB-001 Dose | Parameter | $C_{max}$ (µg/mL) | | | $t_{max}$ (h) | $AUC_{inf}$ (µg·h/mL) | CL (mL/h/kg) | Vz (mL/kg) | $t_{1/2}$ (days) |
|---|---|---|---|---|---|---|---|---|---|
| 0.15 mg/kg (Cohort 2) | n Mean (SD) | 6 4.60 (0.61) | | | 6 1.5 (median) | 6 1897 (255) | 6 0.06 (0.01) | 6 56.49 (22.27) | 6 26.65 (9.07) |
| 0.5 mg/kg (Cohort 1) | n Mean (SD) | 6 17.20 (5.34) | | | 6 1.75 (median) | 6 7578 (1717) | 6 0.05 (0.01) | 6 45.87 (8.44) | 6 26.26 (7.07) |
| 1.0 mg/kg (Cohort 3) | n Mean (SD) | 6 28.04 (4.59) | | | 6 1.99 (median) | 6 14135 (4373) | 6 0.06 (0.02) | 6 58.13 (11.43) | 6 28.50 (6.07) |
| 2.0 mg/kg (Cohort 4) | n Mean (SD) | 3 63.17 (11.28) | | | 3 1.99 (median) | NE | NE | NE | NE |

INFUSION #3

| AAB-001 Dose | Parameter | $C_{max}$ (µg/mL) | $C_{avg}$ (µg/mL) | $C_{min}$ (µg/mL) | $t_{max}$ (h) | $AUC_{tau}$ (µg·h/mL) | CL (mL/h/kg) | Vz (mL/kg) | $t_{1/2}$ (days) |
|---|---|---|---|---|---|---|---|---|---|
| 0.15 mg/kg (Cohort 2) | n Mean (SD) | 6 4.42 (0.93) | 6 1.08 (0.24) | 6 0.11 (0.04) | 6 1.00 (median) | 6 2364 (517) | 6 0.05 (0.02) | 6 34.65 (13.31) | 6 21.13 (2.87) |
| 0.5 mg/kg (Cohort 1) | n Mean (SD) | 4 17.04 (5.09) | 4 3.28 (1.26) | 4 0.76 (0.52) | 4 1.24 (median) | 4 7164 (2755) | 4 0.05 (0.02) | 4 42.42 (13.67) | 4 23.75 (8.81) |
| 1.0 mg/kg (Cohort 3) | n Mean (SD) | 4 32.13 (2.36) | 4 5.65 (2.79) | 3 2.82 (1.17) | 4 1.73 (median) | 2 16869 (5319) | 2 0.05 (0.02) | 2 50.40 (9.48) | 2 34.01 (8.68) |

NE = Not evaluable

Study 201: Plasma Aβ Levels (PD Effect)

TREATMENT OF AMYLOIDOGENIC DISEASES

BACKGROUND OF THE INVENTION

Alzheimer's disease (AD) is a progressive disease resulting in senile dementia. See generally Selkoe, *TINS* 16:403 (1993); Hardy et al., WO 92/13069; Selkoe, *J. Neuropathol. Exp. Neurol.* 53:438 (1994); Duff et al., *Nature* 373:476 (1995); Games et al., *Nature* 373:523 (1995). Broadly speaking, the disease falls into two categories: late onset, which occurs in old age (65+ years) and early onset, which develops well before the senile period, i.e., between 35 and 60 years. In both types of disease, the pathology is the same but the abnormalities tend to be more severe and widespread in cases beginning at an earlier age. The disease is characterized by at least two types of lesions in the brain, neurofibrillary tangles and senile plaques. Neurofibrillary tangles are intracellular deposits of microtubule associated tau protein consisting of two filaments twisted about each other in pairs. Senile plaques (i.e., amyloid plaques) are areas of disorganized neuropil up to 150 μm across with extracellular amyloid deposits at the center which are visible by microscopic analysis of sections of brain tissue. The accumulation of amyloid plaques within the brain is also associated with Down's syndrome and other cognitive disorders.

The principal constituent of the plaques is a peptide termed Aβ or β-amyloid peptide. Aβ peptide is a 4-kDa internal fragment of 39-43 amino acids of a larger transmembrane glycoprotein named protein termed amyloid precursor protein (APP). As a result of proteolytic processing of APP by different secretase enzymes, Aβ is primarily found in both a short form, 40 amino acids in length, and a long form, ranging from 42-43 amino acids in length. Part of the hydrophobic transmembrane domain of APP is found at the carboxy end of Aβ, and may account for the ability of Aβ to aggregate into plaques, particularly in the case of the long form. Accumulation of amyloid plaques in the brain eventually leads to neuronal cell death. The physical symptoms associated with this type of neural deterioration characterize Alzheimer's disease.

Several mutations within the APP protein have been correlated with the presence of Alzheimer's disease. See, e.g., Goate et al., *Nature* 349:704 (1991) (valine$^{717}$ to isoleucine); Chartier Harlan et al. *Nature* 353:844 (1991)) (valine$^{717}$ to glycine); Murrell et al., *Science* 254:97 (1991) (valine$^{717}$ to phenylalanine); Mullan et al., *Nature Genet.* 1:345 (1992) (a double mutation changing lysine$^{595}$-methionine$^{596}$ to asparagine$^{595}$-leucine$^{596}$). Such mutations are thought to cause Alzheimer's disease by increased or altered processing of APP to Aβ, particularly processing of APP to increased amounts of the long form of Aβ (i.e., Aβ1-42 and Aβ1-43). Mutations in other genes, such as the presenilin genes, PS1 and PS2, are thought indirectly to affect processing of APP to generate increased amounts of long form Aβ (see Hardy, *TINS* 20: 154 (1997)).

Mouse models have been used successfully to determine the significance of amyloid plaques in Alzheimer's (Games et al., supra, Johnson-Wood et al., *Proc. Natl. Acad. Sci. USA* 94:1550 (1997)). In particular, when PDAPP transgenic mice, (which express a mutant form of human APP and develop Alzheimer's disease at a young age), are injected with the long form of Aβ, they display both a decrease in the progression of Alzheimer's and an increase in antibody titers to the Aβ peptide (Schenk et al., *Nature* 400, 173 (1999)). The observations discussed above indicate that Aβ, particularly in its long form, is a causative element in Alzheimer's disease.

McMichael, EP 526,511, proposes administration of homeopathic dosages (less than or equal to $10^{-2}$ mg/day) of Aβ to patients with preestablished AD. In a typical human with about 5 liters of plasma, even the upper limit of this dosage would be expected to generate a concentration of no more than 2 pg/ml. The normal concentration of Aβ in human plasma is typically in the range of 50-200 pg/ml (Seubert et al., *Nature* 359:325 (1992)). Because EP 526,511's proposed dosage would barely alter the level of endogenous circulating Aβ and because EP 526,511 does not recommend use of an adjuvant, as an immunostimulant, it seems implausible that any therapeutic benefit would result.

Accordingly, there exists the need for new therapies and reagents for the treatment of Alzheimer's disease, in particular, therapies and reagents capable of effecting a therapeutic benefit at physiologic (e.g., non-toxic) doses.

CROSS-REFERENCE TO RELATED APPLICATIONS

U.S. Application No. 60/648,631 filed on Jan. 28, 2005; U.S. Publication No. US 20060193850 A1 published on Aug. 31, 2006; International Publication No. WO 06/083689 published on Aug. 10, 2006; U.S. Application No. 60/622,525 filed on Oct. 26, 2004 and, U.S. Publication No. US 20060160161 A1 published on Jul. 20, 2006 are related applications, all of which are incorporated by herein reference in their entirety for all purposes.

SUMMARY OF THE INVENTION

The invention provides methods of therapeutically treating Alzheimer's disease. The methods comprise administering by intravenous infusion to a patient suffering from the disease a dosage of an antibody within a range of about 0.5 mg/kg to less than 5 mg/kg. The antibody specifically binds to an N-terminal fragment of beta amyloid peptide (A13) with a binding affinity of at least $10^7$ M$^{-1}$, and thereby therapeutically treats the patient. Optionally, the antibody is a humanized antibody. Optionally, the humanized antibody is a humanized version of mouse antibody 3D6 expressed by the hybridoma deposited under ATCC under No. PTA-5130. Optionally, the humanized antibody comprises (i) a light chain comprising three complementarity determining regions (CDRs) from the immunological light chain variable region of the mouse antibody 3D6; and (ii) a heavy chain comprising three complementarity determining regions (CDRs) from the immunological heavy chain variable region of mouse antibody 3D6. Optionally, the humanized antibody comprises (i) a variable light chain region having the sequence as set forth in SEQ ID NO:1, SEQ ID NO:3 or SEQ ID NO:5; and (ii) a variable heavy chain region having the sequence as set forth in SEQ ID NO:2, SEQ ID NO:4 or SEQ ID NO:6. Optionally, the humanized antibody comprises (i) a variable light chain region having the sequence as set forth in SEQ ID NO:1 or SEQ ID NO:5; and (ii) a variable heavy chain region having the sequence as set forth in SEQ ID NO:2 or SEQ ID NO:6. Optionally, the humanized antibody is bapineuzumab. Optionally, the antibody is a humanized version of mouse antibody 10D5 expressed by the hybridoma deposited under ATCC under No. PTA-5129. Optionally, the humanized antibody comprises (i) a light chain comprising three complementarity determining regions (CDRs) from the immunological light chain variable region of the mouse antibody 10D5; and (ii) a heavy chain comprising three complementarity determining regions (CDRs) from the immunological heavy chain variable region of mouse antibody 10D5. Optionally, the humanized antibody comprises (i) a variable light chain region having the sequence as set forth in SEQ ID NO:7 or SEQ ID NO:28 as set forth in US Patent Publication No. 20050142131; and (ii) a variable heavy chain region having the sequence as set forth in SEQ ID NO:8 or SEQ ID NO:29 as set forth in US Patent Publication No. 20050142131. Optionally, the humanized antibody is a humanized version of mouse antibody 12A11 expressed by the hybridoma deposited under with the American Type Culture Collection (ATCC), Manassas, Va. 20108, USA on Apr. 8, 2003 under the terms of the Budapest Treaty and has deposit number PTA-7271.

Optionally, the humanized antibody comprises (i) a light chain comprising three complementarity determining regions (CDRs) from the immunological light chain variable region of the mouse antibody 12A11; and (ii) a heavy chain comprising three complementarity determining regions (CDRs) from the immunological heavy chain variable region of mouse antibody 12A11. Optionally, the humanized antibody comprises (i) a variable light chain region having the sequence as set forth in SEQ ID NO:2 as set forth in US Patent Publication No. 20050118651; and (ii) a variable heavy chain region having the sequence as set forth in SEQ ID NO:4 as set forth in US Patent Publication No. 20050118651. In some methods, the dosage is about 0.5 mg/kg. In some methods, the dosage is about 1.5 mg/kg. In some methods, the dosage is 0.5 to 3 mg/kg. In some methods, the dosage is 0.5 to 1.5 mg/kg. In some methods, the dosage is administered on multiple occasions, such as every 13 weeks.

Some methods further comprise monitoring the patient by at least one type of assessment selected from the group of consisting of Mini-Mental State Exam (MMSE), Alzheimer's Disease Assessment Scale—cognitive (ADAS-COG), Clinician Interview-Based Impression (CIBI), Neurological Test Battery (NTB), Disability Assessment for Dementia (DAD), Clinical Dementia Rating-sum of boxes (CDR-SOB), Neuropsychiatric Inventory (NPI), Positron Emission Tomography (PET Imaging) scan, Magnetic Resonance Imaging (MRI) scan, and measurement of blood pressure. In some methods, the type of assessment is an MMSE, and the MMSE is administered on multiple occasions, such as before administering the dosage, and at week 4, week 16, 6 months, and 1 year after administering the dosage. In some methods, the MMSE score measured after administration is higher than a previously assessed MMSE score.

The invention further provides methods of therapeutically treating Alzheimer's disease, comprising administering by intravenous infusion to a patient suffering from the disease a dosage of an antibody within a range of about 0.5 mg/kg to less than 5 mg/kg, wherein the antibody specifically binds to beta amyloid peptide (Aβ) with a binding affinity of at least $10^7$ $M^{-1}$, and monitoring the patient for posterior reversible encephalopathy syndrome (PRES) or vascular edema. Optionally, the monitoring comprises performing an MRI scan, optionally with a FLAIR (Fluid Attenuated Inversion Recovery) sequence imaging. In some methods, the monitoring identifies of at least one clinical symptom associated with PRES, such as headache, nausea, vomiting, confusion, seizures, visual abnormalities, altered mental functioning, ataxia, frontal symptoms, parietal symptoms, stupor, or focal neurological signs. In some methods, the dosage is reduced or suspended based on an outcome of the MRI scan that is indicative of PRES or vascular edema. In some methods, the dosage is reduced or suspended based on an outcome of the FLAIR sequence imaging that is indicative of PRES or vascular edema. In some methods, the dosage is reduced or suspended based on an identification of at least one clinical symptom associated with PRES. In some methods, the MRI scan is every 3 months, every 6 months, or every year. In some methods, the FLAIR sequence imaging is every 3 months, every 6 months, or every year.

Some of the above methods further comprise determining presence or absence of hypertension in the patient, wherein if the patient has hypertension, the method further comprises administering an antihypertensive. Optionally, the antihypertensive is selected from the group consisting of hydrochlorothiazide, angiotensin-converting enzyme (ACE) inhibitors, angiotensin II-receptor blockers (ARB), beta blockers, and calcium channel blockers.

Some methods further comprise administering a steroid to the patient to treat the PRES or vascular edema. Optionally, the steroid is dexamethasone or methyprednisolone.

Some methods further comprise reducing or suspending the dosage based on an outcome of the MRI scan and that is indicative of PRES or vascular and identifying at least one clinical symptom associated with PRES or vascular edema, such as headache, nausea, vomiting, confusion, seizures, visual abnormalities, altered mental functioning, ataxia, frontal symptoms, parietal symptoms, stupor, or focal neurological signs. Some methods further comprise reducing or suspending the dosage based on an outcome of the FLAIR sequence imaging that is indicative of PRES or vascular edema and identifying of at least one clinical symptom associated with PRES or vascular edema, such as headache, nausea, vomiting, confusion, seizures, visual abnormalities, altered mental functioning, ataxia, frontal symptoms, parietal symptoms, stupor, or focal neurological signs.

In some methods, the monitoring indicates presence of PRES or vascular edema at a first time point after administration, and absence of PRES or vascular edema at a second time point after the first point, and the patient is administered a first dosage before the monitoring indicates presence of PRES or vascular edema, a second dosage or no dosage after the monitoring detects presence of PRES or vascular edema, and a third dosage after the monitoring detects absence of PRES or vascular edema, wherein the first and third dosage are higher than the second dosage.

In some of the above methods, the antibody is a humanized antibody. Optionally, the humanized antibody is a humanized version of mouse antibody 3D6 expressed by the hybridoma deposited with the American Type Culture Collection (ATCC), Manassas, Va. 20108, USA on Apr. 8, 2003 under the terms of the Budapest Treaty and has deposit number PTA-5130.

Optionally, the humanized antibody comprises (i) a light chain comprising three complementarity determining regions (CDRs) from the immunological light chain variable region of the mouse antibody 3D6; and (ii) a heavy chain comprising three complementarity determining regions (CDRs) from the immunological heavy chain variable region of mouse antibody 3D6. Optionally, the humanized antibody comprises (i) a variable light chain region having the sequence as set forth in SEQ ID NO:1, SEQ ID NO:3 or SEQ ID NO:5; and (ii) a variable heavy chain region having the sequence as set forth in SEQ ID NO:2, SEQ ID NO:4 or SEQ ID NO:6. Optionally, the humanized antibody comprises (i) a variable light chain region having the sequence as set forth in SEQ ID NO:1 or SEQ ID NO:5; and (ii) a variable heavy chain region having the sequence as set forth in SEQ ID NO:2 or SEQ ID NO:6. Optionally, the humanized antibody is bapineuzumab.

In some of the above methods, the dosage is about 0.5 mg/kg. In some methods, the dosage is about 1.5 mg/kg. In some methods, the dosage is 0.5 to 3 mg/kg. In some methods, the dosage is 0.5 to 1.5 mg/kg. In some methods, the dosage is administered on multiple occasions, such as every 13 weeks.

In some of the above methods, Bapineuzumab is administered at a first dosage before PRES or vascular edema is determined from the MRI scan and a second dosage after PRES or vascular edema is determined from the MRI scan, and the second dosage is less then the first dosage. Optionally, the first dosage is 3-5 mg/kg and the second dosage is 0.5 to 3 mg/kg. Optionally, the second dosage is half of the first dosage. Optionally, the Bapineuzumab is administered at a first frequency before the MRI shows PRES or vascular edema and a second frequency after the MRI shows PRES or vascular edema, and the second frequency is less than the first frequency.

In some of the above methods, the type of assessment is blood pressure, and the presence or absence of hypertension is determined. Optionally, if the patient has hypertension, the method further comprises administering an antihypertensive. Optionally, the antihypertensive is selected from the group consisting of hydroclorothiazide, Angiotensin-converting Enzyme (ACE) Inhibitors, angiotensin II-receptor blockers (ARB), beta blockers, and calcium channel blockers.

The invention further provides therapeutic products. The products comprise a glass vial and instructions. The glass vial contains a formulation comprising about 10 mg to about 250 mg of a humanized anti Aβ antibody, about 4% mannitol or about 150 mM NaCl, about 5 mM to about 10 mM histidine, and about 10 mM methionine. The instructions to monitor a patient to whom the formulation is administered for PRES and or vascular edema are included with the products.

The invention provides methods method of treating Alzheimer disease comprising subcutaneously administering to a patient having the disease an antibody that specifically binds to an N-terminal fragment of Aβ, wherein the antibody is administered at a dose of 0.01-0.6 mg/kg and a frequency of between weekly and monthly. Optionally, the antibody is administered at a dose of 0.05-0.5 mg/kg. Optionally, the antibody is administered at a dose of 0.05-0.25 mg/kg. Optionally, the antibody is administered at a dose of 0.015-0.2 mg/kg weekly to biweekly. Optionally, the antibody is administered at a dose of 0.05-0.15 mg/kg weekly to biweekly. Optionally, the antibody is administered at a dose of 0.05-0.07 mg/kg weekly. Optionally, the antibody is administered at a dose of 0.06 mg/kg weekly. Optionally, the antibody is administered at a dose of 0.1 to 0.15 mg/kg biweekly. Optionally, the antibody is administered at a dose of 0.1 to 0.3 mg/kg monthly. Optionally, the antibody is administered at a dose of 0.2 mg/kg monthly.

The invention provides methods of treating Alzheimer disease comprising subcutaneously administering to a patient having the disease an antibody that specifically binds to an N-terminal fragment of Aβ, wherein the antibody is administered at a dose of 1-40 mg and a frequency of between weekly and monthly. Optionally, the antibody is administered at a dose of 5-25 mg. Optionally, the antibody is administered at a dose of 2.5-15 mg. Optionally, the antibody is administered at a dose of 1-12 mg weekly to biweekly. Optionally, the antibody is administered at a dose of 2.5-10 mg weekly to biweekly. Optionally, the antibody is administered at a dose of 2.5-5 mg weekly. Optionally, the antibody is administered at a dose of 4-5 mg weekly. Optionally, the antibody is administered at a dose of 7-10 mg biweekly.

The invention provides methods of treating Alzheimer disease, comprising administering to a patient having the disease an antibody that specifically binds to an N-terminal fragment of Aβ in a regime sufficient to maintain a maximum serum concentration of the antibody in the patient less than about 28 µg antibody/ml serum and thereby treating the patient. Optionally, the maximum serum concentration is within a range of about 4-28 µg antibody/ml serum. Optionally, the maximum serum concentration is within a range of about 4-18 µg antibody/ml serum. Optionally, the average serum concentration of the antibody in the patient is below about 7 µg antibody/ml serum. Optionally, the average serum concentration is within a range of about 2-7 µg antibody/ml serum. Optionally, the average serum concentration is about 5 µg antibody/ml serum. Optionally, the antibody is administered intravenously. Optionally, the antibody is administered subcutaneously. Optionally, a dose of 0.1-1.0 mg/kg is administered monthly. Optionally, a dose of 0.5-1.0 mg/kg is administered monthly. Optionally, the antibody is administered at a frequency between weekly and monthly. Optionally, the antibody is administered weekly or biweekly. Some methods further comprise measuring the concentration of antibody in the serum and adjusting the regime if the measured concentration falls outside the range. Optionally, the antibody is a humanized antibody. Optionally, the humanized antibody is a humanized version of mouse antibody 3D6 expressed by the hybridoma deposited under ATCC under No. PTA-5130. Optionally, the humanized antibody is bapineuzumab. Optionally, the humanized antibody is a humanized version of mouse antibody 10D5 expressed by the hybridoma deposited under ATCC under No. PTA-5129. Optionally, the humanized antibody is a humanized version of mouse antibody 12A11 expressed by the hybridoma deposited under ATCC under No. PTA-7271.

The invention provides methods of treating Alzheimer disease, comprising administering to a patient having the disease an antibody that specifically binds to an N-terminal fragment of Aβ in a regime sufficient to maintain an average serum concentration of the antibody in the patient below about 7 µg antibody/ml serum and thereby treat the patient. Optionally, the average serum concentration is within a range of about 2-7 µg antibody/ml serum. Optionally, the average serum concentration is about 5 µg antibody/ml serum. Optionally, the antibody is administered intravenously. Optionally, the antibody is administered subcutaneously. Optionally, a dose of 0.1-1.0 mg/kg is administered monthly. Optionally, a dose of 0.5-1.0 mg/kg is administered monthly. Optionally, the antibody is administered at a frequency between weekly and monthly. Optionally, the antibody is administered weekly or biweekly. Some methods further comprise measuring the concentration of antibody in the serum and adjusting the regime if the measured concentration falls outside the range. Optionally, the antibody is a humanized antibody. Optionally, the humanized antibody is a humanized version of mouse antibody 3D6 expressed by the hybridoma deposited under ATCC under No. PTA-5130. Optionally, the humanized antibody is bapineuzumab. Optionally, the humanized antibody is a humanized version of mouse antibody 10D5 expressed by the hybridoma deposited under ATCC under No. PTA-5129. Optionally, the humanized antibody is a humanized version of mouse antibody 12A11 expressed by the hybridoma deposited under ATCC under No. PTA-7271.

BRIEF DESCRIPTION OF THE DRAWINGS

FIG. 1 shows light (SEQ ID NO: 30) and heavy chain (SEQ ID NO: 31) amino acid sequence of Bapineuzumab predicted from the expression construct DNA sequences.

FIG. 4 shows the mean, median and standard deviation MMSE change from baseline at month four.

FIG. 5 shows the results of statistical testing of the MMSE change from baseline at month four.

FIG. 10 shows the mean serum AAB-001 concentration vs. time profiles following intravenous administration of AAB-001 at doses of 0.15, 0.5, 1.0, and 2.0 mg/kg.

DETAILED DESCRIPTION OF THE INVENTION

Figure 2:
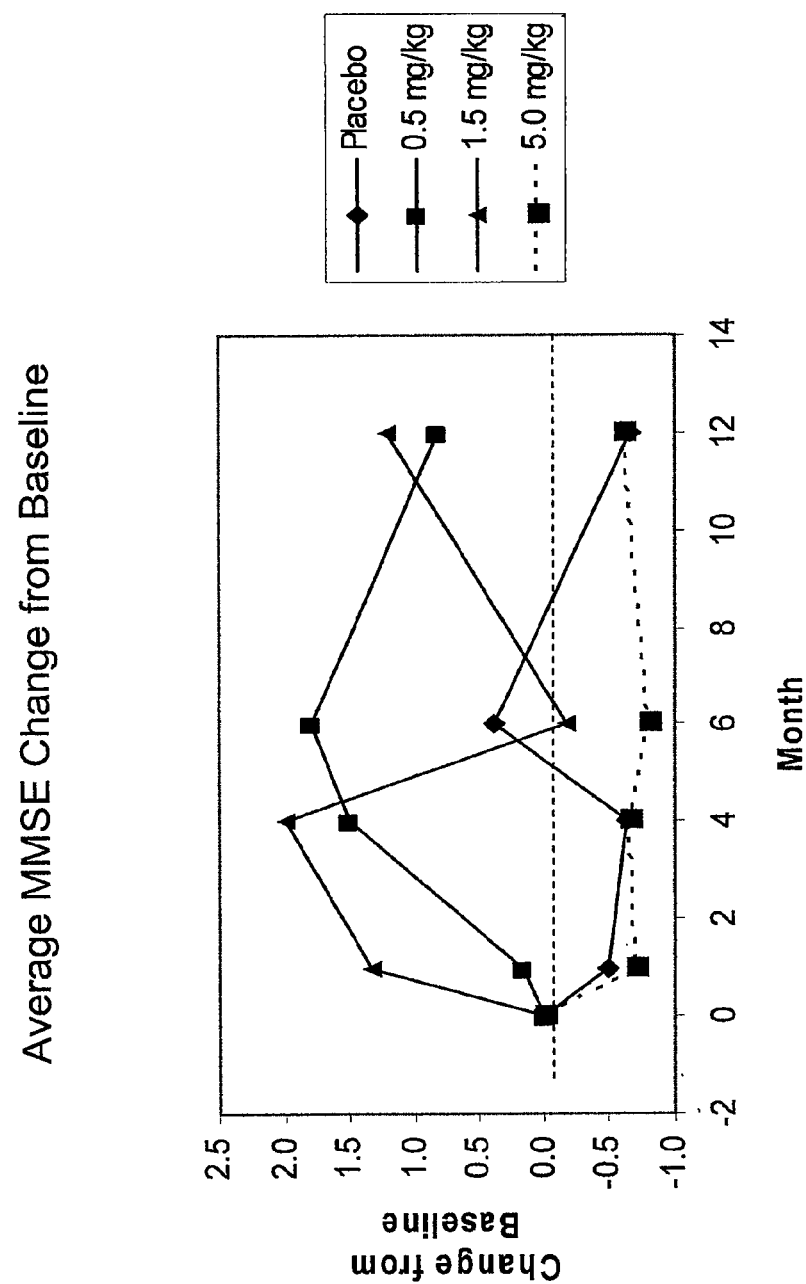
FIG. 2 shows the average MMSE change from baseline.

The application provides preferred dosages and frequencies of administration of antibodies to an N-terminal fragment of Aβ to maximize therapeutic benefit relative to occurrence of side effects, particularly vasogenic edema. A series of experiments using different regimes of the mouse 3D6 antibody in transgenic PDAPP mouse have identified a steady state average serum concentration of antibody of about 3.7 µg/ml for reducing amyloid accumulation. The present data provide evidence that doses of 0.5 mg/kg and 1.5 mg/kg administered intravenously every 13 weeks were effective in inhibiting cognitive decline in Alzheimer's patients. These regimes give rise to average serum concentrations of antibody that bracket the effective dose of 3.7 µg/ml in mice. For example, a dose of 0.5 mg/kg administered every 13 weeks was found to give an average serum concentration of about 3 µg/ml. A dose of 1 mg/kg administered every 13 weeks was found to give an average serum concentration of about 5.5 µg/ml and a dose of 2 mg/kg administered every 13 weeks was predicted to give an average serum concentration of 9.4 µg/ml. Thus, the present data indicate that the same order of magnitude of serum concentrations of antibody that are effective in mice are effective in humans. These data are further supported by clinical trials using immunotherapy with full-length Aβ1-42. In these trials, antibody responders were found to have a statistically significant inhibition of cognitive decline. The antibody responders had an ELISA titer of antibody of at least 1 in 2200, which corresponds to a serum titer of about 1 µg/ml.

The present data also provide evidence that higher doses of antibody particularly 5 mg/kg achieve no greater (and possibly less) therapeutic benefit than lower doses in the 0.5-1.5 mg/kg range but also produce significant side effects, particularly vasogenic edema, in some patients. Although practice of the present invention is not dependent on an understanding of mechanism, it is believed that the side effects result from high maximum concentrations of antibody following its administration.

In the aggregate, these data indicate that therapeutic benefit can be obtained with relatively modest doses of antibody designed to give similar average serum concentrations to the 3.7 µg/ml found effective in mice or the values bracketing this figure which appear to be effective in humans. The present data also indicate that for regimes delivering equivalent areas under the curve in terms of serum concentration of antibody as a function of time that smaller dosages administered more frequently have a better efficacy to side effects profile than large dosages administered less frequently because the former regimes avoid the spikes in antibody concentration attendant to administering larger doses in the latter regimes. In the study in the present examples, doses were administered intravenously every 13 weeks. Although the interval for doses can be reduced to about monthly with commensurate reductions in individual doses, further increase in the frequency to weekly or biweekly (biweekly) has a high risk of noncompliance due to the inconvenience of intravenous administration, which usually requires a visit to an infusion center. However, weekly or biweekly dosing is practical by subcutaneous administration, which can easily be self-administered or administered by a caregiver without medical training. Subcutaneous delivery also results in more gradual delivery to the blood avoiding spikes in concentration. The bioavailability measured by area under the curve of antibody in plasma of subcutaneous delivery relative to intravenous delivery is about 70-100%.

Thus, preferred regimes for administering antibodies specifically binding to an N-terminal fragment of Aβ achieves an average serum concentration of administered antibody of 1-15 µg/ml in a patient. This range brackets the demonstrated effective concentrations in mice and humans allowing some margin for error in measurement and individual patient variation. The serum concentration can be determined by actual measurement or predicted from standard pharmacokinetics (e.g., WinNonline Version 4.0.1 (Pharsight Corporation, Cary, USA)) based on the amount of antibody administered, frequency of administration, route of administration and antibody half-life. The average antibody concentration in the serum is preferably within a range of 1-10, 1-5 or 2-4 µg/ml.

Figure 9:
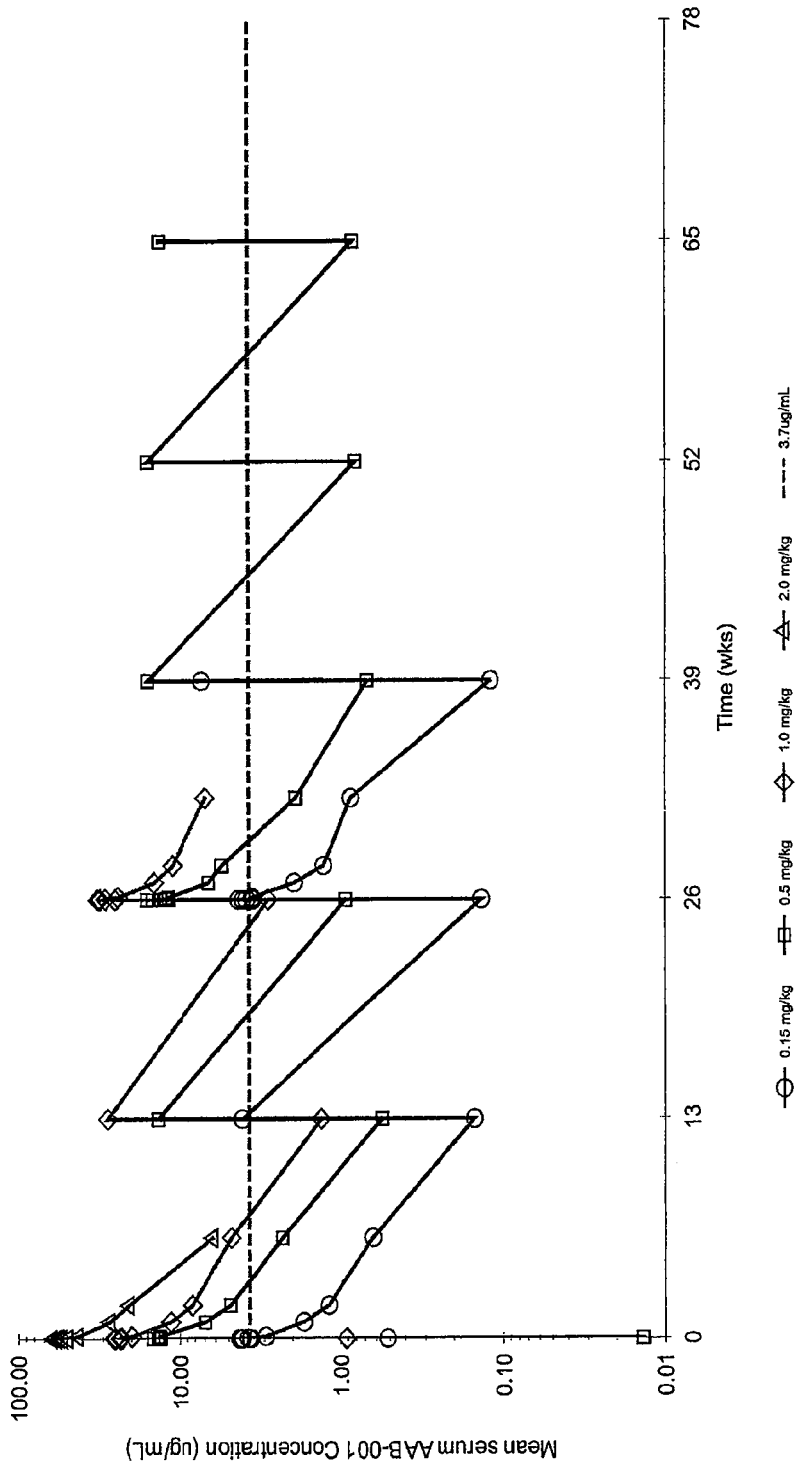
FIG. 9 shows pharmacokinetic parameters following intravenous administration of AAB-001 at doses of 0.15, 0.5, 1.0, and 2.0 mg/kg.

The present data also provide evidence that administering an antibody that specifically binds to an N-terminal fragment of Aβ in a regime sufficient to maintain a maximum serum concentration of the antibody in the patient less than about 28 µg antibody/ml serum maximizes therapeutic benefit relative to the occurrence of possible side effects, particularly vascular edema. A preferred maximum serum concentration is within a range of about 4-28 µg antibody/ml serum. The combination of maximum serum less than about 28 µg antibody/ml serum and an average serum concentration of the antibody in the patient is below about 7 µg antibody/ml serum is particularly beneficial. See FIGS. 9 and 10.

The present data also provide evidence that administering an antibody that specifically binds to an N-terminal fragment of Aβ in a regime sufficient to maintain an average serum concentration of the antibody below about 7 µg antibody/ml serum maximizes therapeutic benefit relative to the occurrence of possible side effects, particularly vascular edema. A preferred average concentration is within a range of about 2-7 µg antibody/ml serum.

If the antibody is administered intravenously it is as discussed above inconvenient to have to administer it more frequently than about monthly. Preferred doses of antibody for monthly intravenous administration occur in the range of 0.1-1.0 mg/kg antibody or preferably 0.5-1.0 mg/kg antibody.

For more frequent dosing, e.g., from weekly to monthly dosing, subcutaneous administration is preferred. The doses used for subcutaneous dosing are usually in the range of 0.1 to 0.6 mg/kg or 0.01-0.35 mg/kg, preferably, 0.05-0.25 mg/kg. For weekly or biweekly dosing, the dose is preferably in the range of 0.015-0.2 mg/kg, or 0.05-0.15 mg/kg. For weekly dosing, the dose is preferably 0.05 to 0.07 mg/kg, e.g., about 0.06 mg/kg. For biweekly dosing, the dose is preferably 0.1 to 0.15 mg/kg. For monthly dosing, the dose is preferably 0.1 to 0.3 mg/kg or about 2 mg/kg. Monthly dosing includes dosing by the calendar month or lunar month (i.e., every four weeks).

Figure 6:
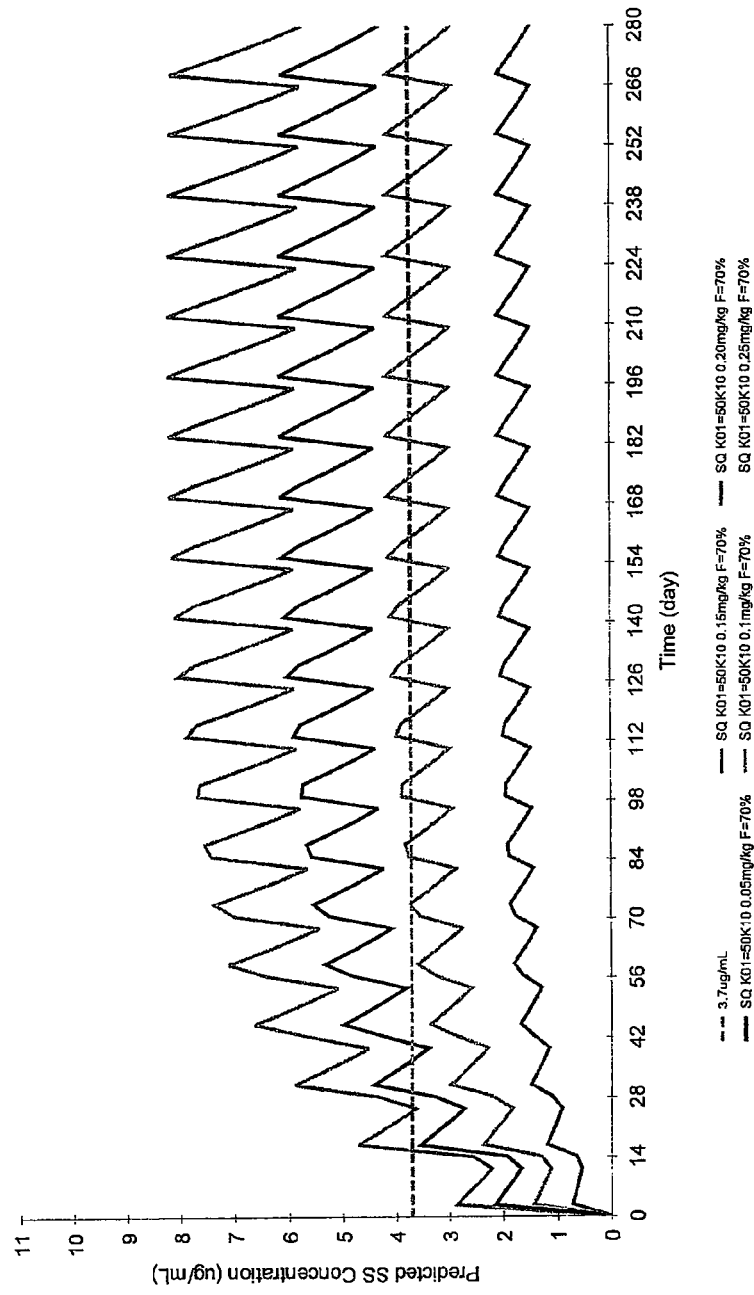
FIG. 6 shows simulated steady state serum concentrations of antibody from various subcutaneous regimes assuming bioavailability of 70%.
Figure 7:
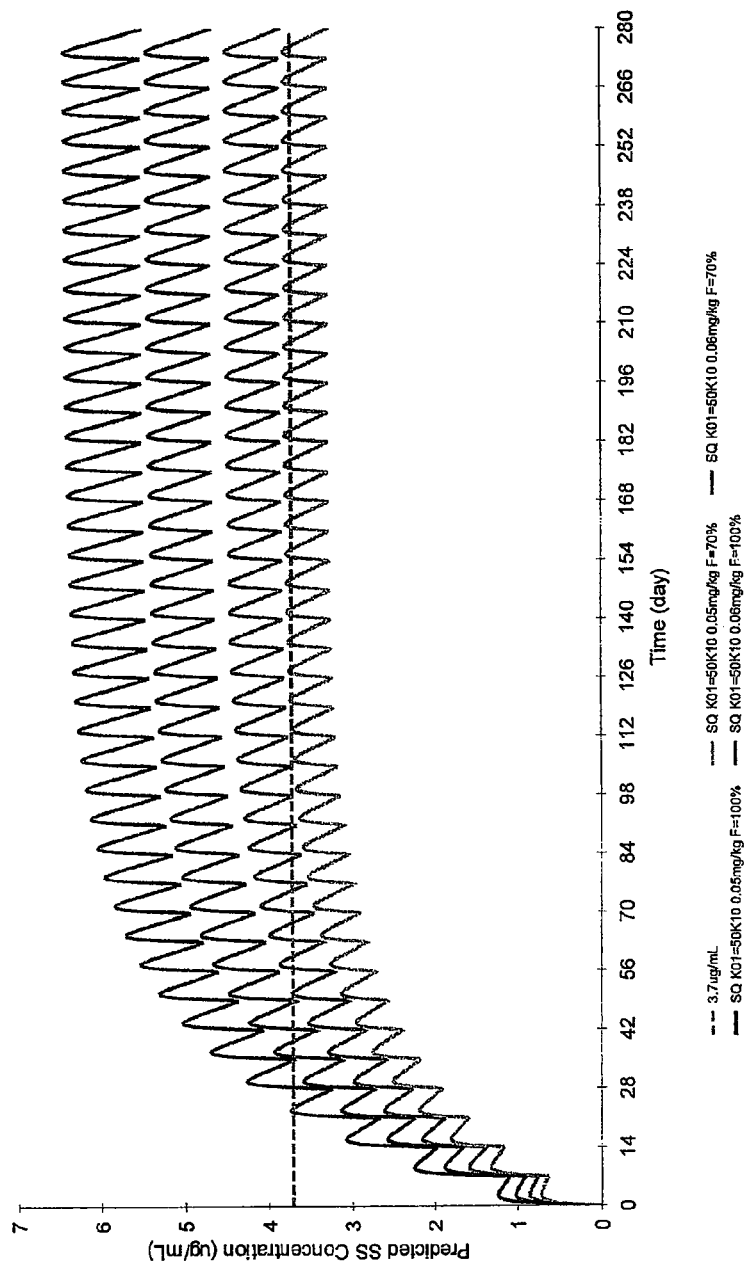
FIG. 7 shows steady state concentrations of antibody following subcutaneous administration of AAB-001 at doses of 0.05 or 0.06 mg/kg assuming 70% or 100% bioavailability.
Figure 8:
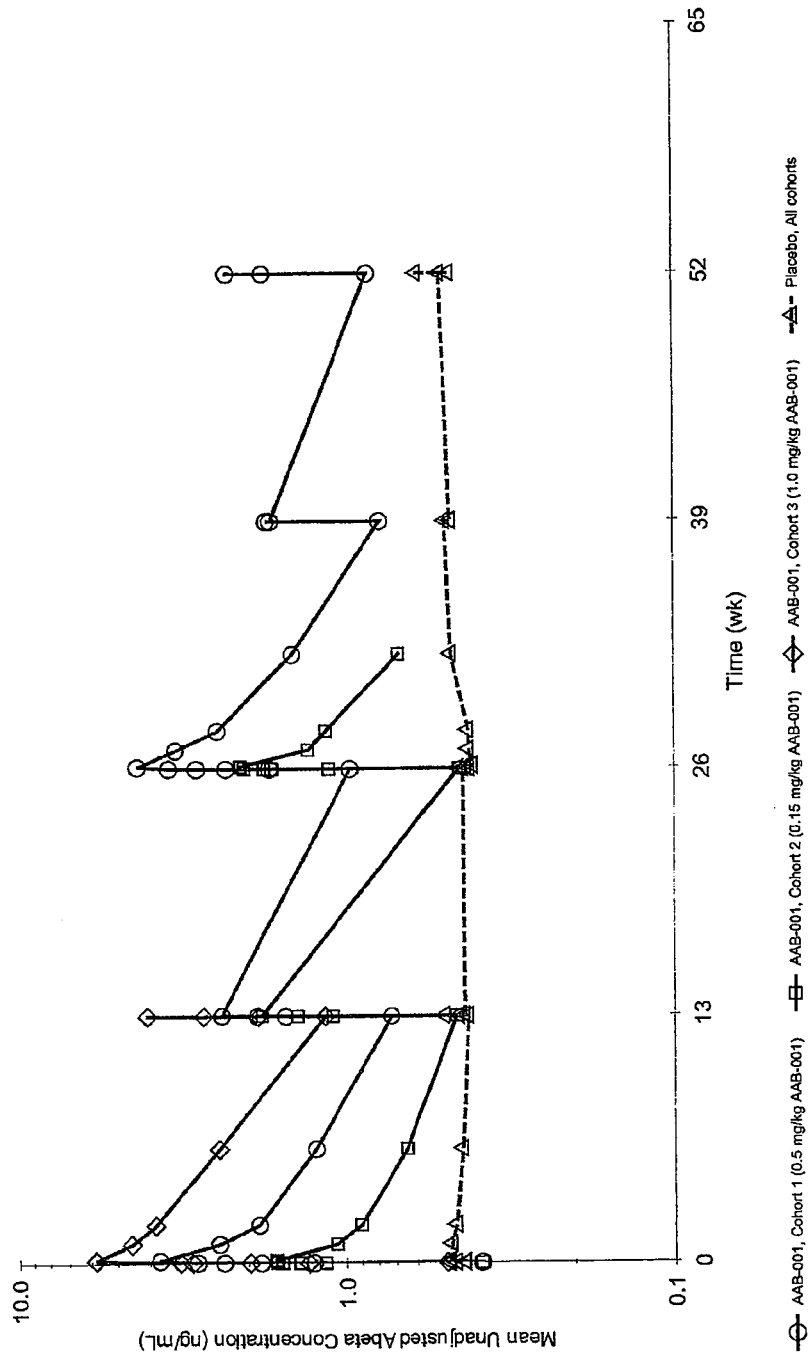
FIG. 8 shows plasma Aβ levels following administration of AAB-001 at doses of 0.15, 0.5, or 1.0 mg/kg.

FIG. 6 shows simulated steady state serum concentrations of antibody from various subcutaneous regimes assuming bioavailability of 70%. It can be seen that a dose of 0.1 mg/kg gives an average serum concentration very close to the 3.7 µg/ml found effective in mice with little peak to trough variation. FIG. 7 shows steady state concentrations of antibody following subcutaneous administration at doses of 0.05 and 0.06 mg/kg assuming 70% or 100% bioavailability. It can be seen that at 70% bioavailability, the 0.05 and 0.06 mg/kg doses lie just below and above the 3.7 µg/ml dose found effective in mice with little peak to trough variation.

The treatment regime is usually continued so that the average serum concentrations of antibody described above are maintained for at least six months or a year, and sometimes for life. The serum concentration can be measured at any time during treatment and the dose and/or frequency of administration increased if the average concentration falls beneath a target range or the dose and/or frequency decreased if the average concentration falls above a target range.

Although determining optimal plasma concentrations of antibody is useful in determining a dosage regime or optimizing dosage in an individual patient, in practice once an effective dosage regime in terms of mg/kg or mg and frequency of administration has been determined, the same dosage regime can be used on many other patients without the need for detailed calculation or measurement of patient titers. Thus, any of the above mentioned dosages and treatment regimes can be used irrespective whether a titer is measured or predicted in a particular patient. For example, one suitable regime is intravenous administration at monthly intervals with a dose in range of 0.1-1.0 mg/kg antibody or preferably 0.5-1.0 mg/kg antibody. For subcutaneous dosing the dose used is usually in the range of 0.01-0.6 mg/kg or 0.01-0.35 mg/kg, preferably, 0.05-0.25 mg/kg. For weekly or biweekly dosing, the dose is preferably in the range of 0.015-0.2 mg/kg, or 0.05-0.15 mg/kg. For weekly dosing, the dose is preferably 0.05 to 0.07 mg/kg, e.g., 0.06 mg/kg. For biweekly dosing, the dose is preferably 0.1 to 0.15 mg/kg. For monthly dosing, the dose is preferably 0.1 to 0.3 mg/kg or 2 mg/kg.

Here as elsewhere in the application, dosages expressed in mg/kg can be converted to absolute mass dosages by multiplying by the mass of a typical patient (e.g., 70 or 75 kg) typically rounding to a whole number. Expressed in terms of absolute mass, antibodies are usually administered at a dose of 1-40 mg at a frequency of between weekly and monthly. Preferred ranges are 5-25 mg or 2.5-15 mg at a frequency of weekly to monthly. For weekly to biweekly administration, the dose is often 1-12 mg or 2.5 to 10 mg. For weekly administration, the dose is often 2.5 to 5 mg or 4-5 mg. For biweekly administration, the dose can be 7-10 mg. The mass of antibody packaged for administration in unit doses is usually round to whole number, such as 1, 5, 10, 20, 30, 40, 50, 75 or 100 mg.

The invention provides preferred dosage ranges and monitoring regimes for use in treatment of Alzheimer's disease using antibodies to Aβ. The methods are premised in part on results of a clinical trial described in the Examples. A preferred dosage range for antibodies that bind to an N-terminal fragment of Aβ is from about 0.5 to 5 mg antibody per kg patient body weight. Preferred dosages are less than 5 mg/kg. Dosages from 0.5 to 3 mg/kg, 0.5 to 1.5 mg/kg and 1.5 mg/kg are particularly preferred.

The invention also provides monitoring regimes that can assess changes in symptoms or signs of the patient following treatment. The symptoms or signs can relate to Alzheimer's disease itself and/or side effects of the treatment. The dosage of drug or its frequency of administration can be adjusted based on the outcome of the monitoring. Alternatively or additionally, additional drugs can be administered to treat any side effects. For example, monitoring by MRI and/or FLAIR sequence imaging can be used to detect PRES or vascular edema or signs or symptoms thereof. Presence of PRES or vascular edema is an indication that the dosage should be reduced or suspended, or the interval between administration of dosages increased. Alternatively, or additionally, the patient can be administered a steroid to treat the PRES or vascular edema. After reducing or suspending dosage or increasing the interval between dosages, and/or administering the steroid, continued monitoring can indicate disappearance of PRES or vascular edema, in which case the original amount and/or interval of dosing can be resumed. Administration of the steroid may or may not be continued as a prophylactic measure at this point. As another example, monitoring of blood pressure can indicate development of hypertension. In analogous fashion, the dosage can be reduced in amount or suspended, and/or intervals between dosage increased and/or an antihypertensive administered. If and when further monitoring indicates the hypertension has disappeared, the original amount and/or interval of dosing can be resumed. Administration of antihypertensive may or may not be continued as a prophylactic measure at this point.

Prior to describing the invention, it may be helpful to an understanding thereof to set forth definitions of certain terms to be used hereinafter.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. "Constant" domains on the light chain are referred to interchangeably as "light chain constant regions", "light chain constant domains", "CL" regions or "CL" domains). "Constant" domains on the heavy chain are referred to interchangeably as "heavy chain constant regions", "heavy chain constant domains", "CH" regions or "CH" domains). "Variable" domains on the light chain are referred to interchangeably as "light chain variable regions", "light chain variable domains", "VL" regions or "VL" domains). "Variable" domains on the heavy chain are referred to interchangeably as "heavy chain constant regions", "heavy chain constant domains", "CH" regions or "CH" domains).

The term "region" refers to a part or portion of an antibody chain and includes constant or variable domains as defined herein, as well as more discrete parts or portions of said domains. For example, light chain variable domains or regions include "complementarity determining regions" or "CDRs" interspersed among "framework regions" or "FRs", as defined herein.

Immunoglobulins or antibodies can exist in monomeric or polymeric form. The term "antigen-binding fragment" refers to a polypeptide fragment of an immunoglobulin or antibody binds antigen or competes with intact antibody (i.e., with the intact antibody from which they were derived) for antigen binding (i.e., specific binding). The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

"Specific binding" of an antibody mean that the antibody exhibits appreciable affinity for antigen or a preferred epitope and, preferably, does not exhibit significant cross reactivity. "Appreciable" or preferred binding include binding with an affinity of at least $10^6$, $10^7$, $10^8$, $10^9$ $M^{-1}$, or $10^{10}$ $M^{-1}$. Affinities greater than $10^7$ $M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{10}$ $M^{-1}$, preferably $10^7$ to $10^{10}$ $M^{-1}$, more preferably $10^8$ to $10^{10}$ $M^{-1}$. An antibody that "does not exhibit significant cross reactivity" is one that will not appreciably bind to an undesirable entity (e.g., an undesirable proteinaceous entity). For example, an antibody that specifically binds to Aβ will appreciably bind Aβ but will not significantly react with non-Aβ proteins or peptides (e.g., non-Aβ proteins or peptides included in plaques). An antibody specific for a preferred epitope will, for example, not significantly cross react with remote epitopes on the same protein or peptide. Specific binding can be determined according to any art-recognized means for determining such binding. Preferably, specific binding is determined according to Scatchard analysis and/or competitive binding assays.

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino acid sequence for comparison purposes, the region shares at least 80-90%, preferably 90-95%, more preferably 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably 90-95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

An "antigen" is an entity (e.g., a protenaceous entity or peptide) to which an antibody specifically binds.

The term "epitope" or "antigenic determinant" refers to a site on an antigen to which an immunoglobulin or antibody (or antigen binding fragment thereof) specifically binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, G. E. Morris, Ed. (1996).

Antibodies that recognize the same epitope can be identified in a simple immunoassay showing the ability of one antibody to block the binding of another antibody to a target antigen, i.e., a competitive binding assay. Competitive binding is determined in an assay in which the immunoglobulin under test inhibits specific binding of a reference antibody to a common antigen, such as Aβ. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

An epitope is also recognized by immunologic cells, for example, B cells and/or T cells. Cellular recognition of an epitope can be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

Exemplary epitopes or antigenic determinants can be found within the human amyloid precursor protein (APP), but are preferably found within the Aβ peptide of APP. Multiple isoforms of APP exist, for example APP$^{695}$, APP$^{751}$ and APP$^{770}$. Amino acids within APP are assigned numbers according to the sequence of the APP$^{770}$ isoform (see e.g., GenBank Accession No. P05067, also set forth as SEQ ID NO:38). Aβ (also referred to herein as beta amyloid peptide and A-beta) peptide is a ~4-kDa internal fragment of 39-43 amino acids of APP (Aβ39, Aβ40, Aβ41, Aβ42 and Aβ43). Aβ40, for example, consists of residues 672-711 of APP and Aβ42 consists of residues 673-713 of APP. As a result of proteolytic processing of APP by different secretase enzymes iv vivo or in situ, Aβ is found in both a "short form", 40 amino acids in length, and a "long form", ranging from 42-43 amino acids in length. Preferred epitopes or antigenic determinants, as described herein, are located within the N-terminus of the Aβ peptide and include residues within amino acids 1-10 of Aβ, preferably from residues 1-3, 1-4, 1-5, 1-6, 1-7 or 3-7 of Aβ42. Additional referred epitopes or antigenic determinants include residues 2-4, 5, 6, 7 or 8 of Aβ, residues 3-5, 6, 7, 8 or 9 of Aβ, or residues 4-7, 8, 9 or 10 of Aβ42.

The term "amyloidogenic disease" includes any disease associated with (or caused by) the formation or deposition of insoluble amyloid fibrils. Exemplary amyloidogenic diseases include, but are not limited to systemic amyloidosis, Alzheimer's disease, mature onset diabetes, Parkinson's disease, Huntington's disease, fronto-temporal dementia, and the prion-related transmissible spongiform encephalopathies (kuru and Creutzfeldt-Jacob disease in humans and scrapie and BSE in sheep and cattle, respectively). Different amyloidogenic diseases are defined or characterized by the nature of the polypeptide component of the fibrils deposited. For example, in subjects or patients having Alzheimer's disease, β-amyloid protein (e.g., wild-type, variant, or truncated β-amyloid protein) is the characterizing polypeptide component of the amyloid deposit. Accordingly, Alzheimer's disease is an example of a "disease characterized by deposits of Aβ" or a "disease associated with deposits of Aβ", e.g., in the brain of a subject or patient. The terms "β-amyloid protein", "β-amyloid peptide", "β-amyloid", "Aβ" and "Aβ peptide" are used interchangeably herein.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the patient's own immune system.

The term "patient" includes human and other mammalian subjects that receive either prophylactic or therapeutic treatment.

"Soluble" or "dissociated" Aβ refers to non-aggregating or disaggregated Aβ polypeptide. "Insoluble" Aβ refers to aggregating Aβ polypeptide, for example, Aβ held together by noncovalent bonds. Aβ (e.g., Aβ42) is believed to aggregate, at least in part, due to the presence of hydrophobic residues at the C-terminus of the peptide (part of the transmembrane domain of APP). One method to prepare soluble Aβ is to dissolve lyophilized peptide in neat DMSO with sonication. The resulting solution is centrifuged to remove any insoluble particulates.

The term "effector function" refers to an activity that resides in the Fc region of an antibody (e.g., an IgG antibody) and includes, for example, the ability of the antibody to bind effector molecules such as complement and/or Fc receptors, which can control several immune functions of the antibody such as effector cell activity, lysis, complement-mediated activity, antibody clearance, and antibody half-life.

The term "effector molecule" refers to a molecule that is capable of binding to the Fc region of an antibody (e.g., an IgG antibody) including, but not limited to, a complement protein or a Fc receptor.

The term "effector cell" refers to a cell capable of binding to the Fc portion of an antibody (e.g., an IgG antibody) typically via an Fc receptor expressed on the surface of the effector cell including, but not limited to, lymphocytes, e.g., antigen presenting cells and T cells.

The term "Fc region" refers to a C-terminal region of an IgG antibody, in particular, the C-terminal region of the heavy chain(s) of said IgG antibody. Although the boundaries of the Fc region of an IgG heavy chain can vary slightly, a Fc region is typically defined as spanning from about amino acid residue Cys226 to the carboxyl-terminus of an IgG heavy chain(s).

The term "Kabat numbering" unless otherwise stated, is defined as the numbering of the residues in, e.g., an IgG heavy chain antibody using the EU index as in Kabat et al. (Sequences of Proteins of Immunological Interest, 5th Ed. Public Health Service, National Institutes of Health, Bethesda, Md. (1991)), expressly incorporated herein by reference.

The term "Fc receptor" or "FcR" refers to a receptor that binds to the Fc region of an antibody. Typical Fc receptors which bind to an Fc region of an antibody (e.g., an IgG antibody) include, but are not limited to, receptors of the FcγRI, FcγRII, and FcγRIII subclasses, including allelic variants and alternatively spliced forms of these receptors. Fc receptors are reviewed in Ravetch and Kinet, Annu. Rev.

Immunol 9:457-92 (1991); Capel et al., Immunomethods 4:25-34 (1994); and de Haas et al., J. Lab. Clin. Med. 126: 330-41 (1995).

Immunological and Therapeutic Reagents

Immunological and therapeutic reagents of the invention comprise or consist of immunogens or antibodies, or functional or antigen binding fragments thereof, as defined herein. The basic antibody structural unit is known to comprise a tetramer of subunits. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Antibodies

The term "antibody" as used herein refers to immunoglobulin molecules and immunologically active portions of immunoglobulin molecules, i.e., molecules that contain an antigen binding site which specifically binds (recognizes) an antigen. Examples of immunologically active portions of immunoglobulin molecules include F(ab) and F(ab')2 fragments which can be generated by treating the antibody with an enzyme such as pepsin or produced by art-recognized recombinant engineering techniques. Aspects of the invention also relevant for the stabilization of antibodies include, for example, polyclonal and monoclonal antibodies that bind an antigen, for example a therapeutic target antigen, such as, Aβ. The term "monoclonal antibody" or "monoclonal antibody composition", as used herein, refers to a population of antibody molecules that contain only one species of an antigen binding site capable of recognizing and binding to a particular epitope of a target antigen, for example, an epitope(s) of Aβ. A monoclonal antibody composition thus typically displays a single binding specificity and affinity for a particular target antigen with which it immunoreacts.

Polyclonal Antibodies

Polyclonal antibodies can be prepared as described above by immunizing a suitable subject with an immunogen. The antibody titer in the immunized subject can be monitored over time by standard techniques, such as with an enzyme linked immunosorbent assay (ELISA) using immobilized target antigen. If desired, the antibody molecules directed against the target antigen can be isolated from the mammal (e.g., from the blood) and further purified by well known techniques, such as protein A Sepharose chromatography to obtain the antibody, e.g., IgG, fraction. At an appropriate time after immunization, e.g., when the anti-antigen antibody titers are highest, antibody-producing cells can be obtained from the subject and used to prepare monoclonal antibodies by standard techniques, such as the hybridoma technique originally described by Kohler and Milstein (1975) Nature 256:495-497) (see also, Brown et al. (1981) J. Immunol. 127:539-46; Brown et al. (1980) J. Biol. Chem. 255:4980-83; Yeh et al. (1976) Proc. Natl. Acad. Sci. USA 76:2927-31; and Yeh et al. (1982) Int. J. Cancer 29:269-75). For the preparation of chimeric polyclonal antibodies, see Buechler et al. U.S. Pat. No. 6,420,113.

Monoclonal Antibodies

Any of the many well known protocols used for fusing lymphocytes and immortalized cell lines can be applied for the purpose of generating a monoclonal antibody (see, e.g., G. Galfre et al. (1977) Nature 266:55052; Gefter et al. (1977) Somatic Cell Genet., cited supra; Lerner, Yale J. Biol. Med., cited supra; Kenneth, Monoclonal Antibodies, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a target antigen, e.g., Aβ, using a standard ELISA assay.

Recombinant Antibodies

Alternative to preparing monoclonal antibody-secreting hybridomas, a monoclonal antibody can be identified and isolated by screening a recombinant combinatorial immunoglobulin library (e.g., an antibody phage display library) with a target antigen to thereby isolate immunoglobulin library members that bind the target antigen. Kits for generating and screening phage display libraries are commercially available (e.g., the Pharmacia *Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246: 1275-1281; Griffiths et al. (1993) *EMBO J* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. *Nature* (1990) 348:552-554.

Chimeric and Humanized Antibodies

Additionally, recombinant antibodies, such as chimeric and humanized monoclonal antibodies, comprising both human and non-human portions, which can be made using standard recombinant DNA techniques, are within the scope of the invention.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino sequence for comparison purposes, the region shares at least 80-90%, 90-95%, or 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably at least 90-95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The term "significant identity" means that two polypeptide sequences, when optimally aligned, such as by the programs GAP or BESTFIT using default gap weights, share at least 50-60% sequence identity, preferably at least 60-70% sequence identity, more preferably at least 70-80% sequence identity, more preferably at least 80-90% sequence identity, even more preferably at least 90-95% sequence identity, and even more preferably at least 95% sequence identity or more (e.g., 99% sequence identity or more). The term "substantial identity" means that two polypeptide sequences, when optimally aligned, such as by the programs GAP or BESTFIT using default gap weights, share at least 80-90% sequence identity, preferably at least 90-95% sequence identity, and more preferably at least 95% sequence identity or more (e.g., 99% sequence identity or more). For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology). One example of algorithm that is suitable for determining percent sequence identity and sequence similarity is the BLAST algorithm, which is described in Altschul et al., J. Mol. Biol. 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1989)).

Preferably, residue positions which are not identical differ by conservative amino acid substitutions. For purposes of classifying amino acids substitutions as conservative or non-conservative, amino acids are grouped as follows: Group I (hydrophobic sidechains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Preferably, humanized immunoglobulins or antibodies bind antigen with an affinity that is within a factor of three, four, or five of that of the corresponding non-humanized antibody. For example, if the nonhumanized antibody has a binding affinity of $10^{-9}$ M, humanized antibodies will have a binding affinity of at least $3 \times 10^{-8}$ M, $4 \times 10^{-8}$ M, $5 \times 10^{-8}$ M, or $10^{-9}$ M. When describing the binding properties of an immunoglobulin or antibody chain, the chain can be described based on its ability to "direct antigen (e.g., Aβ) binding". A chain is said to "direct antigen binding" when it confers upon an intact immunoglobulin or antibody (or antigen binding fragment thereof) a specific binding property or binding affinity. A mutation (e.g., a backmutation) is said to substantially affect the ability of a heavy or light chain to direct antigen binding if it affects (e.g., decreases) the binding affinity of an intact immunoglobulin or antibody (or antigen binding fragment thereof) comprising said chain by at least an order of magnitude compared to that of the antibody (or antigen binding fragment thereof) comprising an equivalent chain lacking said mutation. A mutation "does not substantially affect (e.g., decrease) the ability of a chain to direct antigen binding" if it affects (e.g., decreases) the binding affinity of an intact immunoglobulin or antibody (or antigen binding fragment thereof) comprising said chain by only a factor of two, three, or four of that of the antibody (or antigen binding fragment thereof) comprising an equivalent chain lacking said mutation.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species. The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Canc. Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Oi et al. (1986) BioTechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060.

Human Antibodies from Transgenic Animals and Phage Display

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice results in the production of human antibodies upon antigen challenge. See, e.g., U.S. Pat. Nos. 6,150,584; 6,114,598; and 5,770,429.

Fully human antibodies can also be derived from phage-display libraries (Hoogenboom et al., J. Mol. Biol., 227:381 (1991); Marks et al., J. Mol. Biol., 222:581-597 (1991)). Chimeric polyclonal antibodies can also be obtained from phage display libraries (Buechler et al. U.S. Pat. No. 6,420,113).

Bispecific Antibodies, Antibody Fusion Polypeptides, and Single-Chain Antibodies Bispecific antibodies (BsAbs) are antibodies that have binding specificities for at least two different epitopes. Such antibodies can be derived from full length antibodies or antibody fragments (e.g. F(ab)'2 bispecific antibodies). Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of different antibody molecules (see, WO 93/08829 and in Traunecker et al., EMBO J., 10:3655-3659 (1991)).

Bispecific antibodies also include cross-linked or "heteroconjugate" antibodies. For example, one of the antibodies in the heteroconjugate can be coupled to avidin, the other to biotin or other payload. Heteroconjugate antibodies may be made using any convenient cross-linking methods. Suitable cross-linking agents are well known in the art, and are disclosed in U.S. Pat. No. 4,676,980, along with a number of cross-linking techniques.

In yet another aspect, the antibody can be fused, chemically or genetically, to a payload such as a reactive, detectable, or functional moiety, for example, an immunotoxin to produce an antibody fusion polypeptide. Such payloads include, for example, immunotoxins, chemotherapeutics, and radioisotopes, all of which are well-known in the art.

Single chain antibodies are also suitable for stabilization according to the invention. The fragments comprise a heavy-chain variable domain (VH) connected to a light-chain variable domain (VL) with a linker, which allows each variable region to interface with each other and recreate the antigen binding pocket of the parent antibody from which the VL and VH regions are derived. See Gruber et al., J. Immunol., 152: 5368 (1994).

Nanobodies

Nanobodies are antibody-derived therapeutic proteins that contain the properties of naturally-occurring heavy chain antibodies. Nanobodies can function as a single, relatively small, functional antigen-binding structural unit, domain or protein. The Nanobody™ technology (Ablynx Nev.) was originally developed following the discovery that camelidae (camels and llamas) possess fully functional antibodies that lack light chains. These heavy-chain antibodies contain a single variable domain (VHH) and two constant domains (CH2 and CH3). VHH is used to distinguish them from the heavy chain variable domains that are present in conventional 4-chain antibodies (which are referred to as "VH domains"). The cloned and isolated VHH domain is a stable polypeptide harboring the full antigen-binding capacity of the original heavy-chain antibody. VHH domains and nanobodies can also be engineered into multivalent and multispecific formats. Nanobodies with an amino acid sequence that corresponds to the amino acid sequence of a naturally occurring VHH domain can be humanized, i.e. by replacing one or more amino acid residues in the amino acid sequence of the naturally occurring VHH sequence (and in particular in the framework sequences) by one or more of the amino acid residues that occur at the corresponding position(s) in a VH domain from a conventional 4-chain antibody from a human being. For details, see e.g., US 20050130266, US 20040253638, WO/2006/040153, US 20050214857, WO/2006/079372, or WO/2006/122825, each of which is incorporated herein by reference for all purposes. Antibodies against Aβ can also be produced via the Nanobody™ methods.

It is understood that any of the foregoing polypeptide molecules, alone or in combination, are suitable for preparation as stabilized formulations according to the invention.

Anti Aβ Antibodies

Generally, the formulations of the present invention include a variety of antibodies for treating amyloidogenic diseases, in particular, Alzheimer's Disease, by targeting Aβ peptide.

The terms "Aβ antibody", "anti Aβ antibody" and "anti Aβ" are used interchangeably herein to refer to an antibody that binds to one or more epitopes or antigenic determinants of the human amyloid precursor protein (APP), Aβ protein, or both. Exemplary epitopes or antigenic determinants can be found within APP, but are preferably found within the Aβ peptide of APP. Multiple isoforms of APP exist, for example APP$^{695}$, APP$^{751}$ and APP$^{770}$. Amino acids within APP are assigned numbers according to the sequence of the APP$^{770}$ isoform (see e.g., GenBank Accession No. P05067). Examples of specific isotypes of APP which are currently known to exist in humans are the 695 amino acid polypeptide described by Kang et. al. (1987) *Nature* 325:733-736 which is designated as the "normal" APP; the 751 amino acid polypeptide described by Ponte et al. (1988) *Nature* 331:525-527 (1988) and Tanzi et al. (1988) *Nature* 331:528-530; and the 770-amino acid polypeptide described by Kitaguchi et. al. (1988) *Nature* 331:530-532. As a result of proteolytic processing of APP by different secretase enzymes in vivo or in situ, Aβ is found in both a "short form", 40 amino acids in length, and a "long form", ranging from 42-43 amino acids in length. The short form, Aβ$_{40}$, consists of residues 672-711 of APP. The long form, e.g., Aβ$_{42}$ or Aβ$_{43}$, consists of residues 672-713 or 672-714, respectively. Part of the hydrophobic domain of APP is found at the carboxy end of Aβ, and may account for the ability of Aβ to aggregate, particularly in the case of the long form. Aβ peptide can be found in, or purified from, the body fluids of humans and other mammals, e.g. cerebrospinal fluid, including both normal individuals and individuals suffering from amyloidogenic disorders.

The terms "β-amyloid protein", "β-amyloid peptide", "β-amyloid", "Aβ" and "A β peptide" are used interchangeably herein. Aβ peptide (e.g., Aβ39, Aβ40, Aβ41, Aβ42 and Aβ43) is a ~4-kDa internal fragment of 39-43 amino acids of APP. Aβ40, for example, consists of residues 672-711 of APP and Aβ42 consists of residues 672-713 of APP. Aβ peptides include peptides resulting from secretase cleavage of APP and synthetic peptides having the same or essentially the same sequence as the cleavage products. Aβ peptides can be derived from a variety of sources, for example, tissues, cell lines, or body fluids (e.g. sera or cerebrospinal fluid). For example, an Aβ can be derived from APP-expressing cells such as Chinese hamster ovary (CHO) cells stably transfected with APP$_{717V \to F}$, as described, for example, in Walsh et al., (2002), *Nature*, 416, pp 535-539. An Aβ preparation can be derived from tissue sources using methods previously described (see, e.g., Johnson-Wood et al., (1997), *Proc. Natl. Acad. Sci. USA* 94:1550). Alternatively, Aβ peptides can be synthesized using methods which are well known to those in the art. See, for example, Fields et al., Synthetic Peptides: A User's Guide, ed. Grant, W.H. Freeman & Co., New York, N.Y., 1992, p 77). Hence, peptides can be synthesized using the automated Merrifield techniques of solid phase synthesis with the α-amino group protected by either t-Boc or F-moc chemistry using side chain protected amino acids on, for example, an Applied Biosystems Peptide Synthesizer Model 430A or 431. Longer peptide antigens can be synthesized using well known recombinant DNA techniques. For example, a polynucleotide encoding the peptide or fusion peptide can be synthesized or molecularly cloned and inserted in a suitable expression vector for the transfection and heterologous expression by a suitable host cell. Aβ peptide also refers to related Aβ sequences that results from mutations in the Aβ region of the normal gene.

The terms "Aβ-derived diffusible ligand" and "ADDL" are small, soluble Aβ42 oligomers, predominantly trimers and tetramers but also higher-order species (See e.g., Lambert, M. P. et al. (1998) Proc. Natl. Acad. Sci. USA, vol. 95, pp. 6448-6453; Chromy, B. A. et al. (2000) Soc. Neurosci. Abstr., vol. 26, p. 1284, WO 2004/031400, each of which is incorporated by reference in its entirety for all purposes.)

The term "anti-ADDL antibody" refers to an antibody that has been generated and selected for the ability to bind ADDLs specifically, without binding to Aβ monomer or amyloid fibrils. See e.g., WO 2004/031400, incorporated by reference in its entirety for all purposes.

The term "epitope" or "antigenic determinant" refers to a site on an antigen to which an immunoglobulin or antibody (or antigen binding fragment thereof) specifically binds. Exemplary epitopes or antigenic determinants to which an Aβ antibody binds can be found within the human amyloid precursor protein (APP), but are preferably found within the Aβ peptide of APP. Exemplary epitopes or antigenic determinants within Aβ are located within the N-terminus, central region, or C-terminus of Aβ. An "N-terminal epitope", is an epitope or antigenic determinant located within the N-terminus of the Aβ peptide. Exemplary N-terminal epitopes include residues within amino acids 1-10 or 1-12 of Aβ, preferably from residues 1-3, 1-4, 1-5, 1-6, 1-7, 2-6, 2-7, 3-6, or 3-7 of Aβ42. Other exemplary N-terminal epitopes start at residues 1-3 and end at residues 7-11 of Aβ. Additional exemplary N-terminal epitopes include residues 2-4, 5, 6, 7 or 8 of Aβ, residues 3-5, 6, 7, 8 or 9 of Aβ, or residues 4-7, 8, 9 or 10 of Aβ42. "Central epitopes" are epitopes or antigenic determinants comprising residues located within the central or mid-portion of the Aβ peptide. Exemplary central epitopes include residues within amino acids 13-28 of Aβ, preferably from residues 14-27, 15-26, 16-25, 17-24, 18-23, or 19-22 of Aβ. Other exemplary central epitopes include residues within amino acids 16-24, 16-23, 16-22, 16-21, 18-21, 19-21, 19-22, 19-23, or 19-24 of Aβ. "C-terminal" epitopes or antigenic determinants are located within the C-terminus of the Aβ peptide and include residues within amino acids 33-40, 33-41, or 33-42 of Aβ. "C-terminal epitopes" are epitopes or antigenic determinants comprising residues located within the C-terminus of the Aβ peptide (e.g., within about amino acids 30-40 or 30-42 of Aβ. Additional exemplary C-terminal epitopes or antigenic determinants include residues 33-40 or 33-42 of Aβ.

When an antibody is said to bind to an epitope within specified residues, such as Aβ 3-7, what is meant is that the antibody specifically binds to a polypeptide containing the specified residues (i.e., Aβ 3-7 in this an example). Such an antibody does not necessarily contact every residue within Aβ 3-7. Nor does every single amino acid substitution or deletion within Aβ 3-7 necessarily significantly affect binding affinity.

In various aspects, an Aβ antibody is end-specific. As used herein, the term "end-specific" refers to an antibody which specifically binds to the N-terminal or C-terminal residues of an Aβ peptide but that does not recognize the same residues when present in a longer Aβ species comprising the residues or in APP. In various aspects, an Aβ antibody is "C-terminus-specific." As used herein, the term "C terminus-specific" means that the antibody specifically recognizes a free C-terminus of an Aβ peptide. Examples of C terminus-specific Aβ antibodies include those that: recognize an Aβ peptide ending at residue 40 but do not recognize an Aβ peptide ending at residue 41, 42, and/or 43; recognize an Aβ peptide ending at residue 42 but do not recognize an Aβ peptide ending at residue 40, 41, and/or 43; etc.

In one aspect, the Aβ antibody may be a 3D6 antibody or variant thereof, or a 10D5 antibody or variant thereof, both of which are described in U.S. Patent Publication No. 20030165496A1, U.S. Patent Publication No. 20040087777A1, International Patent Publication No. WO 02/46237A3 and International Patent Publication No. WO04/080419A2. Description of 3D6 and 10D5 antibodies can also be found, for example, in International Patent Publication No. WO02/088306A2 and International Patent Publication No. WO02/088307A2. 10D5 antibodies are also described in U.S. Patent Publication No. 20050142131. Additional 3D6 antibodies are described in U.S. patent application Ser. No. 11/303,478 and International Application No. PCT/US05/45614. 3D6 is a monoclonal antibody (mAb) that specifically binds to an N-terminal epitope located in the human β-amyloid peptide, specifically, residues 1-5. By comparison, 10D5 is a mAb that specifically binds to an N-terminal epitope located in the human β-amyloid peptide, specifically, residues 3-6. A cell line producing the 3D6 monoclonal antibody (RB96 3D6.32.2.4) was deposited with the American Type Culture Collection (ATCC), Manassas, Va. 20108, USA on Apr. 8, 2003 under the terms of the Budapest Treaty and has deposit number PTA-5130. A cell line producing the 10D5 monoclonal antibody (RB44 10D5.19.21) was deposited with the ATCC on Apr. 8, 2003 under the terms of the Budapest Treaty and has deposit number PTA-5129.

Bapineuzumab means a humanized 3D6 antibody comprising a light chain having a mature variable region having the amino acid sequence designated SEQ ID NO: 1 and a heavy chain having a mature variable region having the amino acid sequence designated SEQ ID NO: 2.

```
Humanized 3D6 Light Chain Variable Region
                                           (SEQ ID NO: 1)
Asp Val Val Met Thr Gln Ser Pro Leu Ser Leu Pro
Val Thr Pro Gly Glu Pro Ala Ser Ile Ser Cys Lys
Ser Ser Gln Ser Leu Leu Asp Ser Asp Gly Lys Thr
Tyr Leu Asn Trp Leu Leu Gln Lys Pro Gly Gln Ser
Pro Gln Arg Leu Ile Tyr Leu Val Ser Lys Leu Asp
Ser Gly Val Pro Asp Arg Phe Ser Gly Ser Gly Ser
Gly Thr Asp Phe Thr Leu Lys Ile Ser Arg Val Glu
Ala Glu Asp Val Gly Val Tyr Tyr Cys Trp Gln Gly
Thr His Phe Pro Arg Thr Phe Gly Gln Gly Thr Lys
Val Glu Ile Lys Humanized 3D6 Heavy Chain Variable Region
                                           (SEQ ID NO: 2)
Glu Val Gln Leu Leu Glu Ser Gly Gly Gly Leu Val
Gln Pro Gly Gly Ser Leu Arg Leu Ser Cys Ala Ala
Ser Gly Phe Thr Phe Ser Asn Tyr Gly Met Ser Trp
Val Arg Gln Ala Pro Gly Lys Gly Leu Glu Trp Val
Ala Ser Ile Arg Ser Gly Gly Gly Arg Thr Tyr Tyr
Ser Asp Asn Val Lys Gly Arg Phe Thr Ile Ser Arg
Asp Asn Ser Lys Asn Thr Leu Tyr Leu Gln Met Asn
Ser Leu Arg Ala Glu Asp Thr Ala Val Tyr Tyr Cys
Val Arg Tyr Asp His Tyr Ser Gly Ser Ser Asp Tyr
Trp Gly Gln Gly Thr Leu Val Thr Val Ser Ser
```

Bapineuzumab is also known as AAB-001. FIG. 1 shows light and heavy chain mature variable region amino acid sequences of Bapineuzumab predicted from the expression construct DNA sequences. Amino acid sequence of the AAB-001 light and heavy chains predicted from the expression construct DNA sequences. CDR regions are underlined. Cysteines expected to form intermolecular disulfide bonds are underlined and the connectivity indicated. The N-linked glycosylation consensus site is in bold italics. The predicted heavy chain COOH-terminal lysine is shown in parenthesis.

A second version of humanized 3D6 antibody comprising a light chain having a mature variable region having the amino acid sequence designated SEQ ID NO: 3 and a heavy chain having a mature variable region having the amino acid sequence designated SEQ ID NO: 4 is shown below.

```
Humanized 3D6 Light Chain Variable Region
                                           (SEQ ID NO: 3)
Tyr Val Val Met Thr Gln Ser Pro Leu Ser Leu Pro
Val Thr Pro Gly Glu Pro Ala Ser Ile Ser Cys Lys
Ser Ser Gln Ser Leu Leu Asp Ser Asp Gly Lys Thr
Tyr Leu Asn Trp Leu Leu Gln Lys Pro Gly Gln Ser
Pro Gln Arg Leu Ile Tyr Leu Val Ser Lys Leu Asp
Ser Gly Val Pro Asp Arg Phe Ser Gly Ser Gly Ser
Gly Thr Asp Phe Thr Leu Lys Ile Ser Arg Val Glu
Ala Glu Asp Val Gly Val Tyr Tyr Cys Trp Gln Gly
Thr His Phe Pro Arg Thr Phe Gly Gln Gly Thr Lys
Val Glu Ile Lys Humanized 3D6 Heavy Chain Variable Region
                                           (SEQ ID NO: 4)
Glu Val Gln Leu Leu Glu Ser Gly Gly Gly Leu Val
Gln Pro Gly Gly Ser Leu Arg Leu Ser Cys Ala Ala
Ser Gly Phe Thr Phe Ser Asn Tyr Gly Met Ser Trp
Val Arg Gln Ala Pro Gly Lys Gly Leu Glu Trp Val
Ala Ser Ile Arg Ser Gly Gly Gly Arg Thr Tyr Tyr
Ser Asp Asn Val Lys Gly Arg Phe Thr Ile Ser Arg
Asp Asn Ala Lys Asn Ser Leu Tyr Leu Gln Met Asn
Ser Leu Arg Ala Glu Asp Thr Ala Leu Tyr Tyr Cys
Val Arg Tyr Asp His Tyr Ser Gly Ser Ser Asp Tyr
Trp Gly Gln Gly Thr Leu Val Thr Val Ser Ser
```

A third version of humanized 3D6 antibody comprising a light chain having the amino acid sequence designated SEQ ID NO: 5 and a heavy chain having the amino acid sequence designated SEQ ID NO: 6 is describe in US 2005/0090649 A1 published on Apr. 28, 2005, which is incorporated herein by reference for all purposes.

```
Humanized 3D6 Light Chain
                                           (SEQ ID NO: 5)
Asp Val Val Met Thr Gln Ser Pro Leu Ser Leu Pro
Val Thr Leu Gly Gln Pro Ala Ser Ile Ser Cys Lys
Ser Ser Gln Ser Leu Leu Asp Ser Asp Gly Lys Thr
Tyr Leu Asn Trp Leu Gln Gln Arg Pro Gly Gln Ser
Pro Arg Arg Leu Ile Tyr Leu Val Ser Lys Leu Asp
Ser Gly Val Pro Asp Arg Phe Ser Gly Ser Gly Ser
Gly Thr Asp Phe Thr Leu Lys Ile Ser Arg Val Glu
Ala Glu Asp Val Gly Val Tyr Tyr Cys Trp Gln Gly
Thr His Phe Pro Arg Thr Phe Gly Gly Gly Thr Lys
Val Glu Ile Lys Arg Thr Val Ala Ala Pro Ser Val
Phe Ile Phe Pro Pro Ser Asp Glu Gln Leu Lys Ser
Gly Thr Ala Ser Val Val Cys Leu Leu Asn Asn Phe
Tyr Pro Arg Glu Ala Lys Val Gln Trp Lys Val Asp
Asn Ala Leu Gln Ser Gly Asn Ser Gln Glu Ser Val
Thr Glu Gln Asp Ser Lys Asp Ser Thr Tyr Ser Leu
Ser Ser Thr Leu Thr Leu Ser Lys Ala Asp Tyr Glu
Lys His Lys Val Tyr Ala Cys Glu Val Thr His Gln
Gly Leu Ser Ser Pro Val Thr Lys Ser Phe Asn Arg
Gly Glu Cys Humanized 3D6 Heavy Chain
                                           (SEQ ID NO: 6)
Gln Val Gln Leu Val Gln Ser Gly Gly Gly Leu Val
Gln Pro Gly Gly Ser Leu Arg Leu Ser Cys Ala Gly
Ser Gly Phe Thr Phe Ser Asn Tyr Gly Met Ser Trp
Val Arg Gln Ala Pro Gly Lys Gly Leu Glu Trp Val
Ala Ser Ile Arg Ser Gly Gly Gly Arg Thr Tyr Tyr
Ser Asp Asn Val Lys Gly Arg Phe Thr Ile Ser Arg
Glu Asn Ala Lys Asn Ser Leu Tyr Leu Gln Met Asn
Ser Leu Arg Ala Glu Asp Thr Ala Val Tyr Tyr Cys
Val Arg Tyr Asp His Tyr Ser Gly Ser Ser Asp Tyr
Trp Gly Gln Gly Thr Leu Val Thr Val Ser Ser Ala
Ser Thr Lys Gly Pro Ser Val Phe Pro Leu Ala Pro
Ser Ser Lys Ser Thr Ser Gly Gly Thr Ala Ala Leu
Gly Cys Leu Val Lys Asp Tyr Phe Pro Glu Pro Val
Thr Val Ser Trp Asn Ser Gly Ala Leu Thr Ser Gly
Val His Thr Phe Pro Ala Val Leu Gln Ser Ser Gly
Leu Tyr Ser Leu Ser Ser Val Val Thr Val Pro Ser
Ser Ser Leu Gly Thr Gln Thr Tyr Ile Cys Asn Val
```

```
Asn His Lys Pro Ser Asn Thr Lys Val Asp Lys Lys
Val Glu Pro Lys Ser Cys Asp Lys Thr His Thr Cys
Pro Pro Cys Pro Ala Pro Gln Leu Leu Gly Gly Pro
Ser Val Phe Leu Phe Pro Pro Lys Pro Lys Asp Thr
Leu Met Ile Ser Arg Thr Pro Glu Val Thr Cys Val
Val Val Asp Val Ser His Glu Asp Pro Glu Val Lys
Phe Asn Trp Tyr Val Asp Gly Val Glu Val His Asn
Ala Lys Thr Lys Pro Arg Glu Glu Gln Tyr Asn Ser
Thr Tyr Arg Val Val Ser Val Leu Thr Val Leu His
Gln Asp Trp Leu Asn Gly Lys Glu Tyr Lys Cys Lys
Val Ser Asn Lys Ala Leu Pro Ala Pro Ile Glu Lys
Thr Ile Ser Lys Ala Lys Gly Gln Pro Arg Glu Pro
Gln Val Tyr Thr Leu Pro Pro Ser Arg Asp Glu Leu
Thr Lys Asn Gln Val Ser Leu Thr Cys Leu Val Lys
Gly Phe Tyr Pro Ser Asp Ile Ala Val Glu Trp Glu
Ser Asn Gly Gln Pro Glu Asn Asn Tyr Lys Thr Thr
Pro Pro Val Leu Asp Ser Asp Gly Ser Phe Phe Leu
Tyr Ser Lys Leu Thr Val Asp Lys Ser Arg Trp Gln
Gln Gly Asn Val Phe Ser Cys Ser Val Met His Glu
Ala Leu His Asn His Tyr Thr Gln Lys Ser Leu Ser
Leu Ser Pro Gly Lys
```

A version of humanized 10D5 antibody comprising a light chain having a mature variable region having the amino acid sequence designated SEQ ID NO: 28 and a heavy chain having a mature variable region having the amino acid sequence designated SEQ ID NO: 29 is shown below.

```
Humanized 10D5 Light Chain Variable Region
                                        (SEQ ID NO: 28)
Asp Val Leu Met Thr Gln Thr Pro Leu Ser Leu Pro
Val Ser Leu Gly Asp Gln Ala Ser Ile Ser Cys Arg
Ser Ser Gln Asn Ile Ile His Ser Asn Gly Asn Thr
Tyr Leu Glu Trp Tyr Leu Gln Lys Pro Gly Gln Ser
Pro Lys Leu Leu Ile Tyr Lys Val Ser Asn Arg Phe
Ser Gly Val Pro Asp Arg Phe Ser Gly Ser Gly Ser
Gly Thr Asp Phe Thr Leu Lys Ile Lys Lys Val Glu
Ala Glu Asp Leu Gly Ile Tyr Tyr Cys Phe Gln Gly
Ser His Val Pro Leu Thr Phe Gly Ala Gly Thr Lys
Leu Glu Leu Glu Humanized 10D5 Heavy Chain Variable Region
                                        (SEQ ID NO: 29)
Gln Ala Thr Leu Lys Glu Ser Gly Pro Gly Ile Leu
Gln Ser Ser Gln Thr Leu Ser Leu Thr Cys Ser Phe
Ser Gly Phe Ser Leu Ser Thr Ser Gly Met Gly Val
Ser Trp Ile Arg Gln Pro Ser Gly Lys Gly Leu Glu
Trp Leu Ala His Ile Tyr Trp Asp Asp Asp Lys Arg
Tyr Asn Pro Ser Leu Lys Ser Arg Leu Thr Ile Ser
Lys Asp Thr Ser Arg Lys Gln Val Phe Leu Lys Ile
Thr Ser Val Asp Pro Ala Asp Thr Ala Thr Tyr Tyr
Cys Val Arg Arg Pro Ile Thr Pro Val Leu Val Asp
Ala Met Asp Tyr Trp Gly Gln Gly Thr Ser Val Thr
Val Ser Ser
```

In another aspect, the antibody may be a 12B4 antibody or variant thereof, as described in U.S. Patent Publication No. 20040082762A1 and International Patent Publication No. WO 03/077858A2. 12B4 is a mAb that specifically binds to an N-terminal epitope located in the human β-amyloid peptide, specifically, residues 3-7.

12A11 or a chimeric or humanized or nanobody form thereof is a preferred antibody. The 12A11 antibody or a variant thereof, is described in U.S. Patent Publication No. 20050118651, U.S. Patent Publication No. 20060198851, International Patent Publication No. WO 04/108895, and International Patent Publication No. WO 06/066089, all of which are incorporated by reference in their entirety herein for all purposes. 12A11 is a mAb that specifically binds to an N-terminal epitope located in the human β-amyloid peptide, specifically, residues 3-7. A cell line producing the 12A11 monoclonal antibody was deposited at the ATCC (American Type Culture Collection, 10801 University Boulevard, Manassas, Va. 20110-2209) on Dec. 12, 2005 and has the ATCC accession number PTA-7271.

A first version of the humanized 12A11 antibody comprising a light chain having the amino acid sequence designated SEQ ID NO: 7 and a heavy chain having the amino acid sequence designated SEQ ID NO: 8 (version 1) is described in US 20050118651 A1 published on Jun. 2, 2005, which is incorporated herein by reference for all purposes.

```
Humanized 12A11 Light Chain
                                        (SEQ ID NO: 7)
Asp Val Val Met Thr Gln Ser Pro Leu Ser Leu Pro
Val Thr Pro Gly Glu Pro Ala Ser Ile Ser Cys Arg
Ser Ser Gln Ser Ile Val His Ser Asn Gly Asn Thr
Tyr Leu Glu Trp Tyr Leu Gln Lys Pro Gly Gln Ser
Pro Gln Leu Leu Ile Tyr Lys Val Ser Asn Arg Phe
Ser Gly Val Pro Asp Arg Phe Ser Gly Ser Gly Ser
Gly Thr Asp Phe Thr Leu Lys Ile Ser Arg Val Glu
Ala Glu Asp Val Gly Val Tyr Tyr Cys Phe Gln Ser
Ser His Val Pro Leu Thr Phe Gly Gln Gly Thr Lys
Leu Glu Ile Lys Humanized 12A11 Heavy Chain (version 1)
                                        (SEQ ID NO: 8)
Gln Val Gln Leu Val Glu Ser Gly Gly Gly Val Val
Gln Pro Gly Arg Ser Leu Arg Leu Ser Cys Ala Phe
Ser Gly Phe Ser Leu Ser Thr Ser Gly Met Ser Val
Gly Trp Ile Arg Gln Ala Pro Gly Lys Gly Leu Glu
Trp Leu Ala His Ile Trp Trp Asp Asp Asp Lys Tyr
Tyr Asn Pro Ser Leu Lys Ser Arg Leu Thr Ile Ser
Lys Asp Thr Ser Lys Asn Thr Val Tyr Leu Gln Met
Asn Ser Leu Arg Ala Glu Asp Thr Ala Val Tyr Tyr
Cys Ala Arg Arg Thr Thr Thr Ala Asp Tyr Phe Ala
Tyr Trp Gly Gln Gly Thr Thr Val Thr Val Ser Ser
```

A second version of the humanized 12A11 antibody comprising a light chain having the amino acid sequence designated SEQ ID NO: 7 and a heavy chain having the amino acid sequence designated SEQ ID NO: 9 (version 2) is described in US 20050118651 A1 published on Jun. 2, 2005, which is incorporated herein by reference for all purposes.

```
Humanized 12A11 Heavy Chain (version 2)
                                        (SEQ ID No: 9)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A third version of the humanized 12A11 antibody comprising a light chain having the amino acid sequence designated SEQ ID NO: 7 and a heavy chain having the amino acid sequence designated SEQ ID NO: 10 (version 2.1) is described in US 20050118651 A1 published on Jun. 2, 2005, which is incorporated herein by reference for all purposes.

```
Humanized 12A11 Heavy Chain (version 2.1)
                                        (SEQ ID NO: 10)
Gln Val Gln Leu Val Glu Ser Gly Gly Gly Val Val Gln Pro Gly Arg Ser Leu Arg Leu Ser Cys Ala Phe
```

-continued

```
Ser Gly Phe Thr Leu Ser Thr Ser Gly Met Ser Val

Gly Trp Ile Arg Gln Ala Pro Gly Lys Gly Leu Glu

Trp Val Ala His Ile Trp Trp Asp Asp Asp Lys Tyr

Tyr Asn Pro Ser Leu Lys Ser Arg Phe Thr Ile Ser

Lys Asp Asn Ser Lys Asn Thr Leu Tyr Leu Gln Met

Asn Ser Leu Arg Ala Glu Asp Thr Ala Val Tyr Tyr

Cys Ala Arg Arg Thr Thr Thr Ala Asp Tyr Phe Ala

Tyr Trp Gly Gln Gly Thr Thr Val Thr Val Ser Ser
```

A fourth version of the humanized 12A11 antibody comprising a light chain having the amino acid sequence designated SEQ ID NO: 7 and a heavy chain having the amino acid sequence designated SEQ ID NO: 11 (version 3) is described in US 20050118651 A1 published on Jun. 2, 2005, which is incorporated herein by reference for all purposes.

```
Humanized 12A11 Heavy Chain (version 3)
                                    (SEQ ID NO: 11)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Set Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asn Tyr Phe Ala Tyr Trp Gly Gln Gly Thr Thr Val Thr Val Ser Ser
```

A fifth version of the humanized 12A11 antibody comprising a light chain having the amino acid sequence designated SEQ ID NO: 7 and a heavy chain having the amino acid sequence designated SEQ ID NO: 12 (version 4.1) is described in US 20050118651 A1 published on Jun. 2, 2005, which is incorporated herein by reference for all purposes.

```
Humanized 12A11 Heavy Chain (version 4.1)
                                    (SEQ ID NO: 12)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Leu Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A sixth version of the humanized 12A11 antibody comprising a light chain having the amino acid sequence designated SEQ ID NO: 7 and a heavy chain having the amino acid sequence designated SEQ ID NO: 13 (version 4.2) is described in US 20050118651 A1 published on Jun. 2, 2005, which is incorporated herein by reference for all purposes.

```
Humanized 12A11 Heavy Chain (version 4.2)
                                    (SEQ ID NO: 13)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Leu Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

An seventh version of the humanized 12A11 antibody comprising a light chain having the amino acid sequence designated SEQ ID NO: 7 and a heavy chain having the amino acid sequence designated SEQ ID NO: 14 (version 4.3) is described in US 20050118651 A1 published on Jun. 2, 2005, which is incorporated herein by reference for all purposes.

```
Humanized 12A11 Heavy Chain (version 4.3)
                                    (SEQ ID NO: 14)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Phe Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A eighth version of the humanized 12A11 antibody comprising a light chain having the amino acid sequence designated SEQ ID NO: 7 and a heavy chain having the amino acid sequence designated SEQ ID NO: 15 (version 4.4) is described in US 20050118651 A1 published on Jun. 2, 2005, which is incorporated herein by reference for all purposes.

```
Humanized 12A11 Heavy Chain (version 4.4)
                                    (SEQ ID NO: 15)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr
```

-continued

Tyr Asn Pro Ser Leu Lys Ser Arg Leu Thr Ile Ser

Lys Asp Thr Ser Lys Asn Thr Leu Tyr Leu Gln Met

Asn Ser Leu Arg Ala Glu Asp Thr Ala Val Tyr Tyr

Cys Ala Arg Arg Thr Thr Thr Ala Asp Tyr Phe Ala

Tyr Trp Gly Gln Gly Thr Thr Val Thr Val Ser Ser

A ninth version of the humanized 12A11 antibody comprising a light chain having the amino acid sequence designated SEQ ID NO: 7 and a heavy chain having the amino acid sequence designated SEQ ID NO: 16 (version 5.1) is described in US 20050118651 A1 published on Jun. 2, 2005, which is incorporated herein by reference for all purposes.

Humanized 12A11 Heavy Chain (version 5.1)
(SEQ ID NO: 16)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Leu Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser A tenth version of the humanized 12A11 antibody comprising a light chain having the amino acid sequence designated SEQ ID NO: 7 and a heavy chain having the amino acid sequence designated SEQ ID NO: 17 (version 5.2) is described in US 20050118651 A1 published on Jun. 2, 2005, which is incorporated herein by reference for all purposes.

Humanized 12A11 Heavy Chain (version 5.2)
(SEQ ID NO: 17)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Phe Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser An eleventh version of the humanized 12A11 antibody comprising a light chain having the amino acid sequence designated SEQ ID NO: 7 and a heavy chain having the amino acid sequence designated SEQ ID NO: 18 (version 5.3) is described in US 20050118651 A1 published on Jun. 2, 2005, which is incorporated herein by reference for all purposes.

Humanized 12A11 Heavy Chain (version 5.3)
(SEQ ID NO: 18)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Leu Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser Val A twelfth version of the humanized 12A11 antibody comprising a light chain having the amino acid sequence designated SEQ ID NO: 7 and a heavy chain having the amino acid sequence designated SEQ ID NO: 19 (version 5.4) is described in US 20050118651 A1 published on Jun. 2, 2005, which is incorporated herein by reference for all purposes.

Humanized 12A11 Heavy Chain (version 5.4)
(SEQ ID NO: 19)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser Val A thirteenth version of the humanized 12A11 antibody comprising a light chain having the amino acid sequence designated SEQ ID NO: 7 and a heavy chain having the amino acid sequence designated SEQ ID NO: 20 (version 5.5) is described in US 20050118651 A1 published on Jun. 2, 2005, which is incorporated herein by reference for all purposes.

Humanized 12A11 Heavy Chain (version 5.5)
(SEQ ID NO: 20)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Leu Thr Ile Ser -continued

```
Lys Asp Thr Ser Lys Asn Thr Leu Tyr Leu Gln Met

Asn Ser Leu Arg Ala Glu Asp Thr Ala Val Tyr Tyr

Cys Ala Arg Arg Thr Thr Thr Ala Asp Tyr Phe Ala

Tyr Trp Gly Gln Gly Thr Thr Val Thr Val Ser Ser
```

A fourteenth version of the humanized 12A11 antibody comprising a light chain having the amino acid sequence designated SEQ ID NO: 7 and a heavy chain having the amino acid sequence designated SEQ ID NO: 21 (version 5.6) is described in US 20050118651 A1 published on Jun. 2, 2005, which is incorporated herein by reference for all purposes.

```
Humanized 12A11 Heavy Chain (version 5.6)
                                         (SEQ ID NO: 21)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Phe Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A fifteenth version of the humanized 12A11 antibody comprising a light chain having the amino acid sequence designated SEQ ID NO: 7 and a heavy chain having the amino acid sequence designated SEQ ID NO: 22 (version 6.1) is described in US 20050118651 A1 published on Jun. 2, 2005, which is incorporated herein by reference for all purposes.

```
Humanized 12A11 Heavy Chain (version 6.1)
                                         (SEQ ID NO: 22)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A sixteenth version of the humanized 12A11 antibody comprising a light chain having the amino acid sequence designated SEQ ID NO: 7 and a heavy chain having the amino acid sequence designated SEQ ID NO: 23 (version 6.2) is described in US 20050118651 A1 published on Jun. 2, 2005, which is incorporated herein by reference for all purposes.

```
Humanized 12A11 Heavy Chain (version 6.2)
                                         (SEQ ID NO: 23)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Leu Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A seventeenth version of the humanized 12A11 antibody comprising a light chain having the amino acid sequence designated SEQ ID NO: 7 and a heavy chain having the amino acid sequence designated SEQ ID NO: 24 (version 6.3) is described in US 20050118651 A1 published on Jun. 2, 2005, which is incorporated herein by reference for all purposes.

```
Humanized 12A11 Heavy Chain (version 6.3)
                                         (SEQ ID NO: 24)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Phe Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A eighteenth version of the humanized 12A11 antibody comprising a light chain having the amino acid sequence designated SEQ ID NO: 7 and a heavy chain having the amino acid sequence designated SEQ ID NO: 25 (version 6.4) is described in US 20050118651 A1 published on Jun. 2, 2005, which is incorporated herein by reference for all purposes.

```
Humanized 12A11 Heavy Chain (version 6.4)
                                         (SEQ ID NO: 25)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Lys Asp Thr Ser Lys Asn Thr Leu Tyr Leu Gln Met Asn Ser Leu Arg Ala Glu Asp Thr Ala Val Tyr Tyr
```

-continued

Cys Ala Arg Arg Thr Thr Ala Asp Tyr Phe Ala

Tyr Trp Gly Gln Gly Thr Thr Val Thr Val Ser Ser

A nineteenth version of the humanized 12A11 antibody comprising a light chain having the amino acid sequence designated SEQ ID NO: 7 and a heavy chain having the amino acid sequence designated SEQ ID NO: 26 (version 7) is described in US 20050118651 A1 published on Jun. 2, 2005, which is incorporated herein by reference for all purposes.

Humanized 12A11 Heavy Chain (version 7)
(SEQ ID NO: 26)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Val Arg Gln Ala Pro Gly Lys Gly Leu Glu Trp Leu Ala His Ile Trp Trp Asp Asp Asp Lys Tyr Tyr Asn Pro Ser Leu Lys Ser Arg Leu Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Ala Asp Tyr Phe Ala Tyr Trp Gly Gln Gly Thr Thr Val Thr Val Ser Ser A twentieth version of the humanized 12A11 antibody comprising a light chain having the amino acid sequence designated SEQ ID NO: 7 and a heavy chain having the amino acid sequence designated SEQ ID NO: 27 (version 8) is described in US 20050118651 A1 published on Jun. 2, 2005, which is incorporated herein by reference for all purposes.

Humanized 12A11 Heavy Chain (version 27)
(SEQ ID NO: 8)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Leu Thr Ile Ser Lys Asp Asn Ser Lys Asn Thr Val Tyr Leu Gln Met Asn Ser Leu Arg Ala Glu Asp Thr Ala Val Tyr Tyr Cys Ala Arg Arg Thr Thr Ala Asp Tyr Phe Ala Tyr Trp Gly Gln Gly Thr Thr Val Thr Val Ser Ser In yet another aspect, the antibody may be a 6C6 antibody, or a variant thereof, as described in a U.S. Patent Publication No. US 20060165682 and International Patent Publication No. WO 06/06604 entitled "Humanized Antibodies that Recognize Beta Amyloid Peptide." 6C6 is a mAb that specifically binds to an N-terminal epitope located in the human β-amyloid peptide, specifically, residues 3-7. A cell line producing the antibody 6C6 was deposited on Nov. 1, 2005, with the ATCC under the terms of the Budapest Treaty and assigned accession number PTA-7200.

In yet another aspect, the antibody may be a 2H3 antibody as described in U.S. Patent Publication US 20060257396. 2H3 is a mAb that specifically binds to an N-terminal epitope located in the human β-amyloid peptide, specifically, residues 2-7. A cell line producing the antibody 2H3 was deposited on Dec. 13, 2005, with the ATCC under the terms of the Budapest Treaty and assigned accession number PTA-7267.

In yet another aspect, the antibody may be a 3A3 antibody as described in U.S. Patent Publication US 20060257396. 3A3 is a mAb that specifically binds to an N-terminal epitope located in the human β-amyloid peptide, specifically, residues 3-7. A cell line producing the antibody 3A3 was deposited on Dec. 13, 2005, with the ATCC under the terms of the Budapest Treaty and assigned accession number PTA-7269.

In yet another aspect, the antibody may be 2B1, 1C2 or 9G8. Cell lines producing the antibodies 2B1, 1C2 and 9G8 were deposited on Nov. 1, 2005, with the ATCC under the terms of the Budapest Treaty and were assigned accession numbers PTA-7202, PTA-7199 and PTA-7201, respectively.

Antibodies for use in the present invention may be recombinantly or synthetically produced. For example, the antibody may be produced by a recombinant cell culture process, using, e.g., CHO cells, NIH 3T3 cells, PER.C6® cells, NS0 cells, VERO cells, chick embryo fibroblasts, or BHK cells. In addition, antibodies with minor modifications that retain the primary functional property of binding Aβ peptide are contemplated by the present invention. In a particular aspect, the antibody is a humanized anti Aβ peptide 3D6 antibody that selectively binds Aβ peptide. More specifically, the humanized anti Aβ peptide 3D6 antibody is designed to specifically bind to an $NH_2$-terminal epitope, for example, amino acid residues 1-5, located in the human β-amyloid 1-40 or 1-42 peptide found in plaque deposits in the brain (e.g., in patients suffering from Alzheimer's disease).

Prophylactic and Therapeutic Methods

The present invention is directed inter alia to treatment of Alzheimer's and other amyloidogenic diseases by administration of therapeutic immunological reagents (e.g., humanized immunoglobulins) to specific epitopes within Aβ to a patient under conditions that generate a beneficial therapeutic response in a patient (e.g., induction of phagocytosis of Aβ, reduction of plaque burden, inhibition of plaque formation, reduction of neuritic dystrophy, improving cognitive function, and/or reversing, treating or preventing cognitive decline) in the patient, for example, for the prevention or treatment of an amyloidogenic disease. The invention is also directed to use of the disclosed immunological reagents (e.g., humanized immunoglobulins) in the manufacture of a medicament for the treatment or prevention of an amyloidogenic disease.

The term "treatment" as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

In one aspect, the invention provides methods of preventing or treating a disease associated with amyloid deposits of Aβ in the brain of a patient. Such diseases include Alzheimer's disease, Down's syndrome and cognitive impairment. The latter can occur with or without other characteristics of an amyloidogenic disease. Some methods of the invention entail administering an effective dosage of an antibody that specifically binds to a component of an amyloid deposit to the patient. Such methods are particularly useful for preventing or treating Alzheimer's disease in human patients. Exemplary methods entail administering an effective dosage of an antibody that binds to Aβ. Preferred methods entail administering an effective dosage of an antibody that specifically binds to an epitope within residues 1-10 of Aβ, for example, antibodies that specifically bind to an epitope within residues 1-3 of Aβ, antibodies that specifically bind to an epitope within residues 1-4 of Aβ, antibodies that specifically bind to an epitope within residues 1-5 of Aβ, antibodies that specifically bind to an epitope within residues 1-6 of Aβ, antibodies that specifically bind to an epitope within residues 1-7 of Aβ, or antibodies that specifically bind to an epitope within residues 3-7 of Aβ. In yet another aspect, the invention features administering antibodies that bind to an epitope comprising a free N-terminal residue of Aβ. In yet another aspect, the invention features administering antibodies that bind to an epitope within residues of 1-10 of Aβ wherein residue 1 and/or residue 7 of Aβ is aspartic acid. In yet another aspect, the invention features administering antibodies that specifically bind to Aβ peptide without binding to full-length amyloid precursor protein (APP). In yet another aspect, the isotype of the antibody is human IgG1.

In yet another aspect, the invention features administering antibodies that bind to an amyloid deposit in the patient and induce a clearing response against the amyloid deposit. For example, such a clearing response can be effected by Fc receptor mediated phagocytosis.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained.

The methods can be used on both asymptomatic patients and those currently showing symptoms of disease. The antibodies used in such methods can be human, humanized, chimeric or nonhuman antibodies, or fragments thereof (e.g., antigen binding fragments) and can be monoclonal or polyclonal, as described herein. In yet another aspect, the invention features administering antibodies prepared from a human immunized with Aβ peptide, which human can be the patient to be treated with antibody.

In another aspect, the invention features administering an antibody with a pharmaceutical carrier as a pharmaceutical composition. Alternatively, the antibody can be administered to a patient by administering a polynucleotide encoding at least one antibody chain. The polynucleotide is expressed to produce the antibody chain in the patient. Optionally, the polynucleotide encodes heavy and light chains of the antibody. The polynucleotide is expressed to produce the heavy and light chains in the patient. In other aspects, the patient is monitored for level of administered antibody in the blood of the patient.

The invention thus fulfills a longstanding need for therapeutic regimes for preventing or ameliorating the neuropathology and, in some patients, the cognitive impairment associated with Alzheimer's disease.

Patients Amenable to Treatment

Patients amenable to treatment include individuals at risk of disease but not showing symptoms, as well as patients presently showing symptoms. In the case of Alzheimer's disease, virtually anyone is at risk of suffering from Alzheimer's disease if he or she lives long enough. Therefore, the present methods can be administered prophylactically to the general population without the need for any assessment of the risk of the subject patient. The present methods are especially useful for individuals who have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, supra). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by ADRDA criteria as discussed in the Examples section.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

Patients amenable to treatment include patients 50 to 87 years of age, patients suffering from mild to moderate Alzheimer's disease, patients having an MMSE score of 14-26, patients having a diagnosis of probable Alzheimer's disease based on Neurological and Communicative Disorders and Stroke-Alzheimer's disease Related Disorders (NINCDS-ADRDA) criteria, and/or patients having an Rosen Modified Hachinski Ischemic score less than or equal to 4. Patients with MRI an scan consistent with the diagnosis of Alzheimer's disease, i.e., that there are no other abnormalities present on the MRI that could be attributed to other diseases, e.g. stroke, traumatic brain injury, arachnoid cysts, tumors, etc are also amendable to treatment.

The methods of the invention are particular amendable for patients that have no history or evidence of any of the following: encephalitis; clinically evident stroke; clinically significant carotid or vertebrobasilar stenosis or plaque; seizures, excluding febrile seizures in childhood; any significant autoimmune disease or disorder of the immune system; and/or clinically significant renal disorder. The methods of the invention are particular amendable for patients that have had no clinically significant infection within the 30 days before treatment commences, e.g., a chronic persistent or acute infection. The methods of the invention are particular amendable for patients that have not been treated with immunosuppressive medication (e.g., systemic corticosteroids) within 90 days before treatment commences (topical and nasal corticosteroids and inhaled corticosteroids for asthma are permitted) or chemotherapeutic agents for malignancy within 3 years before treatment commences. The methods of the invention are also particular amendable for patients that have no clinically significant abnormality on physical, neurological, laboratory, or EKG examination (e.g. atrial fibrillation) if the abnormality could be detrimental to the patient. The methods of the invention are also particular amendable for patients that do not use anticonvulsants for seizure, anti-Parkinson's, anticoagulant (excluding the use of aspirin 325 mg/day or less), or narcotic medications.

Treatment Regimes and Dosages

In prophylactic applications, pharmaceutical compositions or medicaments are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease.

In some methods, administration of agent reduces or eliminates myocognitive impairment in patients that have not yet developed characteristic Alzheimer's pathology. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. The term "immune response" or "immunological response" includes the development of a humoral (antibody mediated) and/or a cellular (mediated by antigen-specific T cells or their secretion products) response directed against an antigen in a recipient subject. Such a response can be an active response, i.e., induced by administration of immunogen, or a passive response, i.e., induced by administration of immunoglobulin or antibody or primed T-cells.

An "immunogenic agent" or "immunogen" is capable of inducing an immunological response against itself on administration to a mammal, optionally in conjunction with an adjuvant. Typically, the immune response is monitored and repeated dosages are given if the immune response starts to wane.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages need to be titrated to optimize safety and efficacy.

For passive immunization, the dosage ranges from about 0.0001 to 100, and more usually 0.01 to 5 mg/kg of the host body weight. For example, dosage ranges can be less than 20 mg/kg body weight or 10 mg/kg body weight or within the range of 1.0 to 7 mg/kg. For passive immunization, the preferred dosage ranges from about 0.5 to less than 5 mg/kg, and more usually 0.5 to 3 mg/kg, of the host body weight. For example dosages can be less than 5 mg/kg body weight or 1.5 mg/kg body weight or within the range of 0.5 to 1.5 mg/kg, preferably at least 1.5 mg/kg. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months.

Exemplary passive dosage schedules include 1.5-3 mg/kg or 1.5 mg/kg every thirteen weeks. Agents of the invention are usually administered on multiple occasions. Intervals between single dosages can be weekly, monthly, every thirteen weeks, or yearly. Intervals can also be irregular as indicated by measuring blood levels of antibody to Aβ in the patient.

In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 10 to 250 mg of antibody per dose, with dosages of from 5 to 25 mg being more commonly used) at relatively short intervals is sometimes required until progression of the disease is reduced or terminated, and preferably until the patient shows partial or complete amelioration of symptoms of disease. Thereafter, the patent can be administered a prophylactic regime.

Therapeutic agents can be administered by parenteral, topical, intravenous, oral, subcutaneous, intraarterial, intracranial, intraperitoneal, intranasal or intramuscular means for prophylactic and/or therapeutic treatment. The most typical route of administration of a passive immunogenic agent is intravenous infusion although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection or intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in treatment of amyloidogenic disease. In the case of Alzheimer's and Down's syndrome, in which amyloid deposits occur in the brain, agents of the invention can also be administered in conjunction with other agents that increase passage of the agents of the invention across the blood-brain barrier.

Pharmaceutical Compositions

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immuno stimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation, which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249: 1527 (1990) and Hanes, *Advanced Drug Delivery Reviews* 28:97 (1997)). The agents of this invention can be administered in the form of a depot injection or implant preparation, which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., *Eur. J. Immunol.* 25:3521 (1995); Cevc et al., *Biochem. Biophys. Acta* 1368:201-15 (1998)).

Monitoring the Course of Treatment

The invention provides methods of monitoring treatment in a patient suffering from or susceptible to Alzheimer's, i.e., for monitoring a course of treatment being administered to a patient. The methods can be used to monitor both therapeutic treatment on symptomatic patients and prophylactic treatment on asymptomatic patients. In particular, the methods are useful for monitoring passive immunization (e.g., measuring level of administered antibody).

Some methods entail determining a baseline value, for example, of an antibody level or profile in a patient, before administering a dosage of agent, and comparing this with a value for the profile or level after treatment. A significant increase (i.e., greater than the typical margin of experimental error in repeat measurements of the same sample, expressed as one standard deviation from the mean of such measurements) in value of the level or profile signals a positive treatment outcome (i.e., that administration of the agent has achieved a desired response). If the value for immune response does not change significantly, or decreases, a negative treatment outcome is indicated.

In other methods, a control value (i.e., a mean and standard deviation) of level or profile is determined for a control population. Typically the individuals in the control population have not received prior treatment. Measured values of the level or profile in a patient after administering a therapeutic agent are then compared with the control value. A significant increase relative to the control value (e.g., greater than one standard deviation from the mean) signals a positive or sufficient treatment outcome. A lack of significant increase or a decrease signals a negative or insufficient treatment outcome. Administration of agent is generally continued while the level is increasing relative to the control value. As before, attainment of a plateau relative to control values is an indicator that the administration of treatment can be discontinued or reduced in dosage and/or frequency.

In other methods, a control value of the level or profile (e.g., a mean and standard deviation) is determined from a control population of individuals who have undergone treatment with a therapeutic agent and whose levels or profiles have reached a plateau in response to treatment. Measured values of levels or profiles in a patient are compared with the control value. If the measured level in a patient is not significantly different (e.g., more than one standard deviation) from the control value, treatment can be discontinued. If the level in a patient is significantly below the control value, continued administration of agent is warranted. If the level in the patient persists below the control value, then a change in treatment may be indicated.

In other methods, a patient who is not presently receiving treatment but has undergone a previous course of treatment is monitored for antibody levels or profiles to determine whether a resumption of treatment is required. The measured level or profile in the patient can be compared with a value previously achieved in the patient after a previous course of treatment. A significant decrease relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

The tissue sample for analysis is typically blood, plasma, serum, mucous fluid or cerebrospinal fluid from the patient. The sample is analyzed, for example, for levels or profiles of antibodies to Aβ peptide, e.g., levels or profiles of humanized antibodies. ELISA methods of detecting antibodies specific to Aβ are described in the Examples section. In some methods, the level or profile of an administered antibody is determined using a clearing assay, for example, in an in vitro phagocytosis assay, as described herein. In such methods, a tissue sample from a patient being tested is contacted with amyloid deposits (e.g., from a PDAPP mouse) and phagocytic cells bearing Fc receptors. Subsequent clearing of the amyloid deposit is then monitored. The existence and extent of clearing response provides an indication of the existence and level of antibodies effective to clear Aβ in the tissue sample of the patient under test.

The antibody profile following passive immunization typically shows an immediate peak in antibody concentration followed by an exponential decay. Without a further dosage, the decay approaches pretreatment levels within a period of days to months depending on the half-life of the antibody administered. For example the half-life of some human antibodies is of the order of 20 days.

In some methods, a baseline measurement of antibody to Aβ in the patient is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dosage of antibody is administered. In some methods, peak or subsequent measured levels less background are compared with reference levels previously determined to constitute a beneficial prophylactic or therapeutic treatment regime in other patients. If the measured antibody level is significantly less than a reference level (e.g., less than the mean minus one standard deviation of the reference value in population of patients benefiting from treatment) administration of an additional dosage of antibody is indicated.

Additional methods include monitoring, over the course of treatment, any art-recognized physiologic symptom (e.g., physical or mental symptom) routinely relied on by researchers or physicians to diagnose or monitor amyloidogenic diseases (e.g., Alzheimer's disease). For example, one can monitor cognitive impairment. The latter is a symptom of Alzheimer's disease and Down's syndrome but can also occur without other characteristics of either of these diseases. For example, cognitive impairment can be monitored by determining a patient's score on the Mini-Mental State Exam in accordance with convention throughout the course of treatment.

The patient may be monitored by at least one type of assessment selected from the group of consisting of Mini-Mental State Exam (MMSE), Alzheimer's Disease Assessment Scale—cognitive (ADAS-COG), Clinician Interview-Based Impression (CIBI), Neurological Test Battery (NTB), Disability Assessment for Dementia (DAD), Clinical Dementia Rating-sum of boxes (CDR-SOB), Neuropsychiatric Inventory (NPI), Positron Emission Tomography (PET Imaging) scan, Magnetic Resonance Imaging (MRI) scan, an EKG and measurement of blood pressure. The type of assessment may be administered on multiple occasions. For example, an MMSE may be performed before administering a dosage of the immunogenic agent, and at week 4, week 6, week 16, 6 months, and 1 year after administering the dosage of the immunogenic agent. In some patients an MMSE may be performed before administering a dosage of the immunogenic agent, and at week 6, and week 16. An MRI scan may be performed every 3 months, every 6 months, or every year.

Patients may be monitored for posterior reversible encephalopathy syndrome (PRES) or vascular edema after administration of an antibody within a range of about 0.5 mg/kg to less than 5 mg/kg, wherein the antibody specifically binds to beta amyloid peptide (Aβ) with a binding affinity of at least $10^7$ $M^{-1}$. PRES classically consists of reversible vasogenic edema in the posterior circulation territories, however, conversion to irreversible cytoxic edema has been described. PRES is typically characterized by headache, nausea, vomiting, confusion, seizures, visual abnormalities, altered mental functioning, ataxia, frontal symptoms, parietal symptoms, stupor, and focal neurologic signs. In addition to the foregoing clinical symptoms, MRI scans or Fluid Attenuated Inversion Recovery (FLAIR) sequence imaging can be used to indicate the presence on PRES. (See *Pediatric Neurology*, 20(3):241-243; *AJNR*, 26:825-830; *NEJM*, 334(8): 494-500; *Pediatr Nephrol*, 18:1161-1166; *Internal Medicine Journal*, 35:83-90; *JNNP*, 68:790-791; *AJNR*, 23:1038-1048; *Pak J Med Sci*, 21(2):149-154 and, *AJNR*, 21:1199-1209.)

Patients may be monitored for PRES or vascular edema monthly, every four months, every six months, or yearly. The patient may be monitored for at least one clinical symptom associated with PRES or vascular edema. The monitoring may comprise performing an MRI scan. The monitoring may further comprise performing FLAIR sequence imaging. The results of the monitoring may impact the dosing regime. For example, if PRES or vascular edema is detected, dosing may be suspended or dosages may be reduced or the intervals between dosages may be increased.

Patients with PRES or vascular edema may have their blood pressure measured for hypertension. If hypertension is detected in the patient, the patient may be treated for the hypertension by administration of an antihypertensive. The antihypertensive may be selected from the group consisting of hydroclorothiazide, angiotensin-converting enzyme (ACE) inhibitors, angiotensin II-receptor blockers (ARB), beta blockers, and calcium channel blockers. Patient with PRES or vascular edema may be treated with steroids such as dexamethasone or methyprednisol.

C. Kits

The invention further provides therapeutic products. The products comprise a glass vial and instructions. The glass vial contains a formulation comprising about 10 mg to about 250 mg of a humanized anti Aβ antibody, about 4% mannitol or about 150 mM NaCl, about 5 mM to about 10 mM histidine, and about 10 mM methionine. The instructions to monitor a patient to whom the formulation is administered for PRES and or vascular edema are included with the products. In some therapeutic products the glass vial contains a formulation comprising about 10 mg of a humanized anti Aβ antibody in about 10 mM histidine, about 10 mM methionine, about 4% mannitol, and about 0.005% polysorbate-80 (vegetable derived), with a pH of about 6.0. The instructions to monitor a patient to whom the formulation is administered for PRES or vascular edema are included with the products.

EXAMPLE I

Prevention and Treatment of Human Subjects

Bapineuzumab (AAB-001) is a humanized monoclonal antibody to Aβ. The objective of this study is to determine the safety and tolerability of single doses of bapineuzumab in AD.

Methods: Randomized, double-blind, placebo-controlled single ascending dose trial of bapineuzumab infusion in patients with mild to moderate AD. Patients enrolled in the trial met all of the following criteria:

1. Diagnosis of probable Alzheimer's disease (AD) according to the National Institute of Neurological and Communicative Disorders and Stroke-Alzheimer's disease and Related Disorders (NINCDS-ADRDA) criteria.
2. Age from 50 to 87 years, inclusive.
3. Mini-Mental Status Examination (MMSE) score of 14-26.
4. Rosen Modified Hachinski Ischemic score≤4.
5. Lives at home with appropriate caregiver capable of accompanying the patient on all clinic visits, or community dwelling with caregiver capable of accompanying the patient on all clinic visits and visiting with the patient approximately 5 times per week for the duration of the study.
6. Screening visit brain magnetic resonance imaging (MRI) scan consistent with the diagnosis of AD, i.e., that there are no other abnormalities present on the MRI that can be attributed to other diseases (e.g., stroke, traumatic brain injury, arachnoid cysts, tumors, etc).
7. Surgically sterile or 2 years post-menopausal.
8. Fluent in English and evidences adequate premorbid intellectual functioning. Patient must have adequate visual and auditory abilities to perform all aspects of the cognitive and functional assessments.
9. Receiving stable doses of medication(s) for the treatment of non-excluded medical condition(s) for at least 30 days prior to screening. If a patient is taking acetylcholinesterase inhibitors or memantine, then these medication(s) must be maintained on a stable dose regimen for at least 60 days prior to screening evaluations.

Anyone of the following criteria excluded a patient from being enrolled in the trial:

1. Significant neurological disease, other than AD, that may affect cognition.
2. Current presence of a clinically significant major psychiatric disorder (e.g., major Depressive Disorder) according to the criteria of the Diagnostic and Statistical Manual of Mental Disorders, Fourth Edition (DSM-IV), or symptom (e.g., hallucinations), that could affect the patient's ability to complete the study.
3. Current clinically significant systemic illness that is likely to result in deterioration of the patient's condition or affect the patient's safety during the study.
4. History or evidence of any of the following: encephalitis; clinically evident stroke; clinically significant carotid or vertebrobasilar stenosis or plaque; seizures, excluding febrile seizures in childhood; any clinically significant autoimmune disease or disorder of the immune system; clinically significant renal disorder.
5. Clinically significant infection with the last 30 days (e.g., chronic persistent or acute infection).
6. Treatment with immunosuppressive medications (e.g., systemic corticosteroids) within the last 90 days (topical and nasal corticosteroids and inhaled corticosteroids for asthma are permitted) or chemotherapeutic agents for malignancy within the last 3 years.
7. Myocardial infarction within the last 2 years.
8. History of cancer within the last 5 years, with the exception of non-metastatic basal cell carcinoma and squamous cell carcinoma of the skin.
9. Other clinically significant abnormality on physical, neurological, laboratory, or ECG examination (e.g., atrial fibrillation) that could compromise the study or be detrimental to the patient.
10. Hemoglobin less than 11 g/dL.
11. History of alcohol or drug dependence or abuse within the last 2 years.
12. Hamilton Psychiatric Rating Scale for Depression (HAM-D) (17-item) score>12.
13. Current use of anticonvulsants for seizure, anti-Parkinson's, anticoagulant (excluding the use of aspirin 325 mg/day or less), or narcotic medications.
14. Current use of prescription or nonprescription medication for cognitive enhancement other than cholinesterase inhibitors and memantine. Current cholinesterase inhibitor and memantine use is prohibited unless the following conditions are met: (a) maintained on a stable dose regimen for at least 60 days prior to screening; (b) patient is free of any clinically significant side effects attributable to the drug; and (c) patient and caregiver agree that, barring unforeseen circumstances, they will continue the same regimen for the duration of the trial.
15. Unless maintained on a stable dose regimen for at least 30 days prior to screening, any other medications with the potential to affect cognition other than those mentioned in #18 (including, but not limited to, anxiolytics, sedatives, hypnotics, antipsychotics, antidepressants, over-the-counter (OTC) sleeping aids, sedating anti-allergy medications, vitamin E, thyroid supplements, and vitamin B12 supplements by injection).
16. Patients who have discontinued cholinesterase inhibitors, memantine, cognitive enhancing agents, or drugs that potentially affect cognition in the 60 days prior to screening.
17. Use of an experimental medication (chemical compound) or device for AD or any other investigational medication or device for indication other than treatment for AD within 30 days prior to screening or within 5 half-lives of use of such a medication prior to screening, whichever is longer.
18. Any prior experimental treatment with AN1792, AAB-001, ACC-001, or other experimental immunotherapeutic or vaccine for AD.
19. Any prior treatment with a biologic product other than those mentioned in #18 for the treatment of AD within the last 3 years.
20. Patients who have donated blood (routine blood donation) in the 90 days prior to screening.
21. Any known hypersensitivity to any of the excipients contained in the study drug formulation.
22. Presence of pacemakers, aneurysm clips, artificial heart valves, ear implants, metal fragments of foreign objects in the eyes, skin, or body that would contraindicate a brain MRI scan.
23. Weight greater than 120 kg (264 lbs).

Figure 3:
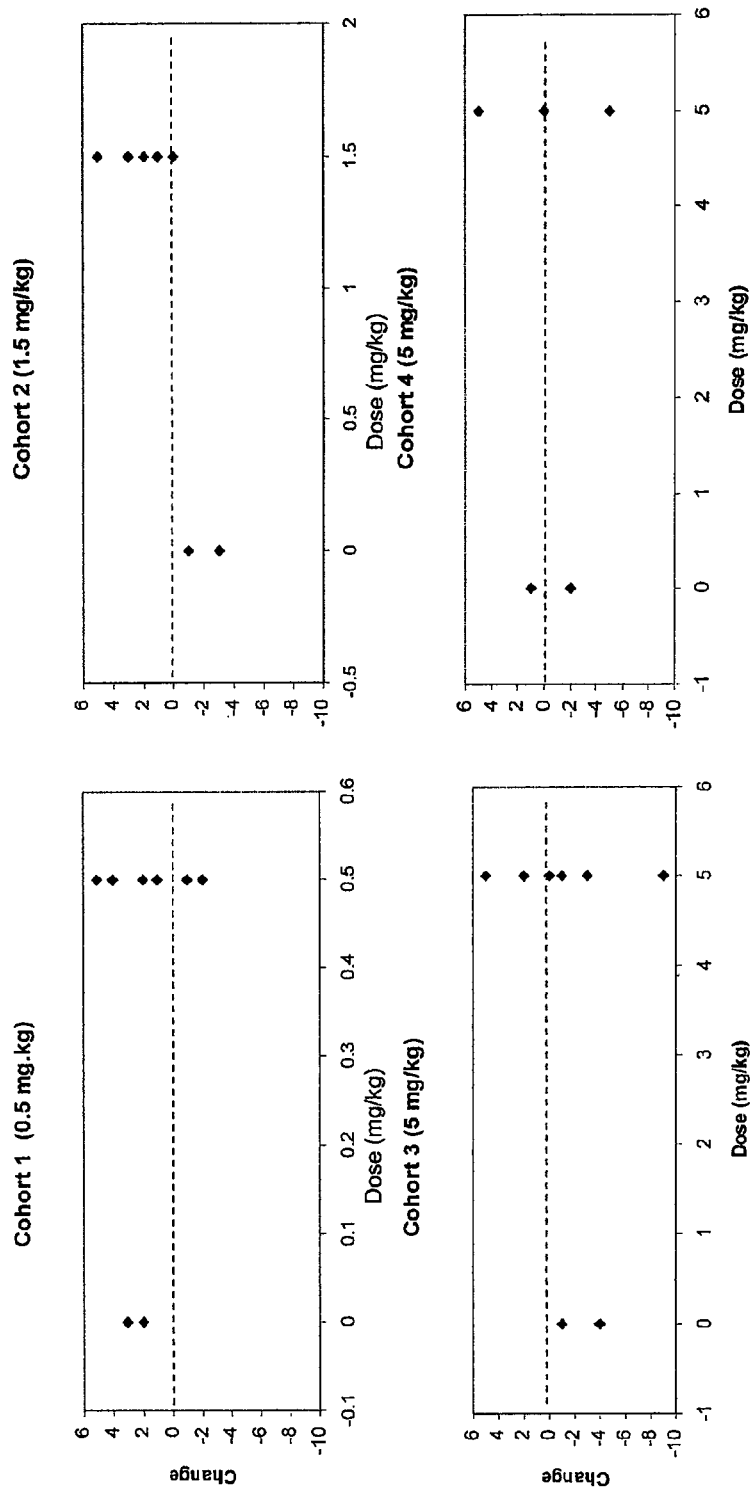
FIG. 3 shows the change from baseline MMSE by cohort at month 4.

Results: 30 patients received bapineuzumab at doses of 0.5 mg/kg (6 active, 2 placebo) 1.5 mg/kg (6 active, 2 placebo) and 5 mg/kg (10 active, 4 placebo). 3/10 patients at 5 mg/kg developed MRI abnormalities, consisting predominantly of high signal abnormalities on FLAIR sequences, and the study did not continue past that dose. In two patients these were seen on routine surveillance scans without clinical symptoms, however a third patient experienced increased confusion. The MRI FLAIR abnormalities resolved in all three cases by 12 weeks post-dose. As part of the safety assessments MMSE was performed at baseline, week 4, week 16, 6 months and at 1 year. FIG. 2 shows the average MMSE change from baseline. FIG. 3 shows the change from baseline MMSE by cohort at month 4. At week 16, the prespecified primary time point for analysis, the treatment difference relative to placebo favored the treated group at the 0.5 mg/kg dose (treatment vs. placebo difference of 2.0, p=0.152) and reached statistical significance at the 1.5 mg/kg dose (treatment vs. placebo difference of 2.5, p=0.047). There was no significant difference in MMSE change relative to placebo for the 5.0 mg/kg group. FIG. 4 shows the mean, median and standard deviation MMSE change from baseline at month four. FIG. 5 shows the results of statistical testing of the MMSE change from baseline at month four. No correlation was found between the MRI FLAIR abnormalities and the difference in MMSE change.

Plasma A-beta was elevated from baseline levels in a dose dependent fashion, peaking approximately 24 hours after the infusion. Pharmacokinetic analysis showed a half life of 22-28 days and was supportive of a 13-week dosing interval in multiple dosing.

Conclusion: In this small study, MMSE was statistically significantly improved compared with placebo at the 1.5 mg/kg dose of bapineuzumab. The highest single infusion dose of 5 mg/kg was associated with MRI FLAIR abnormalities which resolved.

Although the foregoing invention has been described in detail for purposes of clarity of understanding, it will be obvious that certain modifications may be practiced within the scope of the appended claims. All publications and patent documents cited herein, as well as text appearing in the figures, are hereby incorporated by reference in their entirety for all purposes to the same extent as if each were so individually denoted.

EXAMPLE II

Pharmacokinetic Study of AAB-001

The objective of this study is to determine human pharmacokinetics (PK) after intravenous administration of AAB-001.

Methods: Randomized, double-blind, placebo-controlled multiple ascending dose trial of AAB-001 administered intravenously. 6 doses of AAB-001 were administered intravenously q13 wk. There were four dose cohorts were 0.15, 0.5, 1.0 and 2.0 mg/kg.

Results: PK was predictable and dose-independent. PK-CL 0.05-0.06 mL/h/kg across all dose levels. Dose-proportional exposure. Very little accumulation with q13 wk IV dosing, although quantifiable pre-infusion concentrations at all dose levels. t½ ranged from 21-34 hours. At steady-state, Cavg after 0.5 mg/kg AAB-001 (i.e., ~35 mg) ~3.3 µg/mL. See FIG. 9. Cavg after 0.5 mg/kg AAB-001 of ~3.3 µg/mL is close to the 3.7 µg/mL concentration found to be efficacious in PDAPP mice. FIG. 10 shows mean serum AAB-001 concentration vs. time profiles following intravenous administration of AAB-001 at doses of 0.15, 0.5, 1.0, and 2.0 mg/kg.

Figure 11:
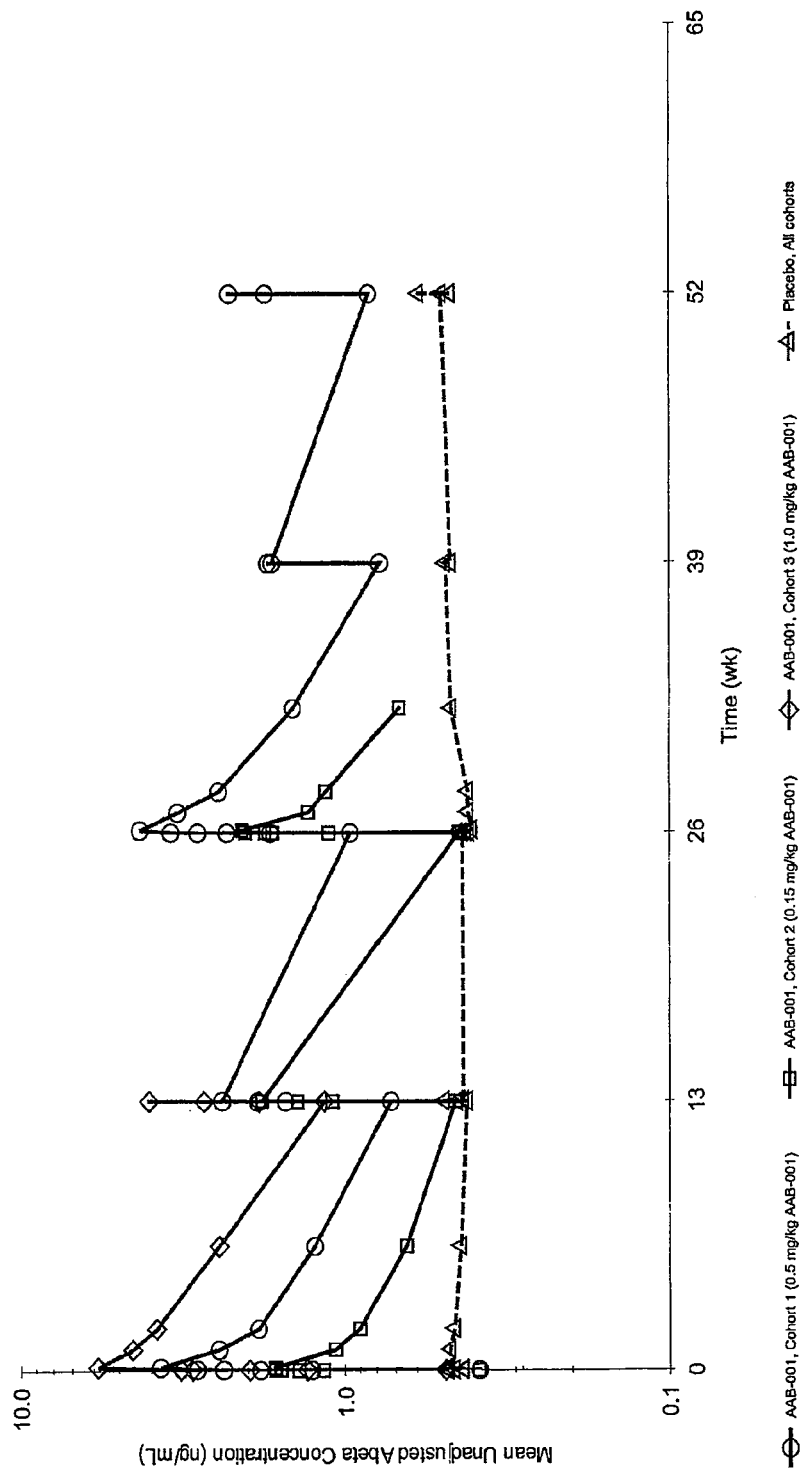
FIG. 11 shows plasma Aβ levels following intravenous administration of AAB-001 at doses of 0.15, 0.5, and 1.0 mg/kg.

Plasma Aβ concentrations tend to mirror AAB-001 concentrations. At end of 13-week dosing interval, plasma Aβ levels above baseline levels and above placebo group at ≥0.5 mg/kg AAB-001 dose levels. See FIG. 11. tmax ranged from 14-48 hours.

Serum anti-AAB-001 antibody levels have been undetectable in any of the samples (up to pre-Infusion #6 for the 0.5 mg/kg AAB-001 cohort).

From the foregoing it will be apparent that the invention provides for a number of uses. For example, the invention provides for the use of any of the antibodies to Aβ described above in the treatment, prophylaxis or diagnosis of amyloidogenic disease, or in the manufacture of a medicament or diagnostic composition for use in the same.

---

We claim:

1. A method of therapeutically treating Alzheimer's disease, comprising administering by intravenous infusion to a human patient suffering from the disease a dosage of an antibody that specifically binds to an N-terminal fragment of beta-amyloid peptide (Aβ) with a binding affinity of at least $10^7$ M$^{-1}$, and monitoring the patient for posterior reversible encephalopathy syndrome (PRES) or vascular edema, wherein the method comprises the steps of:
 (a) administering a first dosage to the patient;
 (b) monitoring the patient and detecting the presence of PRES or vascular edema at a first time point;
 (c) optionally administering a second dosage to the patient after the monitoring in step (b) detects presence of PRES or vascular edema;
 (d) monitoring the patient and detecting the absence of PRES or vascular edema at a second time point; and
 (e) administering another dosage to the patient after the monitoring in step (d) indicates absence of PRES or vascular edema,
 wherein the dosages in (a) and (e) are higher than the dosage in (c) if a dosage is administered in (c).

2. A method of therapeutically treating Alzheimer's disease, comprising administering by intravenous infusion to a human patient suffering from the disease a dosage of an antibody within a range of about 0.5 mg/kg to less than 5 mg/kg, wherein the antibody specifically binds to an N-terminal fragment of beta-amyloid peptide (Aβ) with a binding affinity of at least $10^7$ M$^{-1}$, and monitoring the patient for posterior reversible encephalopathy syndrome (PRES) or vascular edema, wherein the method comprises the steps of:
 (a) administering a first dosage to the patient;
 (b) monitoring the patient and detecting the presence of PRES or vascular edema at a first time point;
 (c) optionally administering a second dosage to the patient after the monitoring in step (b) detects presence of PRES or vascular edema;
 (d) monitoring the patient and detecting the absence of PRES or vascular edema at a second time point; and
 (e) administering another dosage to the patient after the monitoring in step (d) indicates absence of PRES or vascular edema,
 wherein the dosages in (a) and (e) are higher than the dosage in (c) if a dosage is administered in (c).

3. The method of claim 1 or 2, wherein the antibody is a humanized antibody.

4. The method of claim 3, wherein the humanized antibody is a humanized version of mouse antibody 3D6 expressed by the hybridoma deposited under ATCC under No. PTA-5130.

5. The method of claim 4, wherein the humanized antibody is bapineuzumab.

6. The method of claim 5, wherein the first dosage is 3-5 mg/kg and the second dosage is 0.5 to 3 mg/kg.

7. The method of claim 6, wherein the second dosage is half of the first dosage.

8. The method of claim 1 or 2, wherein the dosages are administered every 8 to 16 weeks.

9. The method of claim 8, wherein the dosages are administered every 10 to 14 weeks.

10. The method of claim 9, wherein the dosages are administered every 13 weeks.

11. The method of claim 1 or 2, wherein the first and third dosages are the same.

12. The method of claim 1 or 2, wherein the first dosage is 3-5 mg/kg and the second dosage is 0.5 to 3 mg/kg.

13. The method of claim 12, wherein the second dosage is half of the first dosage.

14. The method of claim 1 or 2, wherein the monitoring comprises performing an MRI scan.

15. The method of claim 14, wherein the monitoring further comprises performing a FLAIR (Fluid Attenuated Inversion Recovery) sequence imaging.

16. The method of claim 15, further comprising reducing or suspending the second dosage based on an outcome of the FLAIR sequence imaging that is indicative of PRES or vascular edema.

17. The method of claim 14, wherein the MRI scan is every 3 months, every 6 months, or every year.

18. The method of claim 15, wherein the FLAIR sequence imaging is every 3 months, every 6 months, or every year.

19. The method of claim 14, wherein the monitoring comprises identifying of at least one clinical symptom associated with PRES or vascular edema.

20. The method of claim 19, wherein the at least one clinical symptom is selected from the group consisting of headache, nausea, vomiting, confusion, seizures, visual abnormalities, altered mental functioning, ataxia, frontal symptoms, parietal symptoms, stupor, and focal neurologic signs.

21. The method of claim 20, further comprising reducing or suspending the second dosage based on an identification of at least one clinical symptom associated with PRES or vascular edema.

22. The method of claim 14, further comprising reducing or suspending the second dosage based on an outcome of the MRI scan that is indicative of PRES or vascular edema.

23. The method of claim 22, further comprising determining presence or absence of hypertension in the patient, wherein if the patient has hypertension, the method further comprises administering an antihypertensive.

24. The method of claim 23, wherein the antihypertensive is selected from the group consisting of hydroclorothiazide, angiotensin-converting enzyme (ACE) inhibitors, angiotensin II-receptor blockers (ARB), beta blockers, and calcium channel blockers.

25. The method of claim 22, wherein the method further comprises administering a steroid to the patient to treat the PRES or vascular edema.

26. The method of claim 25, wherein the steroid is dexamethasone.

27. The method of claim 25, wherein the steroid is methyprednisolone.

28. The method of claim 1 or 2, further comprising monitoring the patient by at least one type of assessment selected from the group of consisting of Mini-Mental State Exam (MMSE), Alzheimer's Disease Assessment Scale-cognitive (ADAS-COG), Clinician Interview-Based Impression (CIBI), Neurological Test Battery (NTB), Disability Assessment for Dementia (DAD), Clinical Dementia Rating-sum of boxes (CDR-SOB), Neuropsychiatric Inventory (NPI), Positron Emission Tomography (PET Imaging) scan, Magnetic Resonance Imaging (MRI) scan, EKG and measurement of blood pressure.

29. The method of claim 28, wherein the assessment type is an Alzheimer's Disease Assessment Scale-cognitive (ADAS-COG).

30. The method of claim 29, wherein the ADAS-COG is administered on multiple occasions.

31. The method of claim 28, wherein the assessment type is a Neurological Test Battery (NTB).

32. The method of claim 31, wherein the NTB is administered on multiple occasions.

33. The method of claim 28, wherein the type of assessment is an MMSE.

34. The method of claim 33, wherein the MMSE is administered on multiple occasions.

35. The method of claim 34, wherein the MMSE is performed before administering the first dosage, and at week 4, week 16, 6 months, and 1 year after administering the first dosage.

36. The method of claim 34, wherein the MMSE score measured after administration is higher than a previously assessed MMSE score.

* * * * *

UNITED STATES PATENT AND TRADEMARK OFFICE
CERTIFICATE OF CORRECTION

PATENT NO.       : 8,613,920 B2                                                    Page 1 of 1
APPLICATION NO. : 12/297636
DATED            : December 24, 2013
INVENTOR(S)      : Lieberburg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 215 days.

Signed and Sealed this
Twenty-second Day of September, 2015

Michelle K. Lee
*Director of the United States Patent and Trademark Office*

SEQUENCE LISTING

```
<160> NUMBER OF SEQ ID NOS: 31

<210> SEQ ID NO 1
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80
```

-continued

```
Ser Arg Val Glu Ala Glu Asp Val Gly Val Tyr Tyr Cys Trp Gln Gly
            85                  90                  95

Thr His Phe Pro Arg Thr Phe Gly Gln Gly Thr Lys Val Glu Ile Lys
            100                 105                 110

<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
        115

<210> SEQ ID NO 3
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Tyr Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Thr His Phe Pro Arg Thr Phe Gly Gln Gly Thr Lys Val Glu Ile Lys
            100                 105                 110

<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
        115

<210> SEQ ID NO 5
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 6
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Gln Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Gln Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Gln Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 7
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ser
                85                  90                  95

Ser His Val Pro Leu Thr Phe Gly Gln Gly Thr Lys Leu Glu Ile Lys
            100                 105                 110

<210> SEQ ID NO 8
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln

Gly Thr Thr Val Thr Val Ser Ser
        115                 120

<210> SEQ ID NO 9
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 10
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 11
<211> LENGTH: 120
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
    50                  55                  60

Leu Lys Ser Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
```

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
        50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 14
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
        50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
        50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 18
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser Val
        115                 120

<210> SEQ ID NO 19
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser Val
        115                 120

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65              70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65              70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
            50                  55                  60

Leu Lys Ser Arg Phe Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 23
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
        50                  55                  60

Leu Lys Ser Arg Leu Thr Ile Ser Lys Asp Thr Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
        50                  55                  60

Leu Lys Ser Arg Phe Thr Ile Ser Lys Asp Thr Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln

```
                        100                 105                 110
Gly Thr Thr Val Thr Val Ser Ser
        115                 120

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Val Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 27
<211> LENGTH: 120
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 27

Gln Val Gln Leu Val Glu Ser Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
50                  55                  60

Leu Lys Ser Arg Leu Thr Ile Ser Lys Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Ile His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Lys Lys Val Glu Ala Glu Asp Leu Gly Ile Tyr Tyr Cys Phe Gln Gly
                85                  90                  95

Ser His Val Pro Leu Thr Phe Gly Ala Gly Thr Lys Leu Glu Leu Glu
            100                 105                 110

<210> SEQ ID NO 29
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Ala Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu

-continued

```
                 35                  40                  45
Trp Leu Ala His Ile Tyr Trp Asp Asp Lys Arg Tyr Asn Pro Ser
     50                  55                  60
Leu Lys Ser Arg Leu Thr Ile Ser Lys Asp Thr Ser Arg Lys Gln Val
 65                  70                  75                  80
Phe Leu Lys Ile Thr Ser Val Asp Pro Ala Asp Thr Ala Thr Tyr Tyr
                 85                  90                  95
Cys Val Arg Arg Pro Ile Thr Pro Val Leu Val Asp Ala Met Asp Tyr
                100                 105                 110
Trp Gly Gln Gly Thr Ser Val Thr Val Ser Ser
                115                 120

<210> SEQ ID NO 30
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Val Val Met Thr Gln Ser Pro Leu Ser Leu Pro Val Thr Pro Gly
 1               5                  10                  15
Glu Pro Ala Ser Ile Ser Cys Lys Ser Ser Gln Ser Leu Leu Asp Ser
                20                  25                  30
Asp Gly Lys Thr Tyr Leu Asn Trp Leu Leu Gln Lys Pro Gly Gln Ser
            35                  40                  45
Pro Gln Arg Leu Ile Tyr Leu Val Ser Lys Leu Asp Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Trp Gln Gly
                85                  90                  95
Thr His Phe Pro Arg Thr Phe Gly Gln Gly Thr Lys Val Glu Ile Lys
                100                 105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215

<210> SEQ ID NO 31
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

-continued

```
                420             425             430
Ala Leu His Asn His Tyr Thr Gln Lys Ser Leu Ser Leu Ser Pro Gly
            435                 440                 445
Lys
```